United States Patent
Fuji et al.

(10) Patent No.: US 9,654,883 B2
(45) Date of Patent: May 16, 2017

(54) STRAIN SENSING ELEMENT, PRESSURE SENSOR, MICROPHONE, BLOOD PRESSURE SENSOR, AND TOUCH PANEL

(71) Applicant: KABUSHIKI KAISHA TOSHIBA, Tokyo (JP)

(72) Inventors: Yoshihiko Fuji, Kawasaki Kanagawa (JP); Hideaki Fukuzawa, Kawasaki Kanagawa (JP); Shiori Kaji, Kawasaki Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 256 days.

(21) Appl. No.: 14/476,200

(22) Filed: Sep. 3, 2014

(65) Prior Publication Data
US 2015/0082901 A1    Mar. 26, 2015

(30) Foreign Application Priority Data
Sep. 20, 2013 (JP) .................. 2013-196243

(51) Int. Cl.
*G01L 1/24* (2006.01)
*H04R 23/00* (2006.01)
(Continued)

(52) U.S. Cl.
CPC ........... *H04R 23/00* (2013.01); *B81B 3/0078* (2013.01); *G01L 1/125* (2013.01); *G01L 9/0041* (2013.01);
(Continued)

(58) Field of Classification Search
CPC ....... G01B 7/24; A61B 5/021; A61B 5/02108; A61B 5/02141; A61B 2562/0247;
(Continued)

(56) References Cited

U.S. PATENT DOCUMENTS 6,889,555 B1 * 5/2005 Ganapathi ............... G01L 1/125
  73/728
7,690,263 B2 * 4/2010 Jen ........................ G01L 1/2287
  73/777

(Continued)

FOREIGN PATENT DOCUMENTS

JP    2002-148132    5/2002
JP    2002-357489    12/2002
(Continued)

OTHER PUBLICATIONS

Office Action issued by the Taiwanese Intellectual Property Office on Nov. 11, 2015, for Taiwanese Patent Application No. 103130571, and English-language translation thereof.

(Continued)

*Primary Examiner* — Harshad R Patel
*Assistant Examiner* — Brandi Hopkins
(74) *Attorney, Agent, or Firm* — Finnegan, Henderson, Farabow, Garrett & Dunner LLP

(57) ABSTRACT

According to one embodiment, a strain sensing element provided on a deformable substrate includes: a first magnetic layer; a second magnetic layer; a spacer layer; and a bias layer. Magnetization of the second magnetic layer changes according to deformation of the substrate. The spacer layer is provided between the first magnetic layer and the second magnetic layer. The second magnetic layer is provided between the spacer layer and the bias layer. The bias layer is configured to apply a bias to the second magnetic layer.

31 Claims, 38 Drawing Sheets

(51) Int. Cl.
  *B81B 3/00* (2006.01)
  *G01L 1/12* (2006.01)
  *G01L 9/00* (2006.01)
  *G01L 9/16* (2006.01)
  *H04R 3/00* (2006.01)
  *H04R 31/00* (2006.01)

(52) U.S. Cl.
  CPC .............. *G01L 9/16* (2013.01); *H04R 23/006* (2013.01); *B81B 2201/0257* (2013.01); *B81B 2201/06* (2013.01); *H04R 3/00* (2013.01); *H04R 31/006* (2013.01); *H04R 2201/003* (2013.01); *H04R 2410/03* (2013.01); *H04R 2420/07* (2013.01); *H04R 2499/11* (2013.01)

(58) Field of Classification Search
  CPC ......... G01L 1/125; G01L 9/0044; G01L 9/16; G01L 9/0048; G01L 1/12; G01L 9/0051; G01L 9/0042; H04R 15/00; H04R 2410/00; H04R 1/00; H04R 1/08; H01L 41/125; G01R 3/00; Y10T 29/49007; B81C 1/00158
  USPC ...................... 73/779, 862.69, 725, 754, 726
  See application file for complete search history.

(56) References Cited

U.S. PATENT DOCUMENTS

| | | | |
|---|---|---|---|
| 2002/0085323 | A1 | 7/2002 | Smith et al. |
| 2004/0050172 | A1* | 3/2004 | Quandt .................. G01L 1/125 73/779 |
| 2005/0201022 | A1 | 9/2005 | Horng et al. |
| 2005/0219773 | A1 | 10/2005 | Li et al. |
| 2007/0186666 | A1* | 8/2007 | Ruehrig .................. G01L 9/16 73/779 |
| 2007/0268633 | A1 | 11/2007 | Horng et al. |
| 2009/0135529 | A1 | 5/2009 | Shimazawa et al. |
| 2011/0295128 | A1 | 12/2011 | Yuasa et al. |
| 2012/0079887 | A1 | 4/2012 | Giddings et al. |
| 2012/0241619 | A1 | 9/2012 | Fukuzawa et al. |
| 2012/0245477 | A1 | 9/2012 | Giddings et al. |
| 2013/0069182 | A1* | 3/2013 | Ohsawa .................. H01L 29/82 257/421 |
| 2013/0076687 | A1 | 3/2013 | Giddings et al. |
| 2013/0079648 | A1 | 3/2013 | Fukuzawa et al. |
| 2013/0170669 | A1 | 7/2013 | Fukuzawa et al. |
| 2013/0255069 | A1 | 10/2013 | Higashi et al. |
| 2013/0255393 | A1 | 10/2013 | Fukuzawa et al. |
| 2014/0069200 | A1 | 3/2014 | Yuasa et al. |
| 2014/0090486 | A1 | 4/2014 | Fuji et al. |
| 2014/0137658 | A1 | 5/2014 | Higashi et al. |
| 2014/0137668 | A1* | 5/2014 | Fukuzawa ............. B81B 3/0086 73/862.69 |
| 2014/0207006 | A1 | 7/2014 | Giddings et al. |
| 2014/0207007 | A1 | 7/2014 | Giddings et al. |

FOREIGN PATENT DOCUMENTS

| | | |
|---|---|---|
| JP | 2005-260226 | 9/2005 |
| JP | 2005-286340 | 10/2005 |
| JP | 2006-179566 | 7/2006 |
| JP | 2009-134850 | 6/2009 |
| JP | 2011-244938 | 12/2011 |
| JP | 2012-78186 | 4/2012 |
| JP | 2012-176294 | 9/2012 |
| JP | 2012-204479 | 10/2012 |
| JP | 5214806 | 3/2013 |
| JP | 2013-70732 | 4/2013 |
| JP | 2013-72712 | 4/2013 |
| JP | 2013-73374 | 4/2013 |
| JP | 2013-165977 | 8/2013 |
| JP | 2013-205255 | 10/2013 |
| JP | 2013-205403 | 10/2013 |
| JP | 2014-52360 | 3/2014 |
| JP | 2014-74606 | 4/2014 |
| JP | 2014-102171 | 6/2014 |
| JP | 2014-103539 | 6/2014 |

OTHER PUBLICATIONS

Office Action issued by the Taiwanese Intellectual Property Office on Jun. 11, 2015, for Taiwanese Patent Application No. 103130571, and English-language translation thereof.

Löhndorf et al., "Highly sensitive strain sensors based on magnetic tunneling junctions," Applied Physics Letters, Jul. 8, 2002, 81:313-315.

Meyners et al., "Pressure sensor based on magnetic tunnel junctions," Journal of Applied Physics, Aug. 4, 2009, 105:07C914-1-07C914-3.

English-language machine translation of JP 2006-179566, published Jul. 6, 2006.

English-language machine translation of JP 2002-357489, published Dec. 13, 2002.

\* cited by examiner

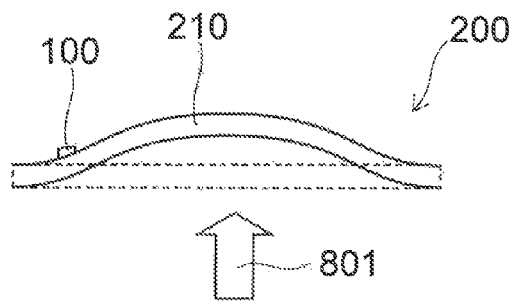
FIG. 1A
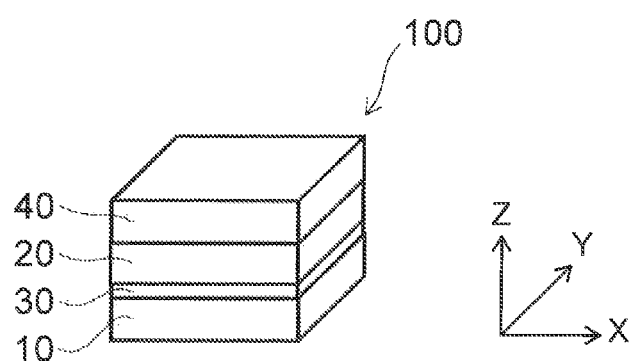
FIG. 1B
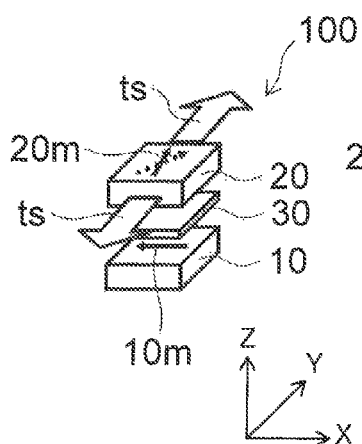 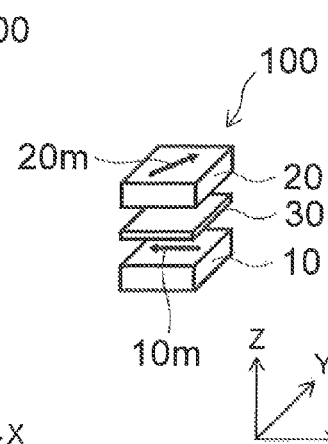 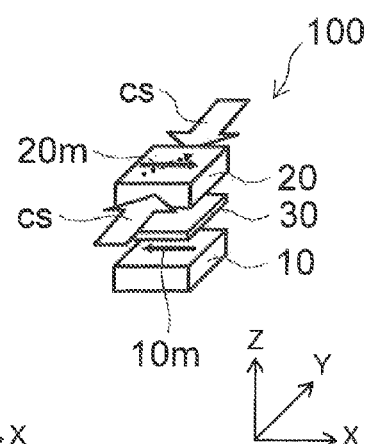
FIG. 2A  FIG. 2B  FIG. 2C

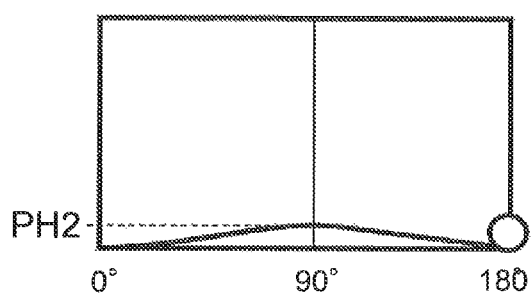 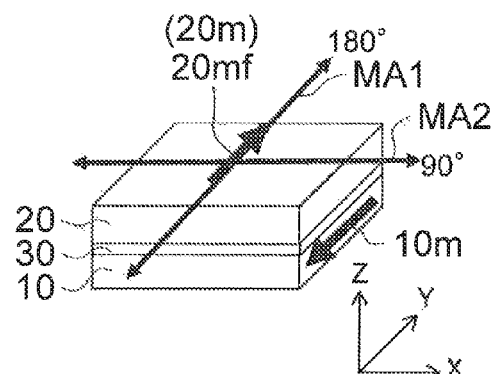
FIG. 14A    FIG. 14B
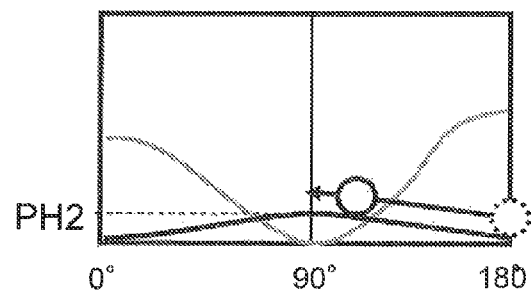 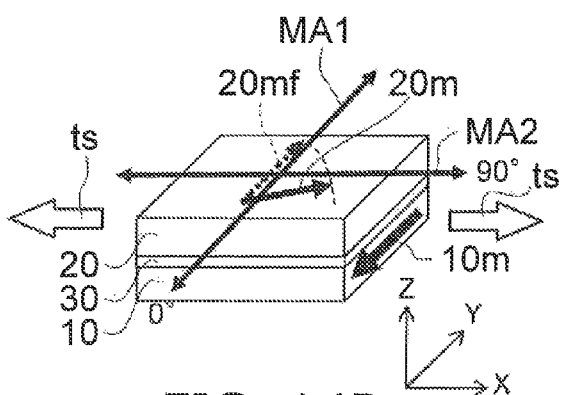
FIG. 14C    FIG. 14D
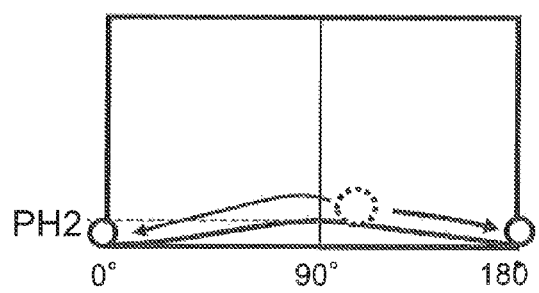 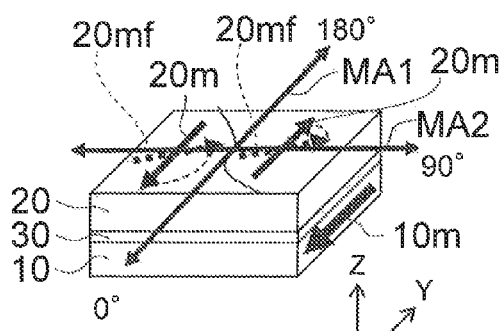
FIG. 14E    FIG. 14F

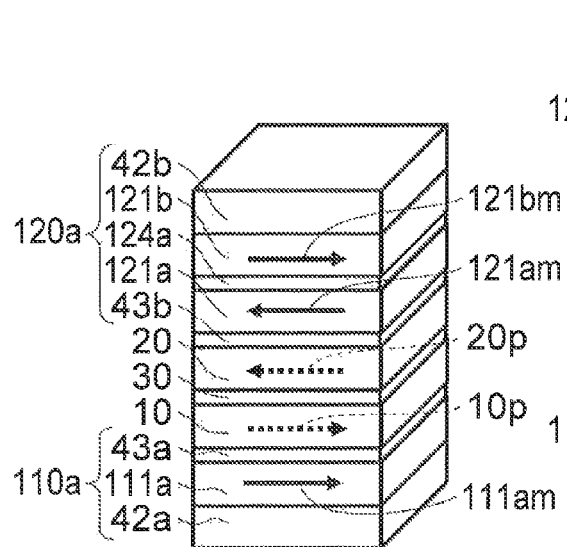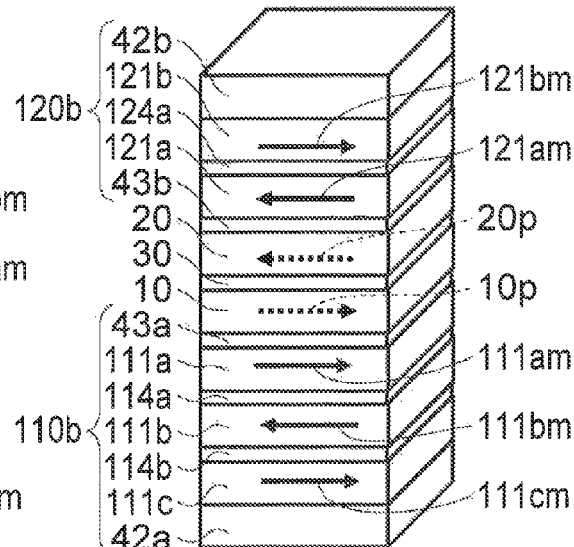
FIG. 24A
FIG. 24B
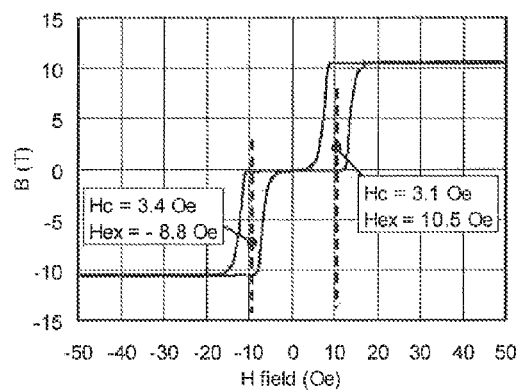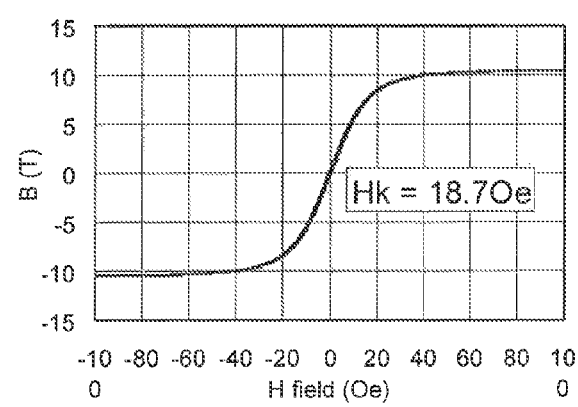
FIG. 25A
FIG. 25B
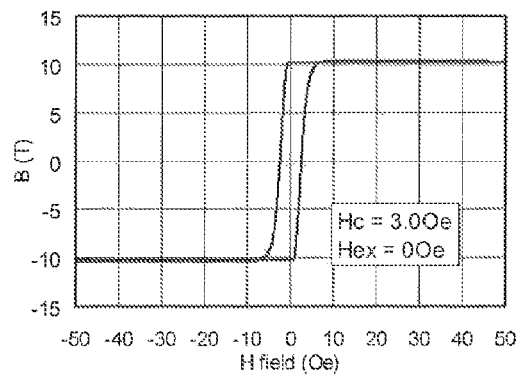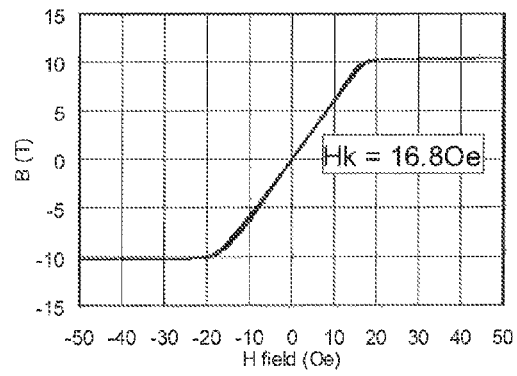
FIG. 25C
FIG. 25D

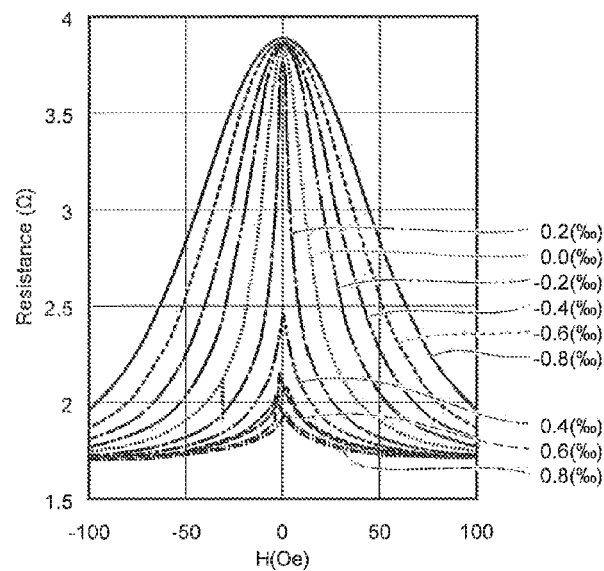
FIG. 26A
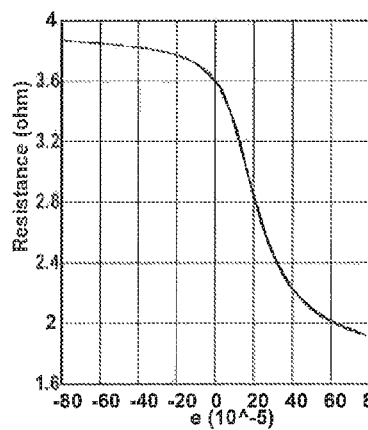 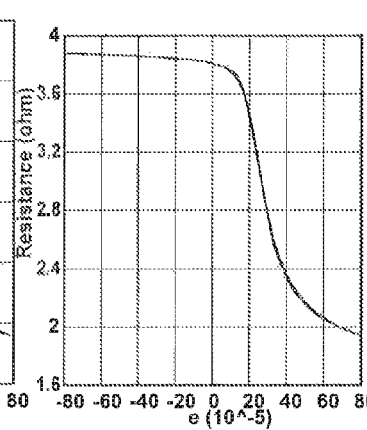 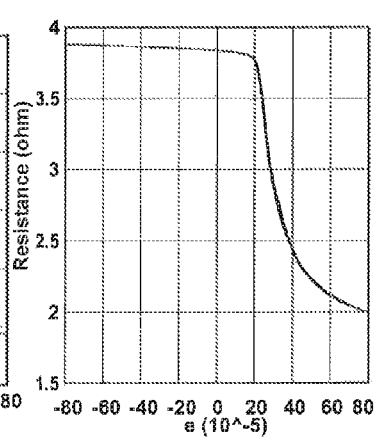
FIG. 26B  FIG. 26C  FIG. 26D

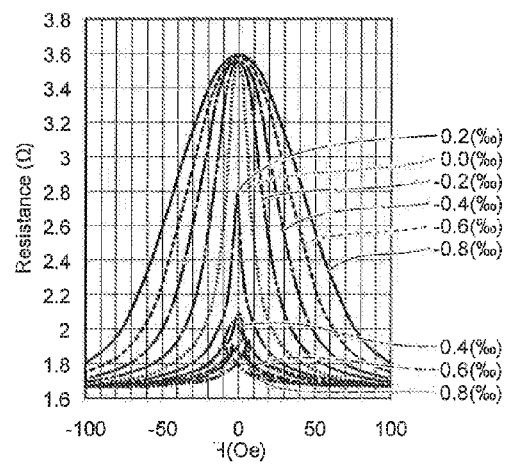
FIG. 27A
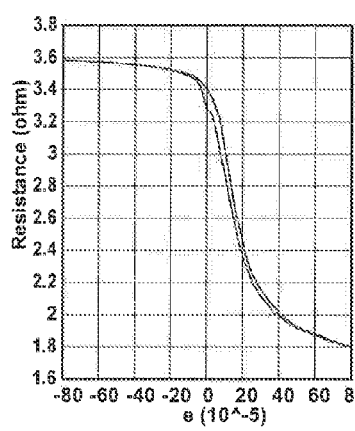 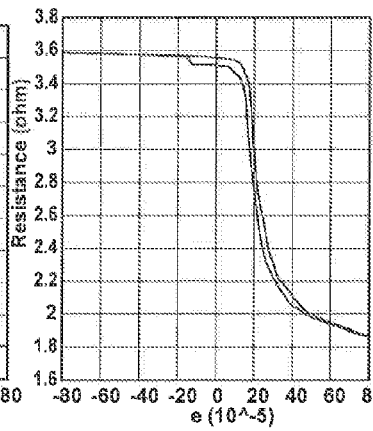 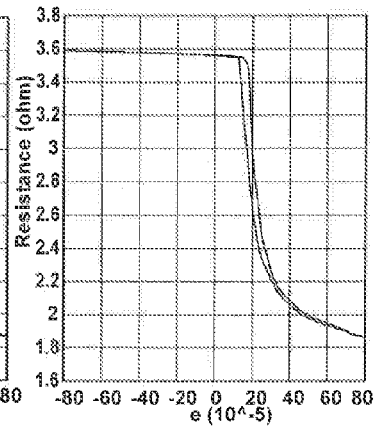
FIG. 27B     FIG. 27C     FIG. 27D

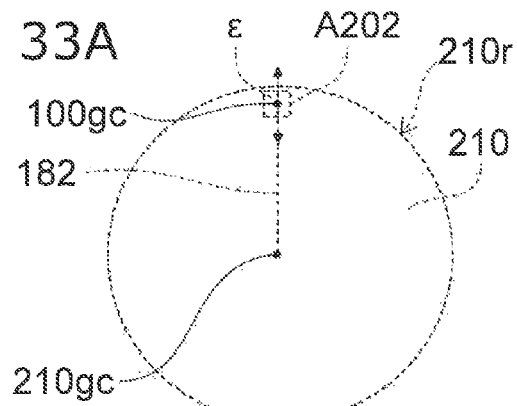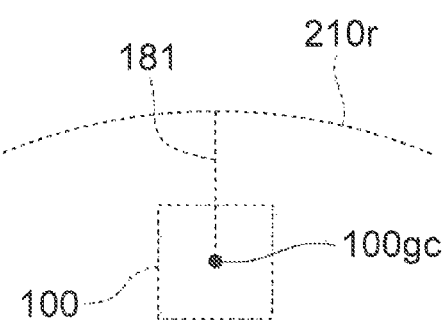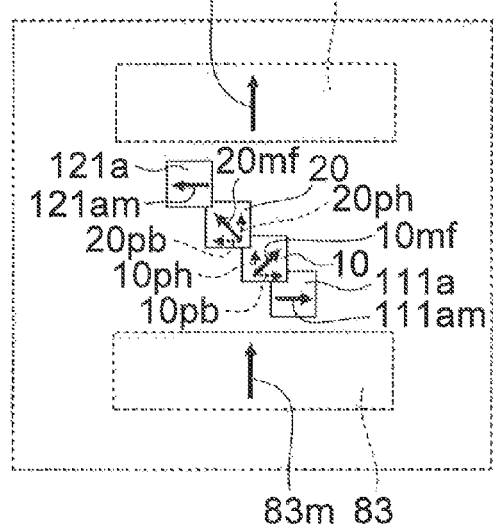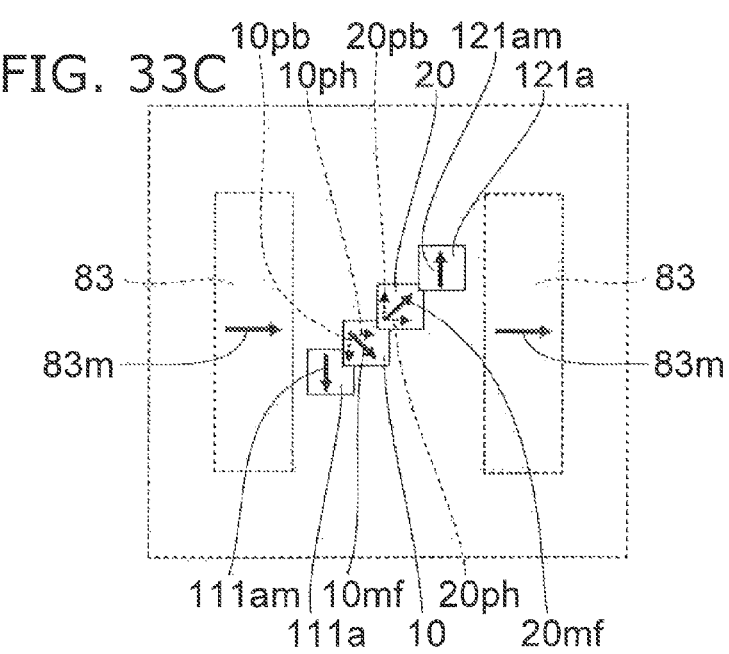

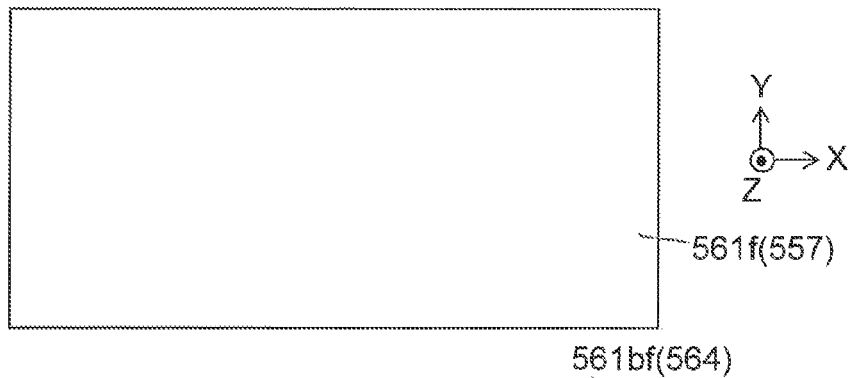
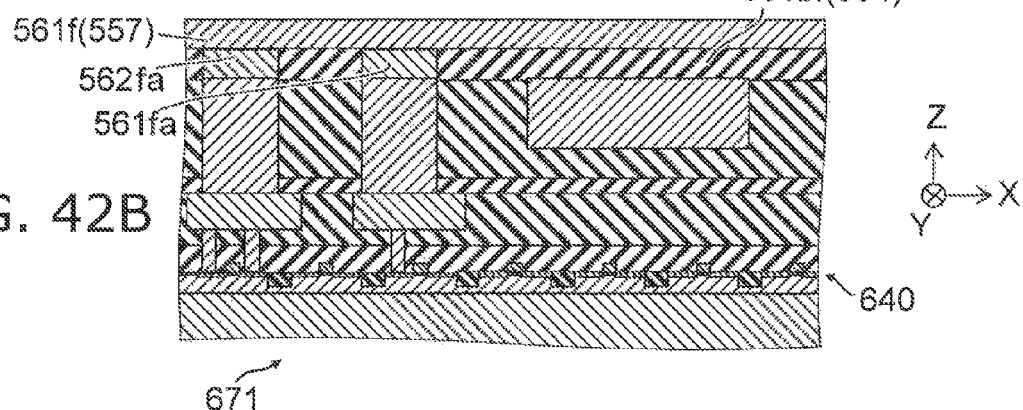
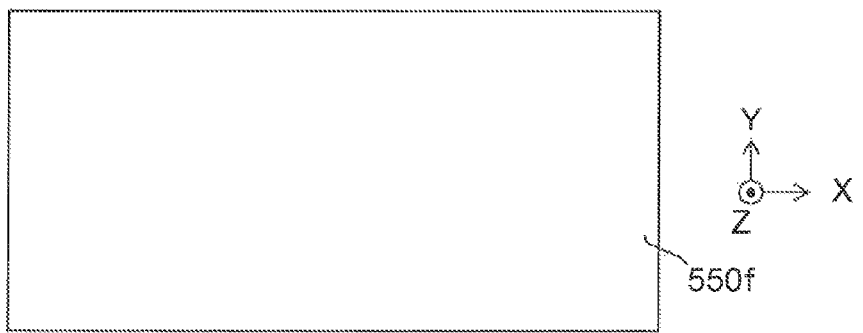
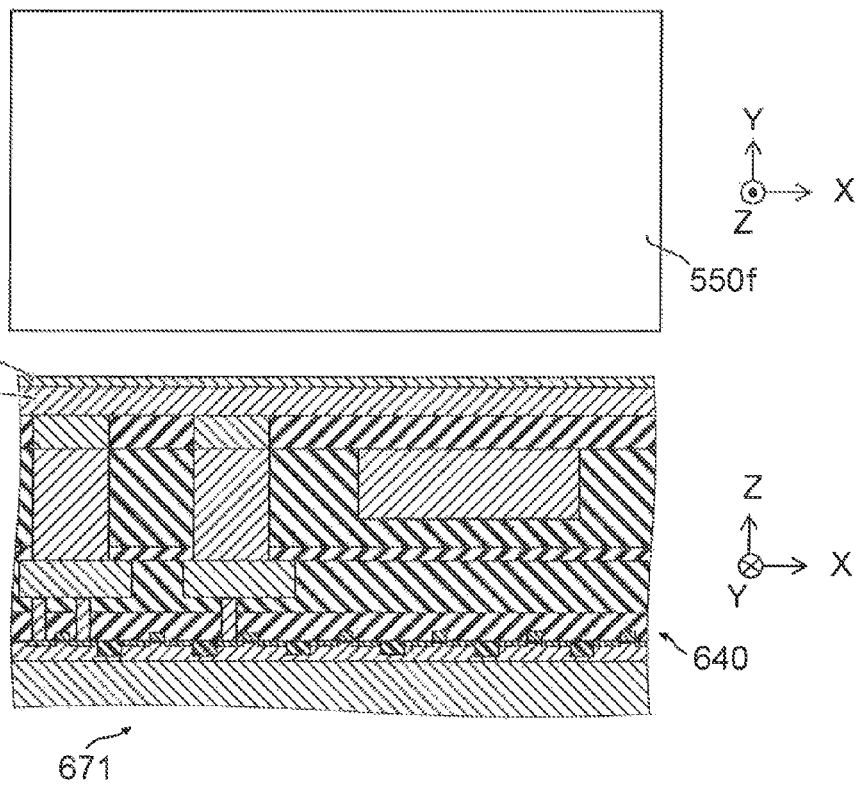

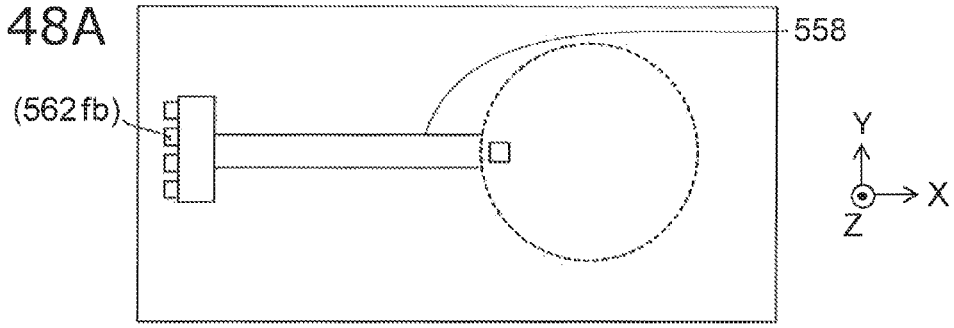
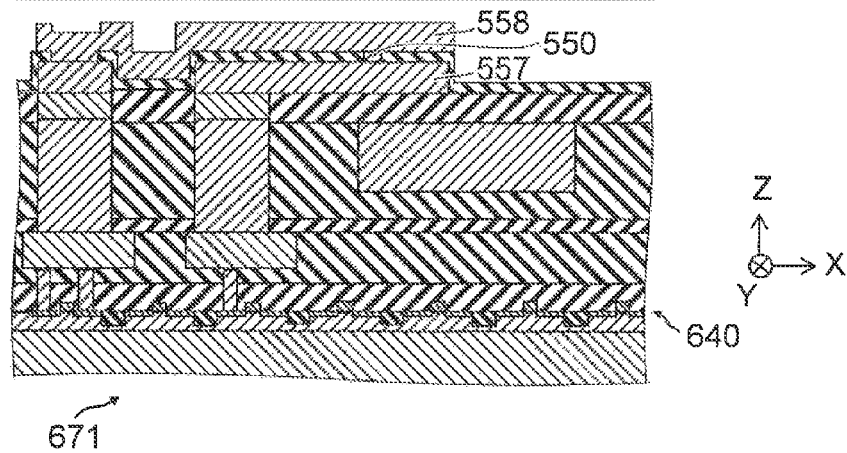
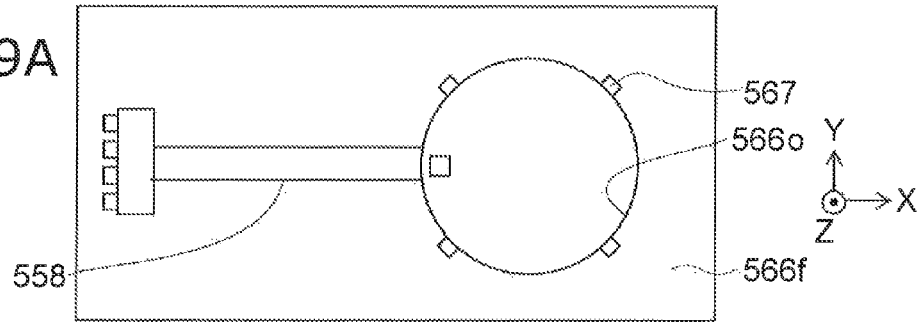
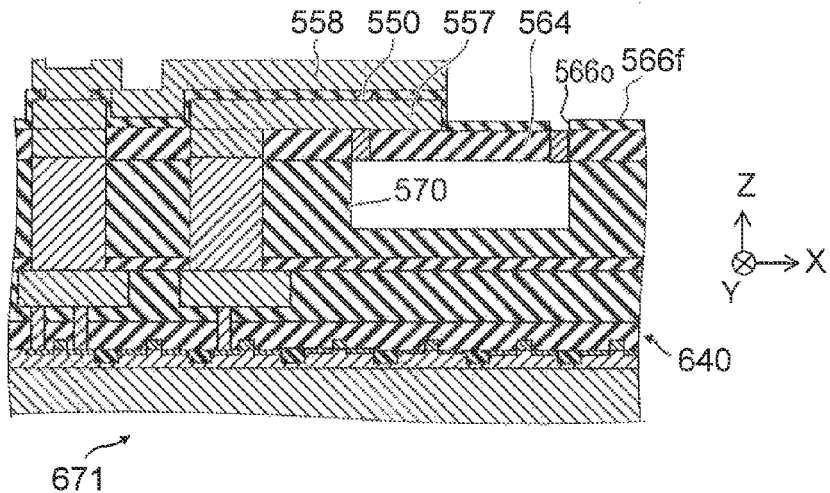

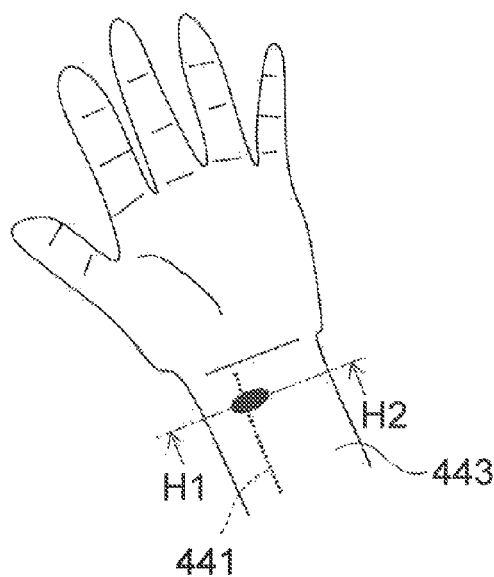
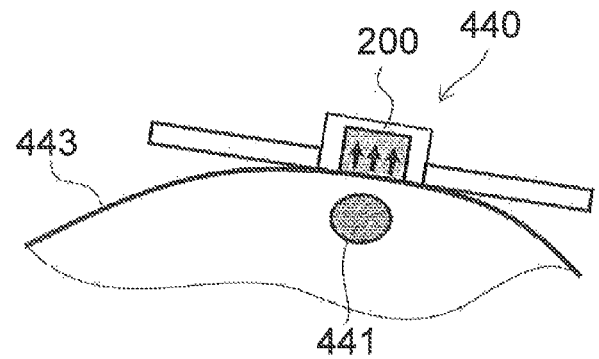
FIG. 52A    FIG. 52B
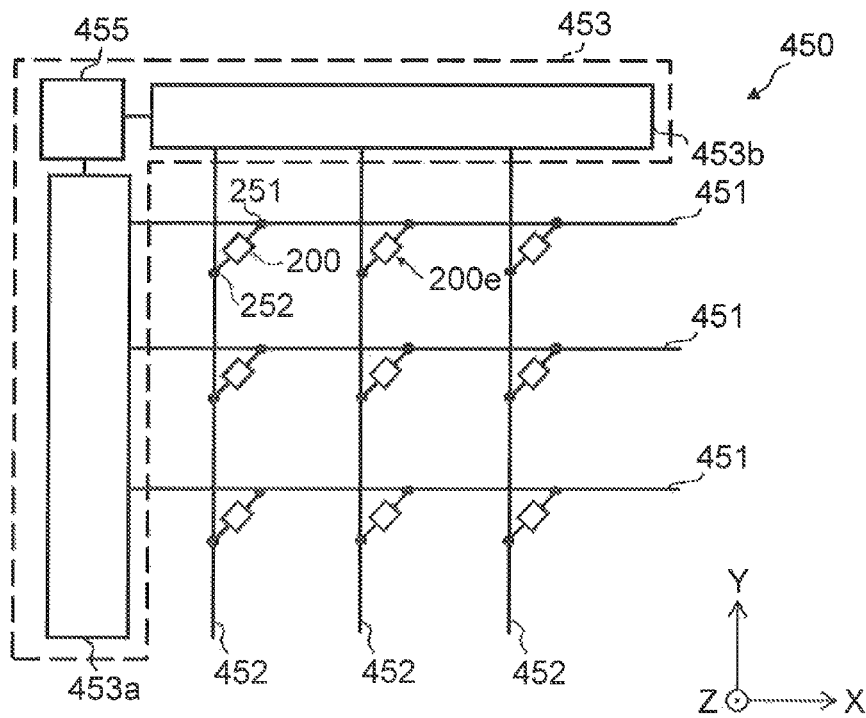
FIG. 53

STRAIN SENSING ELEMENT, PRESSURE SENSOR, MICROPHONE, BLOOD PRESSURE SENSOR, AND TOUCH PANEL

CROSS-REFERENCE TO RELATED APPLICATIONS

This application is based upon and claims the benefit of priority from Japanese Patent Application No. 2013-196243, filed on Sep. 20, 2013; the entire contents of which are incorporated herein by reference.

FIELD

Embodiments described herein relate generally to a strain sensing element, a pressure sensor, a microphone, a blood pressure sensor, and a touch panel.

BACKGROUND

A pressure sensor that uses a micro electro mechanical systems (MEMS) technology includes, for example, a piezoresistance change type and an electrostatic capacitance type. On the other hand, a pressure sensor that uses a spin-electronics technology has been proposed. In the pressure sensor using the spin-electronics technology, a resistance change corresponding to strain is sensed. For example, in a strain sensing element that is used in the pressure sensor or the like using the spin technology, it is desirable to enhance the sensitivity.

BRIEF DESCRIPTION OF THE DRAWINGS

FIGS. 1A and 1B are schematic diagrams illustrating a strain sensing element according to a first embodiment;

FIGS. 2A to 2C are schematic diagrams illustrating the operation of the strain sensing element according to the first embodiment;

FIGS. 14A to 14F are schematic diagrams illustrating in-plane angle dependency of free energy of a magnetization free layer of a comparative example;

FIGS. 24A and 24B are schematic perspective views illustrating the bias layers of the second embodiment;

FIGS. 25A to 25D are graphs illustrating examples of results of magnetic characteristics before the stacked body of the fifth example is element-processed;

FIGS. 26A to 26D are graphs illustrating examples of results of strain sensor characteristics of the strain sensing element of the fifth example;

FIGS. 27A to 27D are graphs illustrating examples of results of strain sensor characteristics of the strain sensing element of the sixth example;

FIGS. 33A to 33D are schematic plan views illustrating the relationship between the shape of the substrate and the direction of the bias layer of the second embodiment;

FIGS. 42A and 42B are schematic diagrams illustrating the method for manufacturing the pressure sensor according to the embodiment;

FIGS. 43A and 43B are schematic diagrams illustrating the method for manufacturing the pressure sensor according to the embodiment;

FIGS. 48A and 48B are schematic diagrams illustrating the method for manufacturing the pressure sensor according to the embodiment;

FIGS. 49A and 49B are schematic diagrams illustrating the method for manufacturing the pressure sensor according to the embodiment;

FIGS. 52A and 52B are schematic views illustrating a blood pressure sensor according to the sixth embodiment; and FIG. 53 is a schematic plan view illustrating a touch panel according to the seventh embodiment.

DETAILED DESCRIPTION

Figure 3:
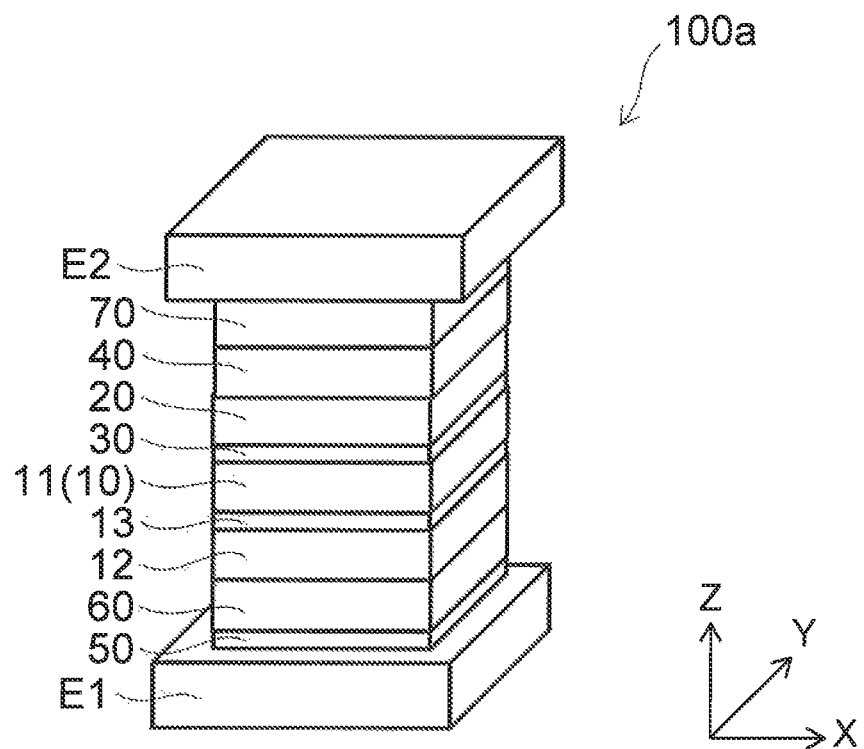
FIG. 3 is a schematic perspective view illustrating a strain sensing element according to the first embodiment.

In general, according to one embodiment, a strain sensing element provided on a deformable substrate includes: a first magnetic layer; a second magnetic layer; a spacer layer; and a bias layer. Magnetization of the second magnetic layer changes according to deformation of the substrate. The spacer layer is provided between the first magnetic layer and the second magnetic layer. The second magnetic layer is provided between the spacer layer and the bias layer. The bias layer is configured to apply a bias to the second magnetic layer.

Hereinafter, embodiments of the invention will be described with reference to the accompanying drawings.

The drawings are schematic or conceptual; and the relationship between the thickness and the width of each portion, the proportion of sizes between portions, or the like is not necessarily the same as in actual portions. Further, the dimensions and/or the proportions may be illustrated differently between the drawings, even for identical portions.

In the drawings and the specification of the application, components similar to those described in regard to a preceding drawing are marked with like reference numerals, and detailed description thereof is omitted as appropriate.

First Embodiment

FIGS. 1A and 1B are schematic diagrams illustrating a strain sensing element according to a first embodiment.

FIG. 1A is a schematic cross-sectional diagram illustrating a pressure sensor in which the strain sensing element is used. FIG. 1B is a schematic perspective view of the strain sensing element.

As illustrated in FIG. 1A, a strain sensing element 100 is used in a pressure sensor 200. The pressure sensor 200 includes a substrate 210 and the strain sensing element 100. The substrate 210 has a flexible region. The substrate 210 is deformable. The strain sensing element 100 is fixed to the substrate 210. In the specification, a fixed state includes a directly fixed state and an indirectly fixed state through a separate element. For example, a state where the strain sensing element 100 is fixed to the substrate 210 includes a state where a relative position between the strain sensing element 100 and the substrate 210 is fixed. The strain sensing element 100 is provided on a part of the substrate 210, for example.

In the specification, the "provided on" state includes a state where the strain sensing element 100 is provided in direct contact with the substrate 210 and a state where a separate element is interposed between the strain sensing element 100 and the substrate 210.

If a force 801 is applied to the substrate 210, the substrate 210 is deformed. Strain occurs in the strain sensing element 100 according to the deformation of the substrate 210.

In the strain sensing element 100 according to the embodiment, for example, if the substrate 210 is deformed due to an external force, strain occurs in the strain sensing element 100. The strain sensing element 100 converts a change of the strain into a change of an electrical resistance.

As illustrated in FIG. 1B, the strain sensing element 100 according to the embodiment includes a first magnetic layer 10, a second magnetic layer 20, a spacer layer 30, and a bias layer 40.

For example, a direction from the first magnetic layer 10 to the second magnetic layer 20 is taken as a Z-axis direction (a stacking direction). One direction perpendicular to the Z-axis direction is taken as an X-axis direction. A direction perpendicular to the Z-axis direction and the X-axis direction is taken as a Y-axis direction.

The bias layer 40 is provided separately from the first magnetic layer 10 in the stacking direction. The second magnetic layer 20 is provided between the first magnetic layer 10 and the bias layer 40. The spacer layer 30 is provided between the first magnetic layer 10 and the second magnetic layer 20. The bias layer 40 is in contact with the second magnetic layer 20.

The first magnetic layer 10 serves as a reference layer, for example. A magnetization pinned layer or a magnetization free layer is used as the reference layer.

The second magnetic layer 20 is a magnetization free layer, for example. If stress is applied to the strain sensing element 100 and thus strain occurs in the strain sensing element 100, the magnetization of the second magnetic layer 20 is changed. For example, the change of the magnetization of the second magnetic layer 20 occurs more easily than the change of the magnetization of the first magnetic layer 10. Thus, a relative angle between the magnetization of the first magnetic layer 10 and the magnetization of the second magnetic layer 20 is changed.

Next, an example of the operation of the strain sensing element 100 will be described.

FIGS. 2A to 2C are schematic diagrams illustrating the operation of the strain sensing element according to the first embodiment.

FIG. 2A corresponds to a state (a tensile state STt) when a tensile stress ts is applied to the strain sensing element 100. FIG. 2B corresponds to a state (a no-strain state ST0) when no strain is applied to the strain sensing element 100. FIG. 2C corresponds to a state (a compressive state STc) when a compressive stress cs is applied to the strain sensing element 100.

In FIGS. 2A to 2C, for ease of understanding, the first magnetic layer 10, the second magnetic layer 20 and the spacer layer 30 are shown, and the bias layer 40 is not shown. In the example, the second magnetic layer 20 is the magnetization free layer, and the first magnetic layer 10 is the magnetization pinned layer.

The operation of the strain sensing element 100 functioning as a strain sensor is based on an application of an "inverse-magnetostriction effect" and a "magnetoresistance effect". The "inverse-magnetostriction effect" is obtained in a ferromagnetic layer used in the magnetization free layer. The "magnetoresistance effect" occurs in a stacked film of the magnetization free layer, the spacer layer and the reference layer (for example, magnetization pinned layer).

The "inverse-magnetostriction effect" is a phenomenon in which the magnetization of a ferromagnetic material is changed by strain that occurs in the ferromagnetic material. In other words, when external strain is applied to the stacked body of the strain sensing element 100, the magnetization direction of the magnetization free layer changes. As a result, the relative angle between the magnetization of the magnetization free layer and the magnetization of the reference layer (for example, magnetization pinned layer) changes. Here, the change of the electrical resistance is caused by the "magnetoresistance effect (MR effect)". The MR effect includes, for example, a giant magnetoresistance (GMR) effect, a tunneling magnetoresistance (TMR) effect, or the like. As a current flows in the stacked body, the change of the relative angle of the magnetization direction is read as the change of the electrical resistance, so that the MR effect occurs. For example, strain occurs in the stacked body (the strain sensing element 100), and thus, the magnetization direction of the magnetization free layer is changed due to the strain. Thus, the relative angle between the magnetization direction of the magnetization free layer and the magnetization direction of the reference layer (for example, magnetization pinned layer) is changed. In other words, the MR effect occurs due to the inverse-magnetostriction effect.

In a case where the ferromagnetic material used in the magnetization free layer has a positive magnetostriction constant, the magnetization direction changes so that the angle between the magnetization direction and a tensile strain direction becomes small and the angle between the magnetization direction and a compressive strain direction becomes large. In a case where the ferromagnetic material used in the magnetization free layer has a negative magnetostriction constant, the magnetization direction changes so that the angle between the magnetization direction and the tensile strain direction becomes large and the angle between the magnetization direction and the compressive strain direction becomes small.

In a case where a combination of materials of the stacked body of the magnetization free layer, the spacer layer and the reference layer (for example, magnetization pinned layer) has a positive magnetoresistance effect, the electrical resistance becomes small in a case where the relative angle between the magnetization free layer and the magnetization pinned layer is small. In a case where the combination of materials of the stacked body of the magnetization free layer, the spacer layer and the reference layer (for example, magnetization pinned layer) has a negative magnetoresistance effect, the electrical resistance becomes large in a case where the relative angle between the magnetization free layer and the magnetization pinned layer is small.

Hereinafter, an example of a case where the ferromagnetic material used in the magnetization free layer has a positive magnetostriction constant and the stacked body including the magnetization free layer, the spacer layer and the reference layer (for example, magnetization pinned layer) has a positive magnetoresistance effect will be described with respect to an example of the change of the magnetization.

As illustrated in FIG. 2B, in the no-strain state ST0 (for example, an initial state) where strain does not occur, the relative angle between a magnetization 20m of the second magnetic layer 20 and a magnetization 10m of the first magnetic layer 10 (for example, magnetization pinned layer) is set to a predetermined value. The magnetization direction of the magnetic layer in the initial state is set by a hard bias, shape anisotropy of a magnetic layer or the like, for example. In the example, the magnetization 20m of the second magnetic layer 20 (magnetization free layer) and the magnetization 10m of the first magnetic layer 10 (for example, magnetization pinned layer) intersect with each other.

As illustrated in FIG. 2A, in the tensile state STt, if the tensile stress ts is applied, strain based on the tensile stress ts occurs in the strain sensing element 100. Here, the magnetization 20m of the second magnetic layer 20 (magnetization free layer) is changed from the no-strain state ST0 so that the angle between the magnetization 20m and the direction of the tensile stress ts becomes small. In the example illustrated in FIG. 2A, in a case where the tensile stress ts is applied, the relative angle between the magnetization 20m of the second magnetic layer 20 (magnetization free layer) and the magnetization 10m of the first magnetic layer 10 (for example, magnetization pinned layer) becomes small, compared with the no-strain state ST0. Thus, the electrical resistance in the strain sensing element 100 is reduced compared with the electrical resistance in the no-strain state ST0.

As illustrated in FIG. 2C, in the compressive state STc, if the compressive stress cs is applied, the magnetization 20m of the second magnetic layer 20 (magnetization free layer) is changed from the no-strain state ST0 so that the angle between the magnetization 20m and the direction of the compressive stress cs becomes large. In the example illustrated in FIG. 2C, in a case where the compressive stress cs is applied, the relative angle between the magnetization 20m of the second magnetic layer 20 (magnetization free layer) and the magnetization 10m of the first magnetic layer 10 (for example, magnetization pinned layer) becomes large, compared with the no-strain state ST0. Thus, the electrical resistance in the strain sensing element 100 is increased.

As described above, in the strain sensing element 100, the change of the strain that occurs in the strain sensing element 100 is converted into the change of the electrical resistance. In the above-described operation, a variation of electrical resistance (dR/R) per unit strain (dε) is referred to as a gauge factor (GF). It is possible to obtain a strain sensor of high sensitivity by using a strain sensing element having a high gauge factor.

As illustrated in FIG. 1B, in the strain sensing element 100 including the bias layer 40 provided in contact with the second magnetic layer 20 (magnetization free layer), it is possible to improve the anisotropy magnetic field of the second magnetic layer 20 (magnetization free layer) by magnetic coupling from the bias layer 40 to the second magnetic layer 20 (magnetization free layer) to an appropriate value. By improving the anisotropic magnetic field of the second magnetic layer 20 (magnetization free layer), it is possible to enhance reversibility of the change of the magnetization 20$m$ of the second magnetic layer 20 (magnetization free layer), and to obtain a high gauge factor. The enhancement of the reversibility of the change of the magnetization of the magnetization free layer with respect to strain will be described later in detail.

In a case where the size of the strain sensing element 100 becomes small, a diamagnetic field is generated inside the second magnetic layer 20 (magnetization free layer) due to the influence of a magnetic pole in an element end part of the second magnetic layer 20 (magnetization free layer), and thus, the magnetization 20$m$ may be disturbed. If the magnetization 20$m$ is disturbed, the change of the relative angle between the magnetization 10$m$ of the first magnetic layer 10 (for example, magnetization pinned layer) and the magnetization 20$m$ of the second magnetic layer 20 (magnetization free layer) due to the strain of the strain sensing element 100 may be reduced. The reduction of the diamagnetic field of the second magnetic layer 20 (magnetization free layer) is an important factor for providing a strain sensor of high sensitivity in the strain sensing element 100 having a relatively small size. The improvement of the anisotropic magnetic field of the second magnetic layer 20 (magnetization free layer) is also effective in reducing such an influence of the diamagnetic layer. Thus, it is possible to realize a high sensitivity of strain sensing in the strain sensing element 100 having the relatively small size. Further, it is possible to provide the strain sensing element 100 with high resolution and high sensitivity.

An example of the strain sensing element 100 according to the first embodiment will be described.

Hereinafter, "material A/material B" represents a state where a layer of the material B is provided on a layer of the material A.

FIG. 3 is a schematic perspective view illustrating a strain sensing element according to the first embodiment.

As illustrated in FIG. 3, a sensing element 100$a$ used in the embodiment includes a first electrode E1, an underlayer 50, a pinning layer 60, a second magnetization pinned layer 12, a magnetic coupling layer 13, a first magnetization pinned layer 11, the spacer layer 30, the second magnetic layer 20, the bias layer 40, a capping layer 70, and a second electrode E2. The magnetization pinned layer 11 corresponds to the first magnetic layer 10. The underlayer 50 is provided between the first electrode E1 and the second electrode E2. The pinning layer 60 is provided between the underlayer 50 and the second electrode E2. The second magnetization pinned layer 12 is provided between the pinning layer 60 and the second electrode E2. The magnetic coupling layer 13 is provided between the second magnetization pinned layer 12 and the second electrode E2. The first magnetization pinned layer 11 is provided between the magnetic coupling layer 13 and the second electrode E2. The spacer layer 30 is provided between the first magnetization pinned layer 11 and the second electrode E2. The second magnetic layer 20 is provided between the spacer layer 30 and the second electrode E2. The bias layer 40 is provided between the second magnetic layer 20 and the second electrode E2. The capping layer 70 is provided between the bias layer 40 and the second electrode E2.

The underlayer 50 includes, for example, Ta/Ru. The thickness of the Ta layer (length in the Z-axis direction) is, for example, 3 nm. The thickness of the Ru layer is, for example, 2 nm.

The pinning layer 60 includes, for example, an IrMn layer having a thickness of 7 nm.

The second magnetization pinned layer 12 includes, for example, a $Co_{75}Fe_{25}$ layer having a thickness of 2.5 nm.

The magnetic coupling layer 13 includes, for example, an Ru layer having a thickness of 0.9 nm.

The first magnetization pinned layer 11 includes, for example, a $Co_{40}Fe_{40}B_{20}$ layer having a thickness of 3 nm.

The spacer layer 30 includes, for example, an MgO layer having a thickness of 2.0 nm.

The second magnetic layer 20 includes, for example, $Co_{40}Fe_{40}B_{20}$ having a thickness of 4 nm.

The bias layer 40 includes, for example, Cu (5 nm)/$Fe_{50}Co_{50}$ (2 nm)/Ru (0.9 nm)/$Fe_{50}Co_{50}$ (2 nm)/IrMn (7 nm).

The capping layer 70 includes, for example, Ta/Ru. The thickness of the Ta layer is, for example, 1 nm. The thickness of the Ru layer is, for example, 5 nm.

The first electrode E1 and the second electrode E2 include, for example, at least one selected from aluminum (Al), an aluminum copper alloy (Al—Cu), copper (Cu), silver (Ag) and gold (Au). A current can be made to efficiently flow in the strain sensing element 100$a$ by using such a material that has a relatively small electrical resistance as the first electrode E1 and the second electrode E2. The first electrode E1 may include a non-magnetic material.

The first electrode E1 may include an underlayer (not shown) for the first electrode E1, a capping layer (not shown) for the first electrode E1, and a layer made of at least one selected from Al, Al—Cu, Cu, Ag and Au and provided between the underlayer (not shown) for the first electrode E1 and the capping layer (not shown) for the first electrode E1. For example, the first electrode E1 includes tantalum (Ta)/copper (Cu)/tantalum (Ta), or the like. For example, it is possible to improve adhesion between the substrate 210 and the first electrode E1 by using Ta as the underlayer for the first electrode E1. Titanium (Ti), titanium nitride (TiN) or the like may be used as the underlayer for the first electrode E1.

It is possible to prevent oxidization of the copper (Cu) or the like under the capping layer for the first electrode E1 by using Ta as the capping layer. Titanium (Ti), titanium nitride (TiN) or the like may be used as the capping layer for the first electrode E1.

The underlayer 50 may have a stacked structure of a buffer layer (not shown) and a seed layer (not shown). For example, the buffer layer reduces the irregularity of the surfaces of the first electrode E1 or the substrate 210, and improves the crystallinity of the layers stacked on the buffer layer. For example, at least one selected from the group consisting of tantalum (Ta), titanium (Ti), vanadium (V), tungsten (W), zirconium (Zr), hafnium (Hf) and chrome (Cr) is used as the buffer layer. An alloy including at least one material selected from these materials may be used as the buffer layer.

It is favorable that the thickness of the buffer layer in the underlayer 50 be 1 nm or more and 10 nm or less. It is more favorable that the thickness of the buffer layer be 1 nm or more and 5 nm or less. The buffering effect is lost when the thickness of the buffer layer is too thin. The thickness of the strain sensing element 100$a$ becomes excessively thick when the thickness of the buffer layer is too thick. The seed layer may be formed on the buffer layer, and the seed layer may have a buffering effect. In such a case, the buffer layer may be omitted. The buffer layer includes, for example, a Ta layer having a thickness of 3 nm.

The seed layer in the underlayer 50 controls the crystal orientation of the layers stacked on the seed layer. The seed layer controls the crystal grain size of the layers stacked on the seed layer. A metal or the like having a face-centered cubic (fcc) structure, a hexagonal close-packed (hcp) structure or a body-centered cubic (bcc) structure is used as the seed layer.

By using ruthenium (Ru) having an hcp structure, NiFe having an fcc structure, or Cu having an fcc structure as the seed layer in the underlayer 50, for example, the crystal orientation of the spin-valve film on the seed layer can have an fcc (111) orientation. The seed layer includes, for example, a Cu layer having a thickness of 2 nm or a Ru layer having a thickness of 2 nm. To improve the crystal orientation of the layers formed on the seed layer, it is favorable that the thickness of the seed layer be 1 nm or more and 5 nm or less. It is more favorable that the thickness of the seed layer be 1 nm or more and 3 nm or less. Thus, the function of the seed layer of improving the crystal orientation is sufficiently realized.

On the other hand, for example, in a case where it is unnecessary to cause the layers formed on the seed layer to have a crystal orientation (for example, in a case where an amorphous magnetization free layer is formed), the seed layer may be omitted. For example, a Cu layer having a thickness of 2 nm is used as the seed layer.

The pinning layer 60 provides unidirectional anisotropy to the second magnetization pinned layer 12 (ferromagnetic layer) formed on the pinning layer 60, for example, to fix the magnetization of the second magnetization pinned layer 12. The pinning layer 60 includes, for example, an antiferromagnetic layer. The pinning layer 60 includes, for example, at least one selected from the group consisting of IrMn, PtMn, PdPtMn and RuRhMn. The thickness of the pinning layer 60 is set appropriately to provide unidirectional anisotropy of sufficient strength.

When PtMn or PdPtMn is used as the pinning layer 60, it is favorable that the thickness of the pinning layer 60 be 8 nm or more and 20 nm or less. It is more favorable that the thickness of the pinning layer 60 be 10 nm or more and 15 nm or less. In a case where IrMn is used as the pinning layer 60, it is possible to provide the unidirectional anisotropy with a small thickness, compared with a case where PtMn is used as the pinning layer 60. In such a case, it is favorable that the thickness of the pinning layer 60 be 4 nm or more and 18 nm or less. It is more favorable that the thickness of the pinning layer 60 be 5 nm or more and 15 nm or less. The pinning layer 60 includes, for example, an $Ir_{22}Mn_{78}$ layer having a thickness of 7 nm.

A hard magnetic layer may be used as the pinning layer 60. As the hard magnetic layer, for example, CoPt (the ratio of Co is 50 at. % or more and 85 at. % or less), $(Co_xPt_{100-x})_{100-y}Cr_y$ (x being 50 at. % or more and 85 at. % or less and y being 0 at. % or more and 40 at. % or less), FePt (the ratio of Pt is 40 at. % or more and 60 at. % or less), or the like may be used.

The second magnetization pinned layer 12 includes, for example, a $Co_xFe_{100-x}$ alloy (x being 0 at. % or more and 100 at. % or less), an $Ni_xFe_{100-x}$ alloy (x being 0 at. % or more and 100 at. % or less), or a material in which a non-magnetic element is added to these alloys. For example, at least one selected from the group consisting of Co, Fe and Ni may be used as the second magnetization pinned layer 12. An alloy including at least one material selected from these materials may be used as the second magnetization pinned layer 12. As the second magnetization pinned layer 12, an amorphous alloy of $(Co_xFe_{100-x})_{100-y}B_y$ (x being 0 at. % or more and 100 at. % or less and y being 0 at. % or more and 30 at. % or less) may be also used. By using the amorphous alloy of $(Co_xFe_{100-x})_{100-y}B_y$ as the second magnetization pinned layer 12, it is possible to suppress the fluctuation in characteristics of the strain sensing element 100a even in a case where the size of the strain sensing element 100a is small.

It is favorable that the thickness of the second magnetization pinned layer 12 be, for example, 1.5 nm or more and 5 nm or less. Thus, for example, it is possible to increase the strength of the unidirectional anisotropic magnetic field due to the pinning layer 60. For example, it is possible to increase the strength of the antiferromagnetic coupling magnetic field between the second magnetization pinned layer 12 and the first magnetization pinned layer 11 through the magnetic coupling layer 13 formed on the second magnetization pinned layer 12. It is favorable that the magnetic film thickness of the second magnetization pinned layer 12 (the product of a saturation magnetization Bs and a thickness t (Bs·t)) be substantially equal to the magnetic film thickness of the first magnetization pinned layer 11.

In a thin film, the saturation magnetization of $Co_{40}Fe_{40}B_{20}$ is about 1.9 T (teslas). For example, in a case where a $Co_{40}Fe_{40}B_{20}$ layer having a thickness of 3 nm is used as the first magnetization pinned layer 11, the magnetic film thickness of the first magnetization pinned layer 11 is 1.9 T×3 nm, which is 5.7 Tnm. On the other hand, the saturation magnetization of $Co_{75}Fe_{25}$ is about 2.1 T. The thickness of the second magnetization pinned layer 12 for obtaining a magnetic film thickness that is equal to the above-mentioned magnetic film thickness is 5.7 Tnm/2.1 T, which is 2.7 nm. In such a case, it is favorable that the second magnetization pinned layer 12 includes a $Co_{75}Fe_{25}$ layer having a thickness of about 2.7 nm. For example, a $Co_{75}Fe_{25}$ layer having a thickness of 2.5 nm may be used as the second magnetization pinned layer 12.

In the strain sensing element 100a, a synthetic pinned structure of the second magnetization pinned layer 12, the magnetic coupling layer 13 and the first magnetization pinned layer 11 is used. Instead, a single pinned structure made of one magnetization pinned layer may be used. In a case where the single pinned structure is used, for example, a $Co_{40}Fe_{40}B_{20}$ layer having a thickness of 3 nm is used as the magnetization pinned layer. As the ferromagnetic layer used in the magnetization pinned layer of the single pinned structure, the same material as the material of the above-described second magnetization pinned layer 12 may be used.

The magnetic coupling layer 13 causes antiferromagnetic coupling to occur between the second magnetization pinned layer 12 and the first magnetization pinned layer 11. The magnetic coupling layer 13 forms a synthetic pinned structure. For example, Ru is used as the magnetic coupling layer 13. It is favorable that the thickness of the magnetic coupling layer 13 be 0.8 nm or more and 1 nm or less. A material other than Ru may be used as the magnetic coupling layer 13 as long as the material can cause sufficient antiferromagnetic coupling to occur between the second magnetization pinned layer 12 and the first magnetization pinned layer 11. The thickness of the magnetic coupling layer 13 may be set to be a thickness of 0.8 nm or more and 1 nm or less that corresponds to the second peak (2nd peak) of Ruderman-Kittel-Kasuya-Yosida (RKKY) coupling. Further, the thickness of the magnetic coupling layer 13 may be set to be a thickness of 0.3 nm or more and 0.6 nm or less that corresponds to the first peak (1st peak) of RKKY coupling. For example, Ru having a thickness of 0.9 nm is used as the magnetic coupling layer 13. Thus, highly reliable coupling is obtained more stably.

The magnetic layer that is used in the first magnetization pinned layer 11 contributes directly to the MR effect. For example, a Co—Fe—B alloy is used as the first magnetization pinned layer 11. Specifically, a $(Co_xFe_{100-x})_{100-y}B_y$ alloy (x being 0 at. % or more and 100 at % or less and y being 0 at. % or more and 30 at. % or less) may be used as the first magnetization pinned layer 11. In a case where an amorphous alloy of $(Co_xFe_{100-x})_{100-y}B_y$ is used as the first magnetization pinned layer 11, for example, it is possible to suppress the fluctuation between the elements due to the crystal grains even in a case where the size of the strain sensing element 100a is small.

The layer (for example, a tunneling insulating layer (not shown)) that is formed on the first magnetization pinned layer 11 may be planarized. By planarizing the tunneling insulating layer, it is possible to reduce the defect density of the tunneling insulating layer. Thus, a higher MR ratio is obtained with a lower resistance per area. For example, in a case where MgO is used as a material of the tunneling insulating layer, it is possible to improve the (100) orientation of the MgO layer formed on the tunneling insulating layer by using an amorphous alloy of $(Co_xFe_{100-x})_{100-y}B_y$. A higher MR ratio is obtained by improving the (100) orientation of the MgO layer. The $(Co_xFe_{100-x})_{100-y}B_y$ alloy is crystallized using the (100) plane of the MgO layer as a template in the annealing. Therefore, excellent crystal conformation between the MgO and $(Co_xFe_{100-x})_{100-y}B_y$ alloy is obtained. A higher MR ratio is obtained by obtaining excellent crystal conformation.

Instead of the Co—Fe—B alloy, for example, an Fe—Co alloy may be used as the first magnetization pinned layer 11.

The MR ratio increases as the thickness of the first magnetization pinned layer 11 increases. A thinner first magnetization pinned layer 11 is favorable for obtaining a larger fixed magnetization field. A trade-off relationship in the thickness of the first magnetization pinned layer 11 exists between the MR ratio and the fixed magnetic field. In a case where the Co—Fe—B alloy is used as the first magnetization pinned layer 11, it is favorable that the thickness of the first magnetization pinned layer 11 be 1.5 nm or more and 5 nm or less. It is more favorable that the thickness of the first magnetization pinned layer 11 be 2.0 nm or more and 4 nm or less.

Instead of the materials described above, the first magnetization pinned layer 11 may include a $Co_{90}Fe_{10}$ alloy having an fcc structure, Co having an hcp structure, or a Co alloy having an hcp structure. At least one selected from the group consisting of Co, Fe, and Ni may be used as the first magnetization pinned layer 11. An alloy including at least one material selected from these materials may be used as the first magnetization pinned layer 11. For example, a higher MR ratio is obtained by using an FeCo alloy material having a bcc structure, a Co alloy including a cobalt composition of 50 at. % or more, or a material having a Ni composition of 50 at. % or more (Ni alloy) as the first magnetization pinned layer 11.

A Heusler magnetic alloy layer made of $Co_2MnGe$, $Co_2FeGe$, $Co_2MnSi$, $Co_2FeSi$, $Co_2MnAl$, $Co_2FeAl$, $Co_2MnGa_{0.5}Ge_{0.5}$, $Co_2FeGa_{0.5}Ge_{0.5}$, and the like may be used as the first magnetization pinned layer 11. For example, a $Co_{40}Fe_{40}B_{20}$ layer having a thickness of 3 nm may be used as the first magnetization pinned layer 11.

The spacer layer 30 disconnects the magnetic coupling between the first magnetic layer 10 and the second magnetic layer 20. The spacer layer 30 includes, for example, a metal, an insulator or a semiconductor. For example, Cu, Au, Ag or the like may be used as the metal. In a case where the metal is used as the spacer layer 30, the thickness of the spacer layer 30 is, for example, about 1 nm or more and about 7 nm or less. For example, magnesium oxide (Mg—O, etc.), aluminum oxide ($Al_2O_3$, etc.), titanium oxide (Ti—O, etc.), zinc oxide (Zn—O, etc.), gallium oxide (Ga—O), or the like may be used as the insulator or the semiconductor. In a case where the insulator or the semiconductor is used as the spacer layer 30, the thickness of the spacer layer 30 is, for example, about 0.6 nm or more and about 2.5 nm or less. For example, a CCP (Current-Confined-Path) spacer layer may be used as the spacer layer 30. In a case where the CCP spacer layer is used as the spacer layer, for example, a structure in which copper (Cu) metal paths are formed in an insulating layer of aluminum oxide ($Al_2O_3$) is used. For example, an MgO layer having a thickness of 1.6 nm is used as the spacer layer 30.

The second magnetic layer 20 includes a ferromagnetic material. The second magnetic layer 20 may include, for example, a ferromagnetic material including Fe, Co and Ni. For example, an FeCo alloy, a NiFe alloy, or the like may be used as the material of the second magnetic layer 20. Further, the second magnetic layer 20 may include a Co—Fe—B alloy, an Fe—Co—Si—B alloy, an Fe—Ga alloy having a large λs (magnetostriction constant), an Fe—Co—Ga alloy, a Tb-M-Fe alloy, a Tb-M1-Fe-M2 alloy, an Fe-M3-M4-B alloy, Ni, Fe—Al, ferrite, or the like. In the above-mentioned Tb-M-Fe alloy, M is at least one selected from the group consisting of Sm, Eu, Gd, Dy, Ho, and Er. In the above-mentioned Tb-M1-Fe-M2 alloy, M1 is at least one selected from the group consisting of Sm, Eu, Gd, Dy, Ho and Er. Further, M2 is at least one selected from the group consisting of Ti, Cr, Mn, Co, Cu, Nb, Mo, W and Ta. In the above-mentioned F3-M3-M4-B alloy, M3 is at least one selected from the group consisting of Ti, Cr, Mn, Co, Cu, Nb, Mo, W and Ta. Further, M4 is at least one selected from the group consisting of Ce, Pr, Nd, Sm, Tb, Dy and Er. $Fe_3O_4$, $(FeCo)_3O_4$, or the like may be used as the above-mentioned ferrite. The thickness of the second magnetic layer 20 is, for example, 2 nm or more.

The second magnetic layer 20 may include a magnetic material containing boron. The second magnetic layer 20 may include, for example, an alloy including at least one element selected from the group consisting of Fe, Co and Ni, and boron (B). For example, a Co—Fe—B alloy or an Fe—B alloy may be used. For example, a $Co_{40}Fe_{40}B_{20}$ alloy may be used. In a case where the second magnetic layer 20 includes the alloy including at least one element selected from the group consisting of Fe, Co and Ni, and boron (B), Ga, Al, Si, W or the like may be additionally used as an element that promotes high magnetostriction. For example, an Fe—Ga—B alloy, an Fe—Co—Ga—B alloy or an Fe—Co—Si—B alloy may be used. By using such a magnetic material containing boron, a coercivity ($H_c$) of the second magnetic layer 20 becomes low, and the change of the magnetization 20m with respect to strain becomes simple. Thus, it is possible to obtain a high strain sensitivity.

It is favorable that the boron concentration (for example, the composition ratio of boron) in the second magnetic layer 20 be 5 at. % (atomic percent) or more. Thus, an amorphous structure is easily obtained. It is favorable that the boron concentration in the second magnetic layer 20 be 35 at. % or less. If the boron concentration is too high, for example, the magnetostriction constant is reduced. It is favorable that the boron concentration in the second magnetic layer 20 be 5 at. % or more and 35 at. % or less, and it is more favorable that the boron concentration in the second magnetic layer 20 be 10 at % or more and 30 at. % or less.

In a case where a part of the magnetic layer of the second magnetic layer 20 includes $Fe_{1-y}B_y$ ($0<y\leq 0.3$) or $(Fe_aX_{1-a})_{1-y}B_y$ (X=Co or Ni, $0.8\leq a<1$, $0<y\leq 0.3$), it is easy to achieve both of a large magnetostriction constant A and a low coercivity, and thus, this case is particularly favorable in view of obtaining a high gauge factor. For example, $Fe_{80}B_{20}$ (4 nm) may be used as the second magnetic layer 20. $Co_{40}Fe_{40}B_{20}$ (0.5 nm)/$Fe_{80}B_{20}$ (4 nm) may be used as the second magnetic layer 20.

The second magnetic layer 20 may have a multilayered structure. In a case where a tunneling insulating layer of MgO is used as the spacer layer 30, it is favorable that a layer of a Co—Fe—B alloy be provided at a portion of the second magnetic layer 20 that contacts with the spacer layer 30. Thus, a high magnetoresistance effect is obtained. In such a case, the layer of the Co—Fe—B alloy may be provided on the spacer layer 30, and another magnetic material having a large magnetostriction constant is provided on the layer of the Co—Fe—B alloy. In a case where the second magnetic layer 20 has the multilayered structure, the second magnetic layer 20 includes, for example, Co—Fe—B (2 nm)/Fe—Co—Si—B (4 nm) or the like.

In the embodiment, the bias layer 40 is provided on the second magnetic layer 20. The bias layer 40 will be described later in detail.

The capping layer 70 protects the layers provided under the capping layer 70. The capping layer 70 includes, for example, plural metal layers. The capping layer 70 includes, for example, a two-layer structure of a Ta layer and a Ru layer (Ta/Ru). The thickness of the Ta layer is, for example, 1 nm, and the thickness of the Ru layer is, for example, 5 nm. Other metal layers may be provided instead of the Ta layer or the Ru layer as the capping layer 70. The configuration of the capping layer 70 is arbitrary. The capping layer 70 may include, for example, a non-magnetic material. Other materials may be used as the capping layer 70 as long as the layers provided under the capping layer 70 can be protected.

FIGS. 4A to 4E are schematic perspective views illustrating the bias layer of the first embodiment.

FIGS. 4A to 4E illustrate examples of variations of the structure of the bias layer 40 where the second magnetic layer 20 is provided between the spacer layer 30 and the bias layer 40, which is provided with respect to the stacked body of the first magnetic layer 10 (reference layer)/the spacer layer 30/the second magnetic layer 20 (magnetization free layer). In these examples, the first magnetic layer 10 corresponds to the first magnetization pinned layer 11.

Figure 4A:
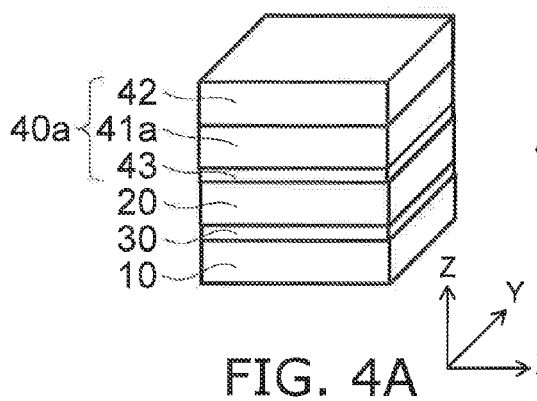
FIGS. 4A to 4E are schematic perspective views illustrating the bias layer of the first embodiment.

A bias layer 40a illustrated in FIG. 4A includes a first bias magnetic layer 41a, a bias pinning layer 42, and a separating layer 43. The separating layer 43 is provided between the second magnetic layer 20 and the bias pinning layer 42. The first bias magnetic layer 41a is provided between the separating layer 43 and the bias pinning layer 42.

The first bias magnetic layer 41a is formed of a magnetic material, for example. Magnetization of the first bias magnetic layer 41a is fixed in one direction by the bias pinning layer 42. The first bias magnetic layer 41a in which the magnetization is fixed in one direction applies a bias to the second magnetic layer 20 by magnetic coupling such as exchange coupling. The separating layer 43 is formed of a non-magnetic material or the like. The separating layer 43 physically separates the first bias magnetic layer 41a from the second magnetic layer 20, to adjust the strength of the magnetic coupling between the first bias magnetic layer 41a and the second magnetic layer 20. It may not be necessary to provide the separating layer 43 according to the material of the first bias magnetic layer 41a.

The separating layer 43 includes, for example, Cu of 5 nm. The first bias magnetic layer 41a includes, for example, $Fe_{50}Co_{50}$ of 3 nm. The pinning layer 42 includes, for example, IrMn of 7 nm.

The first bias magnetic layer 41a may include, for example, at least one selected from the group consisting of Co, Fe and Ni. An alloy including at least one material selected from the group consisting of Co, Fe and Ni may be used as the first bias magnetic layer 41a. For example, the first bias magnetic layer 41a includes, for example, a $Co_xFe_{100-x}$ alloy (x being 0 at. % or more and 100 at. % or less), an $Ni_xFe_{100-x}$ alloy (x being 0 at. % or more and 100 at. % or less), or a material in which a non-magnetic element is added to these alloys. As the first bias magnetic layer 41a, a $(Co_xFe_{100-x})_{100-y}B_y$ alloy (x being 0 at. % or more and 100 at. % or less and y being 0 at. % or more and 30 at. % or less) may be also used. By using an amorphous alloy of $(Co_xFe_{100-x})_{100-y}B_y$ as the first bias magnetic layer 41a, it is possible to suppress the fluctuation between the strain sensing elements 100a even in a case where the size of the strain sensing element 100a is small. It is favorable that the thickness of the first bias magnetic layer 41a be, for example, 1.5 nm or more and 5 nm or less. Thus, for example, it is possible to sufficiently increase the strength of the unidirectional anisotropic magnetic field due to the bias pinning layer 42. For example, $Fe_{50}Co_{50}$ of 3 nm may be used as the first bias magnetic layer 41a.

The separating layer 43 includes, for example, a non-magnetic material. The separating layer 43 may use a layer including at least one element selected from the group consisting of Cu, Ru, Rh, Ir, V, Cr, Nb, Mo, Ta, W, Rr, Au, Ag, Pt, Pd, Ti, Zr, and Hf. For example, Cu of 5 nm is used as the separating layer 43.

The bias pinning layer 42 provides unidirectional anisotropy to the first bias magnetic layer 41a formed in contact with the bias pinning layer 42 to fix the magnetization of the first bias magnetic layer 41a. The bias pinning layer 42 includes, for example, an antiferromagnetic layer. The bias pinning layer 42 includes, for example, at least one selected from the group consisting of Ir—Mn, Pt—Mn, Pd—Pt—Mn and Ru—Rh—Mn. The thickness of the bias pinning layer 42 is set appropriately to provide unidirectional anisotropy of sufficient strength.

When Pt—Mn or Pd—Pt—Mn is used as the bias pinning layer 42, it is favorable that the thickness of the bias pinning layer 42 be 8 nm or more and 20 nm or less. It is more favorable that the thickness of the bias pinning layer 42 be 10 nm or more and 15 nm or less. In a case where IrMn is used as the bias pinning layer 42, it is possible to provide the directional anisotropy to the first bias magnetic layer 41a with the bias pinning layer 42 having a small thickness, compared with a case where PtMn is used as the bias pinning layer 42. In such a case, it is favorable that the thickness of the bias pinning layer 42 be 4 nm or more and 18 nm or less. It is more favorable that the thickness of the bias pinning layer 42 be 5 nm or more and 15 nm or less. The bias pinning layer 42 includes, for example, an $Ir_{22}Mn_{78}$ layer having a thickness of 7 nm.

A hard magnetic layer may be used as the bias pinning layer 42. As the hard magnetic layer, for example, CoPt (the ratio of Co is 50 at. % or more and 85 at. % or less), $(Co_xPt_{100-x})_{100-y}Cr_y$ (x being 50 at. % or more and 85 at. % or less and y being 0 at. % or more and 40 at. % or less), FePt (the ratio of Pt is 40 at. % or more and 60 at. % or less), or the like may be used.

Figure 4D:
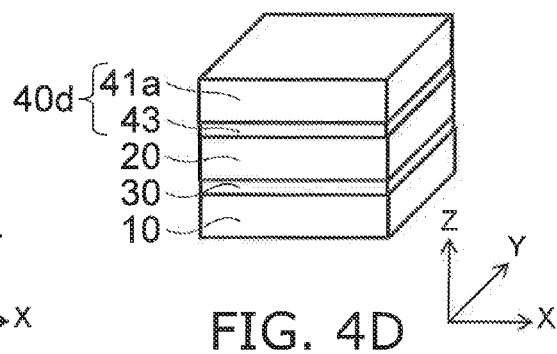
Figure 4B:
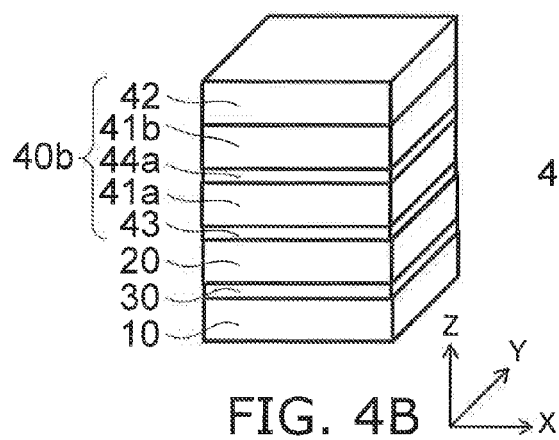

FIG. 4B is a schematic perspective view illustrating another bias layer of the first embodiment.

A bias layer 40b illustrated in FIG. 4B includes a first bias magnetic layer 41a, a second bias magnetic layer 41b, a bias pinning layer 42, a separating layer 43, and a first magnetic coupling layer 44a. The separating layer 43 is provided between the second magnetic layer 20 and the bias pinning layer 42. The first bias magnetic layer 41a is provided between the separating layer 43 and the bias pinning layer 42. The first magnetic coupling layer 44a is provided between the first bias magnetic layer 41a and the bias pinning layer 42. The second bias magnetic layer 41b is provided between the first magnetic coupling layer 44a and the bias pinning layer 42.

In the bias layer 40a illustrated in FIG. 4A, a bias magnetic layer of a single-layer structure (the first bias magnetic layer 41a) is provided. On the other hand, in the bias layer 40b illustrated in FIG. 4B, bias magnetic layers of a double-layer structure (the first bias magnetic layer 41a and the second bias magnetic layer 41b) are provided through the first magnetic coupling layer 44a. In this point, the bias layer 40b in FIG. 4B is different from the bias layer 40a in FIG. 4A.

The magnetization of the first bias magnetic layer 41a is set to be opposite to the magnetization of the adjacent second bias magnetic layer 41b through the first magnetic coupling layer 44a. By setting the magnetizations of the plural bias magnetic layers to be anti-parallel (180°), it is possible to suppress the stray magnetic field from the bias magnetic layers to the outside, and to suppress magnetic interference other than exchange coupling bias to the second magnetic layer 20. It may not be necessary to provide the separating layer 43.

The first magnetic coupling layer 44a causes antiferromagnetic coupling to occur between the first bias magnetic layer 41a and the second bias magnetic layer 41b. The first magnetic coupling layer 44a forms a synthetic pinned structure. For example, Ru is used as the first magnetic coupling layer 44a. It is favorable that the thickness of the first magnetic coupling layer 44a be 0.8 nm or more and 1 nm or less. A material other than Ru may be used as the first magnetic coupling layer 44a as long as the material can cause sufficient antiferromagnetic coupling to occur between the first bias magnetic layer 41a and the second bias magnetic layer 41b. The thickness of the first magnetic coupling layer 44a may be set to be a thickness of 0.8 nm or more and 1 nm or less that corresponds to the second peak (2nd peak) of Ruderman-Kittel-Kasuya-Yosida (RKKY) coupling. Further, the thickness of the first magnetic coupling layer 44a may be set to be a thickness of 0.3 nm or more and 0.6 nm or less that corresponds to the first peak (1st peak) of RKKY coupling. For example, Ru having a thickness of 0.9 nm is used as the first magnetic coupling layer 44a. Thus, highly reliable coupling is obtained more stably.

It is favorable that the thickness of the first bias magnetic layer 41a be, for example, 1.5 nm or more and 5 nm or less. It is favorable that the thickness of the second bias magnetic layer 41b be, for example, 1.5 nm or more and 5 nm or less. Thus, for example, it is possible to increase the strength of the unidirectional anisotropic magnetic field due to the bias pinning layer 42. It is favorable that the magnetic film thickness of the first bias magnetic layer 41a (the product of a saturation magnetization Bs and a thickness t (Bs·t)) be substantially equal to the magnetic film thickness of the second bias magnetic layer 41b.

In a case where the same magnetic material is used in the first bias magnetic layer 41a and the second bias magnetic layer 41b, it is favorable to match the thickness of the first bias magnetic layer 41a with the thickness of the second bias magnetic layer 41b. In a case where different magnetic layers are used in the first bias magnetic layer 41a and the second bias magnetic layer 41b, for example, in a case where $Co_{40}Fe_{40}B_{20}$ is used in the first bias magnetic layer 41a and $Co_{75}Fe_{25}$ is used in the second bias magnetic layer 41b, in a thin film, the saturation magnetization of $Co_{40}Fe_{40}B_{20}$ is about 1.9 T (teslas), and the saturation magnetization of $Co_{75}Fe_{25}$ is about 2.1 T. For example, in a case where a $Co_{40}Fe_{40}B_{20}$ layer having a thickness of 3 nm is used as the first bias magnetic layer 41a, the magnetic film thickness of the first bias magnetic layer 41a is 1.9 T×3 nm, which is 5.7 Tnm. The thickness of the second bias magnetic layer 41b to obtain a magnetic film thickness that is equal to the above-mentioned magnetic film thickness is 5.7 Tnm/2.1 T, which is 2.7 nm. In such a case, it is favorable that the second bias magnetic layer 41b includes a $Co_{75}Fe_{25}$ layer having a thickness of about 2.7 nm.

As materials of the respective layers included in the bias layer 40b illustrated in FIG. 4B, the same materials as the materials of the respective layers included in the bias layer 40a illustrated in FIG. 4A may be respectively used.

The separating layer 43 includes, for example, Cu of 5 nm. The first bias magnetic layer 41a includes, for example, $Fe_{50}Co_{50}$ of 2 nm. The first magnetic coupling layer 44a includes, for example, Ru of 0.9 nm. The second bias magnetic layer 41b includes, for example, $Fe_{50}Co_{50}$ of 2 nm. The bias pinning layer 42 includes, for example, IrMn of 7 nm.

Figure 4E:
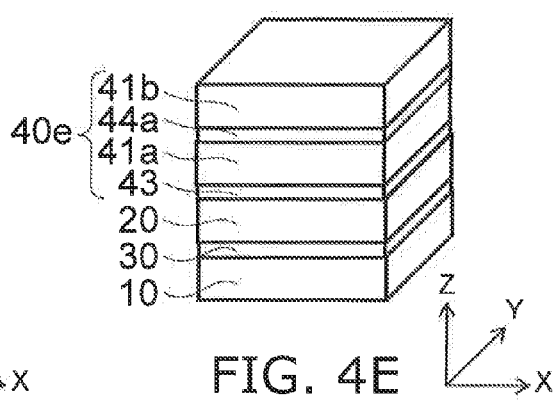
Figure 4C:
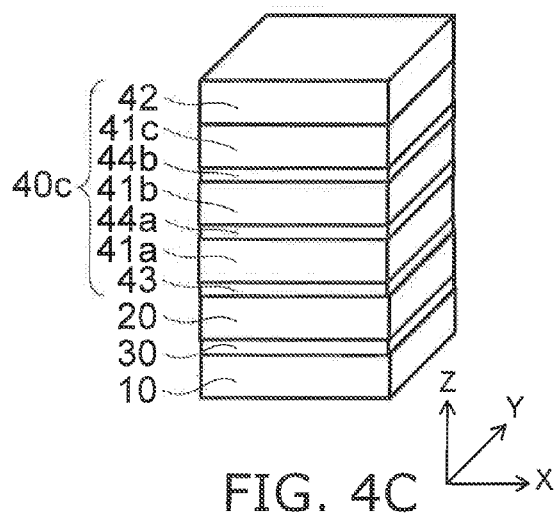

FIG. 4C is a schematic perspective view illustrating another bias layer of the first embodiment.

A bias layer 40c illustrated in FIG. 4C includes a first bias magnetic layer 41a, a second bias magnetic layer 41b, a third bias magnetic layer 41c, a bias pinning layer 42, a separating layer 43, a first magnetic coupling layer 44a, and a second magnetic coupling layer 44b. The separating layer 43 is provided between the second magnetic layer 20 and the bias pinning layer 42. The first bias magnetic layer 41a is provided between the separating layer 43 and the bias pinning layer 42. The first magnetic coupling layer 44a is provided between the first bias magnetic layer 41a and the bias pinning layer 42. The second bias magnetic layer 41b is provided between the first magnetic coupling layer 44a and the bias pinning layer 42. The second magnetic coupling layer 44b is provided between the second bias magnetic layer 41b and the bias pinning layer 42. The third magnetic layer 41c is provided between the second magnetic coupling layer 44b and the bias pinning layer 42.

In the bias layer 40a illustrated in FIG. 4A, a bias magnetic layer of a single-layer structure (the first bias magnetic layer 41a) is provided. In the bias layer 40c illustrated in FIG. 4C, bias magnetic layers of a triple-layer structure (the first bias magnetic layer 41a, the second bias magnetic layer 41b, and the third bias magnetic layer 41c) are provided through the first magnetic coupling layer 44a and the second magnetic coupling layer 44b. On this point, the bias layer 40c illustrated in FIG. 4C is different from the bias layer 40a illustrated in FIG. 4A.

The magnetization of the first bias magnetic layer 41a is set to be opposite to the magnetization of the adjacent second bias magnetic layer 41b through the first magnetic coupling layer 44a. The magnetization of the second bias magnetic layer 41b is set to be opposite to the magnetization of the adjacent third bias magnetic layer 41c through the second magnetic coupling layer 44b. By setting the magnetization directions of the plural bias magnetic layers to be anti-parallel, it is possible to suppress the stray magnetic field from the bias magnetic layers to the outside, and to suppress magnetic interference other than bias application due to exchange coupling to the second magnetic layer 20. As described later, by appropriately setting the number of the bias magnetic layers to be any one of an odd number or an even number, it is possible to appropriately select the bias directions. It may not be necessary to provide the separating layer 43.

In a case where the bias magnetic layers of the triple-layer structure are used as illustrated in FIG. 4C, the magnetization of the first bias magnetic layer 41a is the same as the magnetization of the third bias magnetic layer 41c. The magnetization direction of the second bias magnetic layer 41b is reversed with respect to the magnetization of the first bias magnetic layer 41a and the magnetization of the third bias magnetic layer 41c. In a case where an odd number of plural bias magnetic layers are used, it is favorable that the sum of magnetic film thicknesses of bias magnetic layers that are directed in the same direction be equal to the sum of magnetic film thicknesses of bias magnetic layers that are directed in the opposite direction. Accordingly, it is possible to reduce the stray magnetic field. For example, in a case where the bias magnetic layers of the triple-layer structure are used as illustrated in FIG. 4C, it is favorable that the sum of magnetic field thicknesses of the first bias magnetic layer 41a and the third bias magnetic layer 41c be equal to the magnetic film thickness of the second bias magnetic layer 41b.

The bias layer may include bias magnetic layers of four or more layers.

The materials of the respective layers included in the bias layer 40c illustrated in FIG. 4C may be the same as the materials of the respective layers included in the bias layer 40a illustrated in FIG. 4A.

The separating layer 43 includes, for example, Cu of 5 nm. The first bias magnetic layer 41a includes, for example, $Fe_{50}Co_{50}$ of 2 nm. The first magnetic coupling layer 44a includes, for example, Ru of 0.9 nm. The second bias magnetic layer 41b includes, for example, $Fe_{50}Co_{50}$ of 4 nm. The second magnetic coupling layer 44b includes, for example, Ru of 0.9 nm. The third bias magnetic layer 41c includes, for example, $Fe_{50}Co_{50}$ of 2 nm. The bias pinning layer 42 includes, for example, IrMn of 7 nm.

FIG. 4D is a schematic perspective view illustrating another bias layer of the first embodiment.

A bias layer 40d illustrated in FIG. 4D includes a first bias magnetic layer 41a and a separating layer 43. The separating layer 43 is provided between the second magnetic layer 20 and the first bias magnetic layer 41a.

In the bias layer 40a illustrated in FIG. 4A, the bias pinning layer 42 is provided in contact with the first bias magnetic layer 41a. In the bias layer 40d illustrated in FIG. 4D, the bias pinning layer 42 is not provided. On this point, the bias layer 40d illustrated in FIG. 4D is different from the bias layer 40a illustrated in FIG. 4A. It may not be necessary to provide the separating layer 43.

In a case where the bias pinning layer 42 is not provided as illustrated in FIG. 4D, the first bias magnetic layer 41a includes, for example, a hard magnetic layer. As the hard magnetic layer, for example, CoPt (the ratio of Co is 50 at. % or more and 85 at. % or less), $(Co_xPt_{100-x})_{100-y}Cr_y$ (x being 50 at. % or more and 85 at. % or less and y being 0 at. % or more and 40 at. % or less), FePt (the ratio of Pt is 40 at. % or more and 60 at. % or less), or the like may be used.

FIG. 4E is a schematic perspective view illustrating another bias layer of the first embodiment.

A bias layer 40e illustrated in FIG. 4E includes a first bias magnetic layer 41a, a second bias magnetic layer 41b, a separating layer 43, and a first magnetic coupling layer 44a. The separating layer 43 is provided between the second magnetic layer 20 and the second bias magnetic layer 41b. The first bias magnetic layer 41a is provided between the separating layer 43 and the second bias magnetic layer 41b. The first magnetic coupling layer 44a is provided between the first bias magnetic layer 41a and the second magnetic layer 41b.

As illustrated in FIG. 4E, even in a case where the bias pinning layer 42 is not provided, the plural bias magnetic layers may be provided through the magnetic coupling layer. By providing the plural bias magnetic layers through the magnetic coupling layer and by coupling the plural bias magnetic layers in the anti-parallel direction, it is possible to suppress the stray magnetic field to the outside.

Figure 5A:
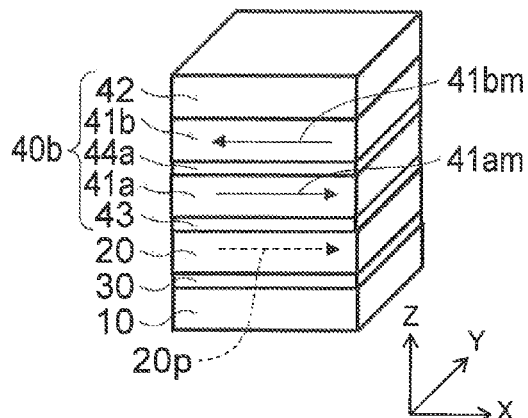
FIGS. 5A and 5B are schematic perspective views illustrating a difference of bias directions of the embodiment.
Figure 5B:
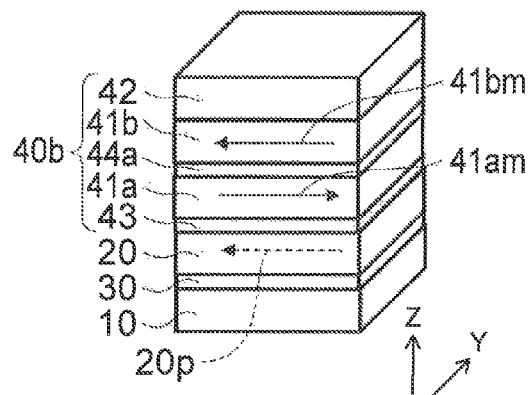

FIGS. 5A and 5B are schematic perspective views illustrating a difference of bias directions of the embodiment.

FIG. 5A represents a state where the magnetization of the first bias magnetic layer 41a is parallel (0°) to a direction of a bias applied from the first bias magnetic layer to the second magnetic layer 20. FIG. 5B illustrates a state where the magnetization of the first bias magnetic layer 41a is anti-parallel to the direction of the bias applied from the first bias magnetic layer to the second magnetic layer 20.

The strain sensing element illustrated in FIGS. 5A and 5B includes the bias layer 40b described in regard to FIG. 4B. An arrow 41am illustrated in FIGS. 5A and 5B represents the magnetization of the first bias magnetic layer 41a. An arrow 41bm illustrated in FIGS. 5A and 5B represents the magnetization of the second bias magnetic layer 41b. An arrow 20p illustrated in FIGS. 5A and 5B represents the direction of the bias applied to the second magnetic layer 20.

As illustrated in FIG. 5A, in a case where a configuration of a positive magnetic coupling is used in the separating layer 43, the bias 20p is applied to the second magnetic layer 20 in a direction parallel to the magnetization 41am of the first bias magnetic layer 41a adjacent to the second magnetic layer 20 through the separating layer 43. As illustrated in FIG. 5B, in a case where a configuration of a negative magnetic coupling is used in the separating layer 43, the bias 20p is applied to the second magnetic layer 20 in a direction anti-parallel to the magnetization 41am of the first bias magnetic layer 41a adjacent to the second magnetic layer 20 through the separating layer 43.

Whether to select the positive magnetic coupling or the negative magnetic coupling is determined according to the material included in the separating layer 43 and the thickness of the material. In the thickness of each material, in a case where Ruderman-Kittel-Kasuya-Yosida (RKKY) coupling becomes positive, the positive magnetic coupling occurs. In the thickness of each material, in a case where Ruderman-Kittel-Kasuya-Yosida (RKKY) coupling becomes negative, the negative magnetic coupling occurs.

As the material used in the separating layer 43, for example, Cu, Ru, Rh, Ir, V, Cr, Nb, Mo, Ta, W, Rr, or the like indicating the RKKY coupling is used. With respect to these elements, it is possible to divide the positive magnetic coupling and the negative magnetic coupling according to the thickness of the separating layer 43. Other than the elements, Au, Ag, Pt, Pd, Ti, Zr, Hf, or the like may be used. In a case where these elements are used as the separating layer 43, the positive magnetic coupling is mainly obtained. In a case where the negative magnetic coupling is used, Ru, Rh or Ir may be used.

If the strength of the bias 20p due to the bias layer 40b is too strong, the anisotropic magnetic field of the second magnetic layer 20 (magnetization free layer) is too high, and thus, rotation of the magnetization 20m with respect to strain becomes weak. In order to obtain an improvement effect of reversibility and to prevent the reduction of the sensitivity of the rotation of the magnetization 20m with respect to strain, it is favorable to appropriately set the strength of the bias 20p from the bias layer 40b. In order to appropriately control the strength of the bias 20p from the bias layer 40b, it is favorable to use Cu having an exchange coupling constant, which is not very high, of RKKY. In Cu, since the change of the magnetic coupling for the thickness is minute, the control becomes simple, which is favorable.

Figure 6:
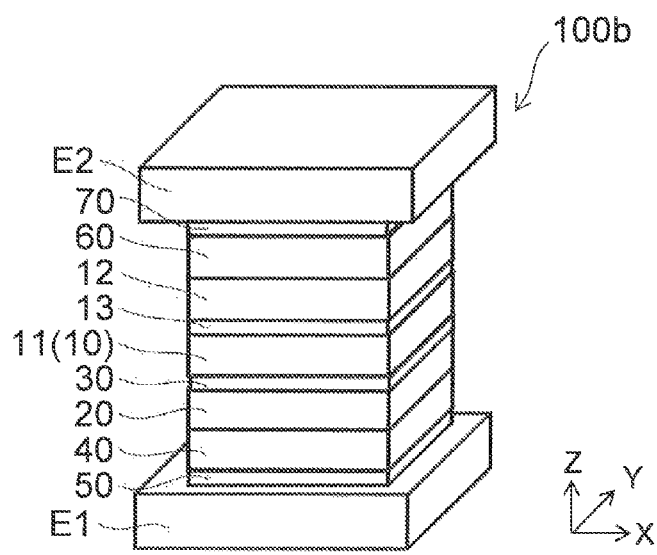
FIG. 6 is a schematic perspective view illustrating another strain sensing element according to the first embodiment.

FIG. 6 is a schematic perspective view illustrating another strain sensing element according to the first embodiment.

As illustrated in FIG. 6, a strain sensing element 100b used in the embodiment includes a first electrode E1, an underlayer 50, a bias layer 40, a second magnetic layer 20, a spacer layer 30, a first magnetization free layer 11, a magnetic coupling layer 13, a second magnetization pinned layer 12, a pinning layer 60, a capping layer 70, and a second electrode E2. The first magnetization pinned layer 11 corresponds to the first magnetic layer 10.

The underlayer 50 is provided between the first electrode E1 and the second electrode E2. The bias layer 40 is provided between the underlayer 50 and the second electrode E2. The second magnetic layer 20 is provided between the bias layer 40 and the second electrode E2. The spacer layer 30 is provided between the second magnetic layer 20 and the second electrode E2. The first magnetization pinned layer 11 is provided between the spacer layer 30 and the second electrode E2. The magnetic coupling layer 13 is provided between the first magnetization pinned layer 11 and the second electrode E2. The second magnetization pinned layer 12 is provided between the magnetic coupling layer 13 and the second electrode E2. The pinning layer 60 is provided between the second magnetization pinned layer 12 and the second electrode E2. The capping layer 70 is provided between the pinning layer 60 and the second electrode E2.

In the example, the strain sensing element 100b has a top spin valve type structure.

The underlayer 50 includes, for example, Ta/Ru. The thickness of the Ta layer is, for example, 3 nm. The thickness of the Ru layer is, for example, 2 nm.

As the bias layer 40, for example, IrMn (7 nm)/$Fe_{50}Co_{50}$ (2 nm)/Ru (0.9 nm)/$Fe_{50}Co_{50}$ (2 nm)/Cu (5 nm) is used.

The second magnetic layer 20 (magnetization free layer) includes, for example, $Co_{40}Fe_{40}B_{20}$ (4 nm).

The spacer layer 30 includes, for example, an MgO layer having a thickness of 2.0 nm.

The first magnetization pinned layer 11 includes, for example, $Co_{40}Fe_{40}B_{20}/Fe_{50}Co_{50}$. The thickness of the $Co_{40}Fe_{40}B_{20}$ layer is, for example, 2 nm. The thickness of the $Fe_{50}Co_{50}$ layer is, for example, 1 nm.

The magnetic coupling layer 13 includes, for example, an Ru layer having a thickness of 0.9 nm.

The second magnetization pinned layer 12 includes, for example, a $Co_{75}Fe_{25}$ layer having a thickness of 2.5 nm. The pinning layer 60 includes, for example, an IrMn layer having a thickness of 7 nm.

The capping layer includes, for example, Ta/Ru. The thickness of the Ta layer is, for example, 1 nm. The thickness of the Ru layer is, for example, 5 nm.

In the above-described example, the structure of the bias layer 40 has the structure of the bias layer 40b illustrated in FIG. 4B. In the top spin valve, in a case where the bias layer 40 is formed (−Z-axis direction) under the second magnetic layer 20 (magnetization free layer), it is possible to use a structure obtained by vertically inverting the structure of the bias layer 40b illustrated in FIG. 4B. Each of the layers included in the strain sensing element 100b may include the material described with reference to the strain sensing element 100a illustrated in FIG. 3.

Figure 7:
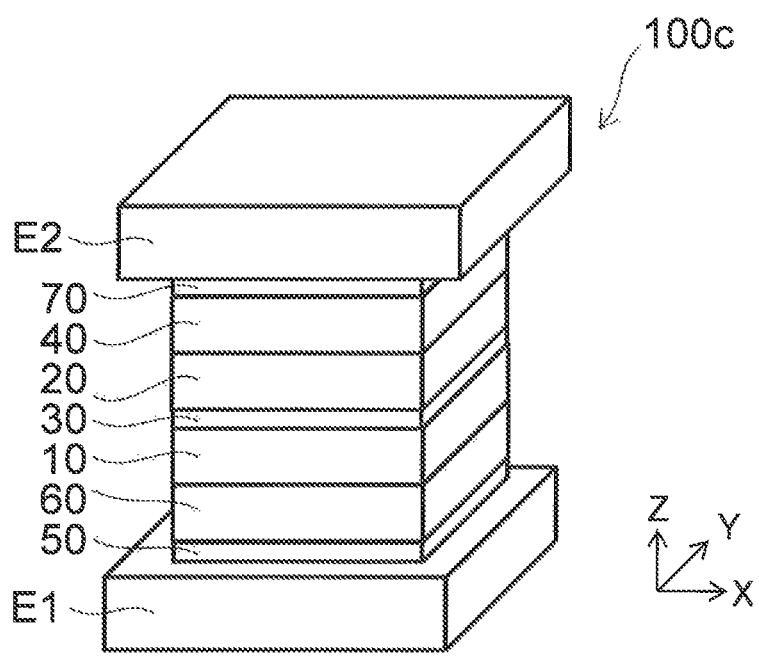
FIG. 7 is a schematic perspective view illustrating another strain sensing element according to the first embodiment.

FIG. 7 is a schematic perspective view illustrating another strain sensing element according to the first embodiment.

As illustrated in FIG. 7, a strain sensing element 100c used in the embodiment includes a first electrode E1, an underlayer 50, a pinning layer 60, a first magnetic layer 10, a spacer layer 30, a second magnetic layer 20, a bias layer 40, a capping layer 70, and a second electrode E2. The underlayer 50 is provided between the first electrode E1 and the second electrode E2. The pinning layer 60 is provided between the underlayer 50 and the second electrode E2. The first magnetic layer 10 (reference layer) is provided between the pinning layer 60 and the second electrode E2. The spacer layer 30 is provided between the first magnetic layer 10 and the second electrode E2. The second magnetic layer 20 is provided between the spacer layer 30 and the second electrode E2. The bias layer 40 is provided between the second magnetic layer 20 and the second electrode E2. The capping layer 70 is provided between the bias layer 40 and the second electrode E2.

In the above-described strain sensing elements 100a and 100b, a structure in which the first magnetization pinned layer 11, the magnetic coupling layer 13 and the second magnetization pinned layer 12 are used is applied. In the strain sensing element 100c illustrated in FIG. 7, a single pinned structure that uses a single magnetization pinned layer is applied.

The underlayer 50 includes, for example, Ta/Ru. The thickness of the Ta layer is, for example, 3 nm. The thickness of the Ru layer is, for example, 2 nm.

The pinning layer 60 includes, for example, an IrMn layer having a thickness of 7 nm.

The first magnetic layer (reference layer) includes, for example, a $Co_{40}Fe_{40}B_{20}$ layer having a thickness of 3 nm.

The spacer layer 30 includes, for example, an MgO layer having a thickness of 2.0 nm.

The second magnetic layer 20 (magnetization free layer) includes, for example, $Co_{40}Fe_{40}B_{20}$ (4 nm).

The bias layer 40 includes, for example, Cu (5 nm)/$Fe_{50}Co_{50}$ (2 nm)/Ru (0.9 nm)/$Fe_{50}Co_{50}$ (2 nm)/IrMn (7 nm).

The capping layer 70 includes Ta/Ru. The thickness of the Ta layer is, for example, 1 nm. The thickness of the Ru layer is, for example, 5 nm.

In the above-described example, the structure of the bias layer 40 has the structure of the bias layer 40b illustrated in FIG. 4B. Each of the layers included in the strain sensing element 100c may include the material described with reference to the strain sensing element 100a illustrated in FIG. 3.

FIGS. 8A to 8F are schematic cross-sectional views illustrating a magnetization pinning direction of a magnetization pinned layer, a magnetization pinning direction of a bias magnetic layer, and a direction of a bias applied to a magnetization free layer.

Figures 8A, 8B, 8C:
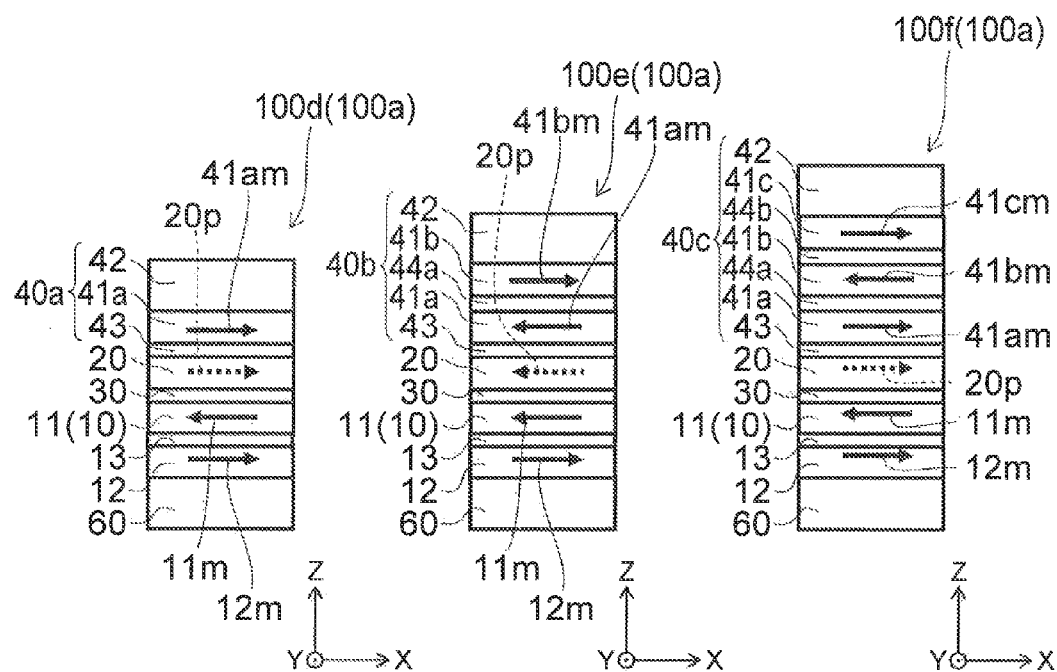
FIGS. 8A to 8F are schematic cross-sectional views illustrating a magnetization pinning direction of a magnetization pinned layer, a magnetization pinning direction of a bias magnetic layer, and a direction of a bias applied to a magnetization free layer.

FIGS. 8A to 8C illustrate the strain sensing element 100a shown in FIG. 3.

Figures 8D, 8E, 8F:
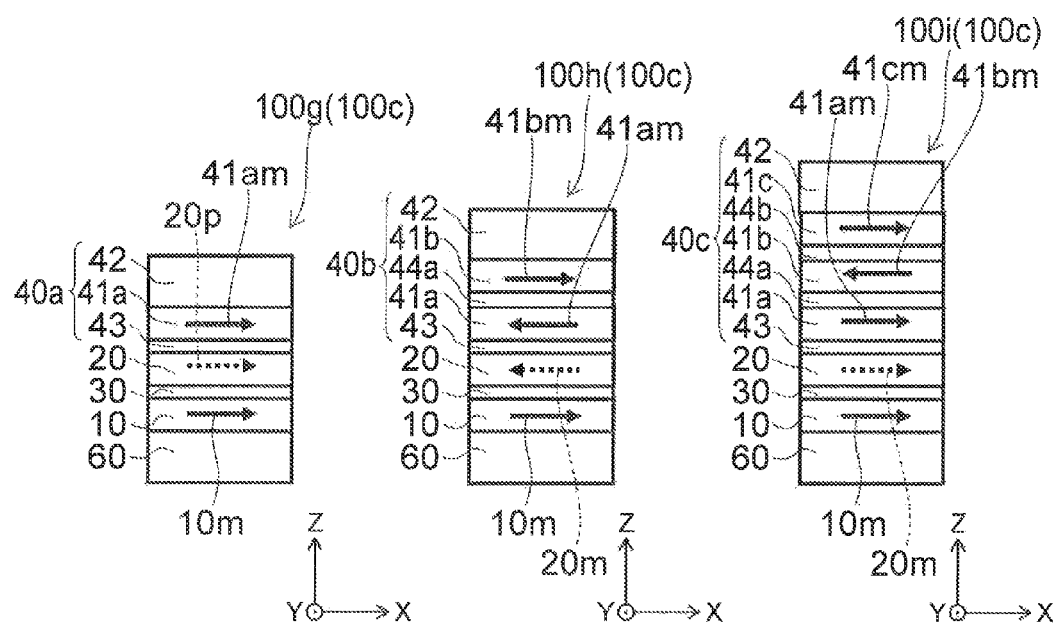

FIGS. 8D to 8E illustrate the strain sensing element 100c shown in FIG. 7.

In FIGS. 8A to 8F, a case where the magnetic coupling through the separating layer 43 is positive will be described as an example.

FIG. 8A illustrates an example in which the bias layer 40a illustrated in FIG. 4A is provided.

The bias layer 40a illustrated in FIG. 8A includes a bias magnetic layer of a single-layer structure (the first bias magnetic layer 41a). In FIG. 8A, an example is shown in which pinning of a magnetization 12m of a second magnetization pinned layer 12, a magnetization 11m of a first magnetization pinned layer 11 and a magnetization 41am of a first bias magnetic layer 41a is performed by one-time annealing in a magnetic field after a stacked body that is used as the strain sensing element 100d is formed. FIG. 8A illustrates an example in which the annealing in the magnetic field is performed as the magnetic field is applied in the right direction (X-axis direction) on the plane of the drawing.

By performing the annealing in the magnetic field in the right direction on the plane of the drawing, the magnetization 12m of the second magnetization pinned layer 12 in contact with the pinning layer 60 is fixed in the right direction (X-axis direction). At the same time, the magnetization 41am of the first bias magnetic layer 41a in contact with the bias pinning layer 42 is fixed in the right direction. The first magnetization pinned layer 11 adjacent to the second magnetization pinned layer 12 through the magnetic coupling layer 13 is magnetic-coupled in the anti-parallel direction with the second magnetization pinned layer 12 through the magnetic coupling layer 13. Thus, the magnetization 11m of the first magnetization pinned layer 11 is fixed in the left direction. As a result, in the strain sensing element 100d illustrated in FIG. 8A, the direction of a bias 20p applied from the first bias magnetic layer 41a to the second magnetic layer 20 (magnetization free layer) becomes the right direction, which is anti-parallel to the pinning direction of the magnetization 11m of the first magnetization pinned layer 11.

FIG. 8B illustrates an example in which the bias layer 40b illustrated in FIG. 4B is provided.

The bias layer 40b illustrated in FIG. 8B includes bias magnetic layers of a double-layer structure (the first bias magnetic layer 41a and the second bias magnetic layer 41b). The strain sensing element 100d illustrated in FIG. 8A includes the bias magnetic layer of the single-layer structure (the first bias magnetic layer 41a), whereas a strain sensing element 100e illustrated in FIG. 8B includes the bias magnetic layers of the double-layer structure (the first bias magnetic layer 41a and the second bias magnetic layer 41b). Thus, the magnetization 41am of the first bias magnetic layer 41a adjacent to the second magnetic layer 20 (magnetization free layer) through the separating layer 43 is fixed in the left direction (—X-axis direction). Thus, the bias 20p is applied to the second magnetic layer 20 (magnetization free layer) in the left direction. Accordingly, the direction of the bias 20p applied to the second magnetic layer 20 (magnetization free layer) becomes parallel to the pinning direction of the magnetization 11m of the first magnetization pinned layer 11.

FIG. 8C illustrates an example in which the bias layer 40c illustrated in FIG. 4C is provided.

The bias layer 40c illustrated in FIG. 8C includes bias magnetic layers of a triple-layer structure (the first bias magnetic layer 41a, the second bias magnetic layer 41b, and the third bias magnetic layer 41c). The strain sensing element 100d illustrated in FIG. 8A includes the bias magnetic layer of the single-layer structure (the first bias magnetic layer 41a), whereas a strain sensing element 100f illustrated in FIG. 8C includes the bias magnetic layers of the triple-layer structure (the first bias magnetic layer 41a, the second bias magnetic layer 41b, and the third bias magnetic layer 41c). The number of bias magnetic layers of the strain sensing element 100f illustrated in FIG. 8C is an odd number, and similarly, the number of bias magnetic layers of the strain sensing element 100d illustrated in FIG. 8A is an odd number. Thus, the magnetization 41am of the first bias magnetic layer 41a adjacent to the second magnetic layer 20 (magnetization free layer) through the separating layer 43 is fixed in the right direction. The bias 20p is applied to the second magnetic layer 20 (magnetization free layer) in the right direction. Accordingly, the direction of the bias 20p applied to the second magnetic layer 20 (magnetization free layer) becomes anti-parallel to the pinning direction of the magnetization urn of the first magnetization pinned layer 11.

In the above-described examples with reference to FIGS. 8A to 8C, the direction of the bias 20p applied to the second magnetic layer 20 (magnetization free layer) is selected as parallel or anti-parallel to the magnetization 11m of the first magnetization pinned layer 11, according to the number of the bias magnetic layers. Here, it is possible to obtain improvement of the anisotropic magnetic field of the second magnetic layer 20 (magnetization free layer) due to the bias layer 40 both in a case where the direction of the bias 20p is parallel to the magnetization 11m of the first magnetization pinned layer 11 and in a case where the direction of the bias 20p is anti-parallel to the magnetization 11m of the first magnetization pinned layer 11. Further, it is possible to improve a gauge factor.

In the case of the tunneling type strain sensing element 100 in which an insulating layer is used in the spacer layer 30, it is favorable that the direction of the bias 20p be anti-parallel to the direction of the magnetization 11m of the first magnetization pinned layer 11. The reasons will be described later. In other words, in a case where the bias layer 40 is provided in the synthetic pinned type strain sensing elements 100a and 100b including the magnetization pinned layers of the double-layer structure (the second magnetization pinned layer 12 and the first magnetization pinned layer 11), it is more favorable that the number of the bias magnetic layers included in the bias layer 40 be set to an odd number.

FIG. 8D illustrates an example in which the bias layer 40a illustrated in FIG. 4A is provided.

The bias layer 40a illustrated in FIG. 8D includes a bias magnetic layer of a single-layer structure (the first bias magnetic layer 41a), In FIG. 8D, an example is shown in which pinning of a magnetization 10m of a first magnetic layer 10 and a magnetization 41am of a first bias magnetic layer 41a is performed by one-time annealing in a magnetic field after a stacked body that is used as a strain sensing element 100g is formed. FIG. 8D illustrates an example in which the annealing in the magnetic field is performed as the magnetic field is applied in the right direction (X-axis direction) on the plane of the drawing.

By performing the annealing in the magnetic field in the right direction on the plane of the drawing, the magnetization 10m of the first magnetization pinned layer 10 in contact with the pinning layer 60 is fixed in the right direction (X-axis direction). At the same time, the magnetization 41am of the first bias magnetic layer 41a in contact with the bias pinning layer 42 is fixed in the right direction. As a result, in the strain sensing element 100g illustrated in FIG. 8D, the direction of a bias 20p applied from the first bias magnetic layer 41a to the second magnetic layer 20 (magnetization free layer) becomes the right direction, which is parallel to the pinning direction of the magnetization 10m of the first magnetic layer 10.

FIG. 8E illustrates an example in which the bias layer 40b illustrated in FIG. 4B is provided.

The bias layer 40b illustrated in FIG. 8E includes bias magnetic layers of a double-layer structure (the first bias magnetic layer 41a and the second bias magnetic layer 41b). The strain sensing element 100g illustrated in FIG. 8D includes the bias magnetic layer of the single-layer structure (the first bias magnetic layer 41a), whereas a strain sensing element 100h illustrated in FIG. 8E includes the bias magnetic layers of the double-layer structure (the first bias magnetic layer 41a and the second bias magnetic layer 41b). Thus, the magnetization 41am of the first bias magnetic layer 41a adjacent to the second magnetic layer 20 (magnetization free layer) through the separating layer 43 is fixed in the left direction (−X-axis direction). Thus, the right directional bias 20p is applied to the second magnetic layer 20 (magnetization free layer). Accordingly, the direction of the bias 20p applied to the second magnetic layer 20 (magnetization free layer) becomes anti-parallel to the pinning direction of the magnetization 10m of the first magnetic layer 10.

FIG. 8F illustrates an example in which the bias layer 40c illustrated in FIG. 4C is provided.

The bias layer 40c illustrated in FIG. 8F includes bias magnetic layers of a triple-layer structure (the first bias magnetic layer 41a, the second bias magnetic layer 41b, and the third bias magnetic layer 41c). The strain sensing element 100g illustrated in FIG. 8D includes the bias magnetic layer of the single-layer structure (the first bias magnetic layer 41a), whereas a strain sensing element 100i illustrated in FIG. 8F includes the bias magnetic layers of the triple-layer structure (the first bias magnetic layer 41a, the second bias magnetic layer 41b, and the third bias magnetic layer 41c). The number of bias magnetic layers of the strain sensing element 100i illustrated in FIG. 8F is an odd number, and similarly, the number of bias magnetic layers of the strain sensing element 100g illustrated in FIG. 8D is an odd number. Thus, the magnetization 41am of the first bias magnetic layer 41a adjacent to the second magnetic layer 20 (magnetization free layer) through the separating layer 43 is fixed in the right direction. The right directional bias 20p is applied to the second magnetic layer 20 (magnetization free layer). Accordingly, the direction of the bias 20p applied to the second magnetic layer 20 (magnetization free layer) becomes parallel to the pinning direction of the magnetization 10m of the first magnetic layer 10.

As illustrated in FIGS. 8D to 8F, in a case where the single pinned magnetization pinned layer is used, when the number of the bias magnetic layers included in the bias layer 40 is an even number, the direction of the bias 20p becomes antiparallel to the direction of the magnetization 10m of the first magnetic layer 10 in contact with the spacer layer 30.

As described above, in a case where the direction of the bias 20p applied to the second magnetic layer 20 (magnetization free layer) is anti-parallel to the magnetization pinned layer in contact with the spacer layer 30 in the first magnetic layer 10, when the number of the magnetization pinned layers of the first magnetic layer 10 is an even number, the number of the bias magnetic layers included in the bias layer 40 is set to an odd number. On the other hand, when the number of the magnetization pinned layers of the first magnetic layer 10 is an odd number, the number of the bias magnetic layers included in the bias layer 40 is set to an even number.

In a case where the direction of the bias 20p applied to the second magnetic layer 20 (magnetization free layer) is parallel to the magnetization pinned layer in contact with the spacer layer 30 in the first magnetic layer 10, when the number of the magnetization pinned layers of the first magnetic layer 10 is an even number, the number of the bias magnetic layers included in the bias layer 40 is set to an even number. On the other hand, when the number of the magnetization pinned layers of the first magnetic layer 10 is an odd number, the number of the bias magnetic layers included in the bias layer 40 is set to an odd number.

The bias layer may include bias magnetic layers of four or more-layer structure.

As a first example according to the embodiment, the strain sensing element 100 having the following structure is manufactured.

First Example

Underlayer 50: Ta (1 nm)/Ru (2 nm)
Pinning layer 60: $Ir_{22}Mn_{78}$ (7 nm)
Second magnetization pinned layer 12: $Co_{75}Fe_{25}$ (2.5 nm)
Magnetic coupling layer 13: Ru (0.9 nm)
First magnetization pinned layer 11: $Co_{40}Fe_{40}B_{20}$ (3 nm)
Spacer layer 30: MgO (2 nm)
Second magnetic layer 20 (magnetization free layer): $Co_{40}Fe_{40}B_{20}$ (4 nm)
Bias layer 40: Cu (5 nm)/$Fe_{50}Co_{50}$ (2 nm)/Ru (0.9 nm)/$Fe_{50}Co_{50}$ (2 nm)/IrMn (7 nm)
Capping layer 70: Cu (1 nm)/Ta (2 nm)/Ru (5 nm)

The structure of the strain sensing element 100 of the first example is the same as the structure of the strain sensing element 100a illustrated in FIG. 3. The structure of the bias layer 40 is the same as the structure of the bias layer 40b illustrated in FIG. 4B. In other words, the bias layer 40 of the first example has the structure of the separating layer 43/the first bias magnetic layer 41a/the first magnetic coupling layer 44a/the second bias magnetic layer 41b/the bias pinning layer 42.

As a first comparative example, a strain sensing element having the following structure is manufactured.

First Comparative Example

Underlayer 50: Ta (1 nm)/Ru (2 nm)
Pinning layer 60: $Ir_{22}Mn_{78}$ (7 nm)
Second magnetization pinned layer 12: $Co_{75}Fe_{25}$ (2.5 nm)
Magnetic coupling layer 13: Ru (0.9 nm)
First magnetization pinned layer 11: $Co_{40}Fe_{40}B_{20}$ (3 nm)
Spacer layer 30: MgO (2 nm)
Second magnetic layer 20 (magnetization free layer): $Co_{40}Fe_{40}B_{20}$ (4 nm)
Capping layer 70: Cu (10 nm)/Ta (2 nm)/Ru (5 nm)

In the first comparative example, the bias layer 40 is not provided.

With respect to a stacked body of the first example and a stacked body of the first comparative example, annealing is performed while a magnetic field of 6500 Oe (oersteds) is applied for one hour at 320° C., after molding. Thus, pinning of a magnetization 12m of the second magnetization pinned layer 11 and a magnetization 11m of a first magnetization pinned layer 11 is performed. In the first example, pinning of a magnetization 41am of the first bias magnetic layer 41a and a magnetization 41bm of the second bias magnetic layer 41b is performed.

FIGS. 9A to 9D are graphs illustrating examples of results of magnetic characteristics before the stacked bodies of the first example and the first comparative example are fabricated to element (uniform film state).

Figure 9A:
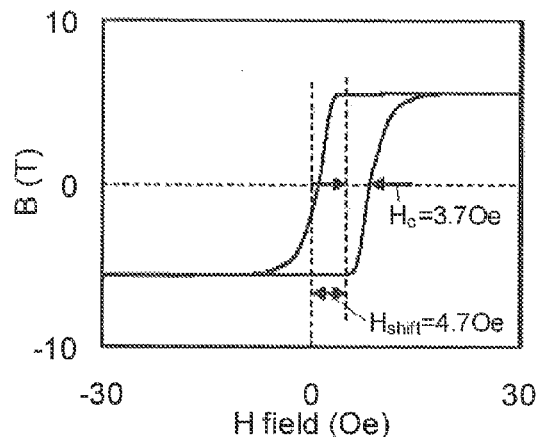
FIGS. 9A to 9D are graphs illustrating examples of results of magnetic characteristics before the stacked bodies of the first example and the first comparative example are element-processed.
Figure 9B:
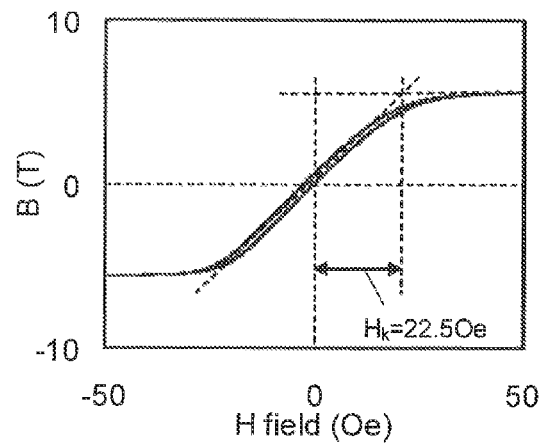
Figure 9C:
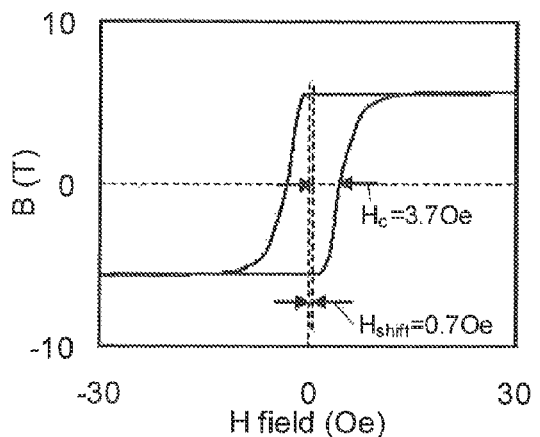
Figure 9D:
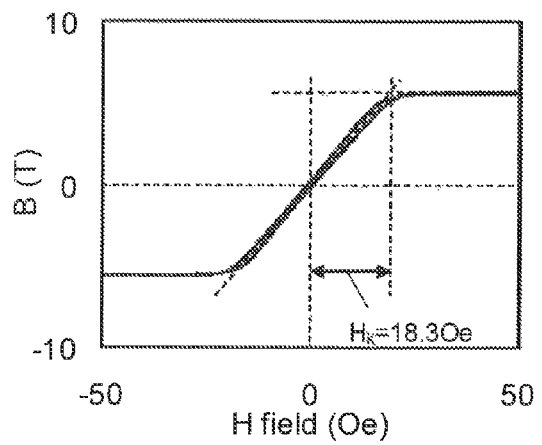

FIG. 9A illustrates an example of a B—H loop obtained by evaluating a magnetic field applied in a direction where the annealing in the magnetic field is performed as a positive magnetic field, in the first example. FIG. 9B illustrates an example of a B—H loop obtained by evaluation of a magnetic field applied in a direction, in the plane, perpendicular to the direction where the annealing in the magnetic field is performed, in the first example. FIG. 9C illustrates an example of a B—H loop obtained by evaluating a magnetic field applied in a direction where the annealing in the magnetic field is performed as a positive magnetic field, in the first comparative example. FIG. 9D illustrates an example of a B—H loop obtained by evaluation of a magnetic field applied in a direction, in the plane, perpendicular to the direction where annealing in magnetic field is performed, in the first comparative example.

In the B—H loop illustrated in FIG. 9A, a loop shape of a magnetization easy axis with a satisfactory squareness is obtained. In the B—H loop illustrated in FIG. 9B, a loop shape of a typical magnetization hard axis is obtained. As a result, it can be understood that in-plane induced magnetic anisotropy in which the direction of the annealing in the magnetic field is used as the magnetization easy axis is obtained in the second magnetic layer 20 (magnetization free layer). From the BH loop illustrated in FIG. 9A, it is confirmed that a hysteresis loop of the second magnetic layer 20 (magnetization free layer) has $H_{shift}$ of 4.7 Oe in the positive magnetic field direction. This means that since the bias 20p is applied to a minus magnetic field side by the bias layer 40, a magnetic field of 4.7 Oe on a plus side is necessary in order to reverse the second magnetic field 20 (magnetization free layer). An anisotropic magnetic field $H_k$ calculated from the BH loop illustrated in FIG. 9B relating to the strength of the induced magnetic anisotropy is estimated as 22.5 Oe. Thus, it is confirmed that the anisotropic magnetic field is improved by providing the bias layer 40, compared with the first comparative example. A coercivity $H_c$ estimated from the BH loop illustrated in FIG. 9A is 3.7 Oe. A magnetostriction constant is 20 ppm. The same value as that of the first comparative example is estimated as the magnetostriction constant.

In the B—H loop illustrated in FIG. 9C, a loop shape of a magnetization easy axis with a satisfactory squareness is obtained. In the B—H loop illustrated in FIG. 9D, a loop shape of a typical magnetization hard axis is obtained. As a result, it can be understood that in-plane induced magnetic anisotropy in which the direction of the annealing in the magnetic field is used as the magnetization easy axis is obtained in the second magnetic layer 20 (magnetization free layer). An anisotropic magnetic field $H_k$ calculated from the BH loop illustrated in FIG. 9D relating to the strength of the induced magnetic anisotropy is estimated as 18.3 Oe. A coercivity $H_e$ of the second magnetic layer 20 (magnetization free layer) of the first comparative example, estimated from the BH loop illustrated in FIG. 9C is 3.7 Oe. The coercivity $H_e$ is a characteristic index indicating the easiness of magnetization rotation. The coercivity H, of 3.7 Oe may be a value in which the magnetization rotation due to the inverse-magnetostriction effect sufficiently and easily occurs. As a result of the evaluation of the magnetostriction constant of the first comparative example, the magnetostriction constant is 20 ppm. This value may be a sufficiently high value for occurrence of the magnetization rotation due to strain.

From the results of FIGS. 9A to 9D, the configuration of the second magnetic layer 20 (magnetization free layer) of the first example is the same as the configuration of the second magnetic layer 20 (magnetization free layer) of the first comparative example. The coercivity $H_c$ of the first example is substantially the same as the coercivity $H_c$ of the first comparative example. The magnetostriction constant of the first example is substantially the same as the magnetostriction constant of the first comparative example. On the other hand, in the first embodiment, it can be understood that the anisotropic magnetic field $H_k$ is improved by providing the bias layer 40, compared with the first comparative example.

The stacked body of the first example and the first comparative example is processed as a Current-perpendicular-to-the-plane (CPP) element by photography or milling. The element size of the Current-perpendicular-to-the-plane (CPP) element is set to 20 µm×20 µm.

FIGS. 10A to 10E are graphs illustrating examples of results of strain sensor characteristics of the strain sensing element 100 of the first example.

Evaluation of the strain sensor characteristics illustrated in FIGS. 10A to 10E is performed by substrate bending method. Strain application is performed for a wafer (stripe-shaped wafer) obtained by cutting a wafer of the strain sensing element 100 in a stripe shape by a four-point bending method using a knife edge. A road cell is added to the knife edge that bends the stripe-shaped wafer, and strain applied to the strain sensing element 100 on a front surface of the wafer is calculated by the weight measured by the load cell. In the calculation of strain, a general theoritical expression of two-side support beams represented as the following expression is used.

[Expression 1]

$$\varepsilon = -\frac{3(L_1 - L_2)G}{2\,Wt^2 e_s} \qquad \text{Expression 1}$$

In expression 1, $e_s$ represents the Young's modulus of the wafer. $L_1$ represents the length between edges of an outer knife edge. $L_2$ represents the length between edges of an inner knife edge. W represents the width of the stripe-shaped wafer. t represents the thickness of the stripe-shaped wafer. G represents the weight applied to the knife edge. The weight applied to the knife edge may be continuously changed by motor control.

The direction of the strain application is a direction perpendicular to the direction of the magnetization 11m of the first magnetization pinned layer 11 in the same plane. In the specification of the present application, a positive value strain corresponds to a tensile strain, and a negative value strain corresponds to a compressive strain.

Figure 10A:
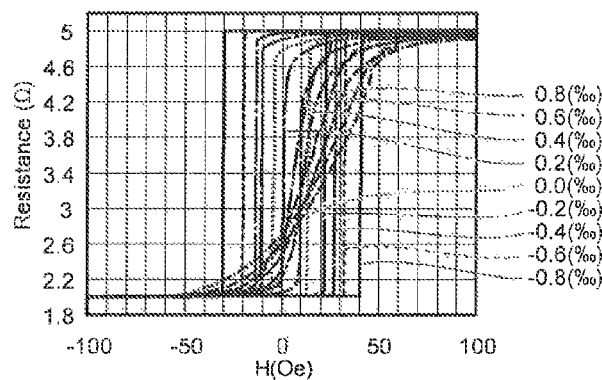
FIGS. 10A to 10E are graphs illustrating examples of results of strain sensor characteristics of the strain sensing element 100 of the first example.

In the example illustrated in FIG. 10A, with respect to the strain sensing element 100 of the first example having an element size of 20 µm×20 µm, the strain applied to the strain sensing element 100 is set as a fixed value with an interval of 0.2 (‰) between −0.8 (‰) and 0.8 (‰). FIG. 10A illustrates respective examples of results obtained by measuring magnetic field dependency of electrical resistance in respective strains. An external magnetic field direction at the time of measurement is applied in a direction parallel to the second magnetization pinned layer 12 within the plane. A positive external magnetic field represents a case where a magnetic field is applied in a direction opposite to the magnetization 12m of the second magnetization pinned layer 12. From FIG. 10A, it can be understood that the shape of the R—H loop is changed by the value of the applied strain. This means that the in-plane magnetic anisotropy of the second magnetic layer 20 (magnetization free layer) is changed by the inverse-magnetostriction effect.

Figure 10B:
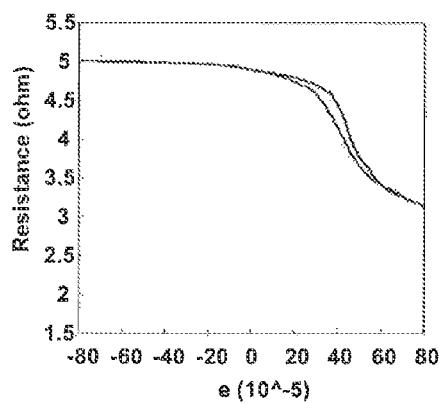
Figure 10C:
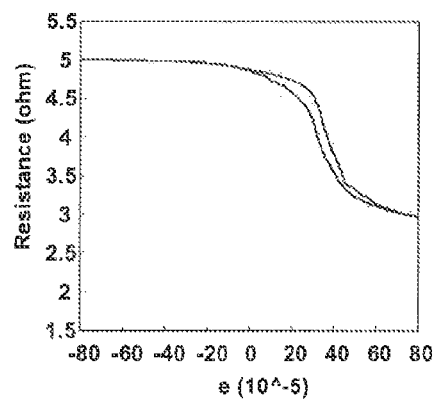
Figure 10D:
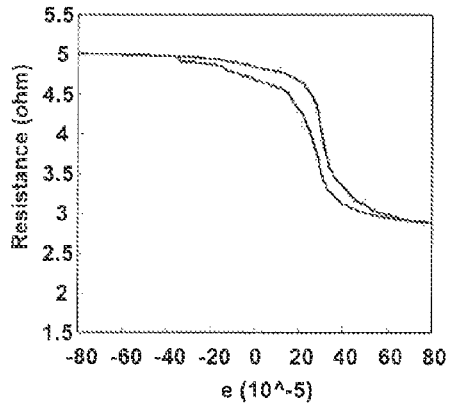
Figure 10E:
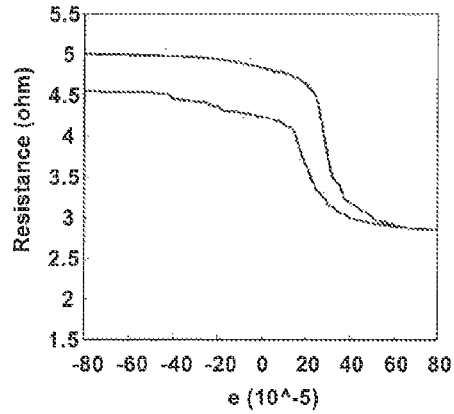

FIGS. 10B to 10E represent changes of electrical resistances in the strain sensing element 100 of the first example when an external magnetic field is fixed and strain is continuously swept between −0.8 (‰) and 0.8 (‰). The strain is swept from −0.8 (‰) to 0.8 (‰), and then, is swept from 0.8 (‰) to −0.8 (‰). These results represent the strain sensor characteristics. In FIG. 10B, the evaluation is performed by applying an external magnetic field of 15 Oe. In FIG. 10C, an external magnetic field of 10 Oe is applied to perform the evaluation. In FIG. 10D, the evaluation is performed at an external magnetic field of 7.5 Oe. In FIG. 10E, the evaluation is performed at an external magnetic field of 5 Oe.

In the strain sensing element 100 of the embodiment, it is possible to obtain a high gauge factor by applying an appropriate bias magnetic field. The external magnetic field may also be applied by providing a hard bias (to be described later) to a side wall of the strain sensing element 100. In the strain sensing element 100 of the first example, the evaluation is performed by simply applying the external magnetic field using a coil. The gauge factor in each bias magnetic field of the first example is estimated from the change of the electrical resistance with respect to the strain, from FIGS. 10B to 10E.

The gauge factor is represented by the following expression.

$$GF=(dR/R)/d\epsilon \quad \text{Expression (2)}$$

From FIG. 10B, in the first example, the gauge factor obtained when the external magnetic field is 15 Oe is 1642. From FIG. 10C, in the first example, the gauge factor obtained when the external magnetic field is 10 Oe is 2147. From FIG. 10D, in the first example, the gauge factor obtained when the external magnetic field is 7.5 Oe is 3063.

On the other hand, as illustrated in FIG. 10E, when the external magnetic field is 5 Oe, the change of the electrical resistance when the strain is swept from −0.8 (‰) to 0.8 (‰) and is then swept from 0.8 (‰) to −0.8 (‰) is irreversible. From these results, in the first example, the maximum gauge factor (3063) is obtained when the bias magnetic field is 7.5 Oe.

FIGS. 11A to 11E are graphs illustrating examples of strain sensor evaluation results of the strain sensing element of the first comparative example.

Figure 11A:
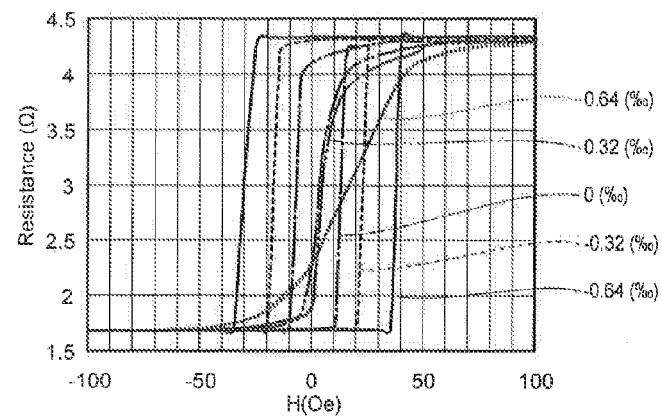
FIGS. 11A to 11E are graphs illustrating examples of strain sensor evaluation results of the strain sensing element of the first comparative example.

In the example illustrated in FIG. 11A, with respect to the strain sensing element of the first comparative example having an element size of 20 μm×20 μm, the strain applied to the strain sensing element is set as a fixed value at an interval of 0.2 (‰) between −0.8 (‰) to 0.8 (‰). FIG. 11A illustrates respective examples of results obtained by measuring magnetic field dependency of electrical resistance in respective strains. From FIG. 11A, similar to FIG. 10A, it can be understood that the shape of the R—H loop is changed by the value of the applied strain. This represents that in-plane magnetic anisotropy of the second magnetic layer 20 (magnetization free layer) is changed by the inverse-magnetostriction effect.

Figure 11B:
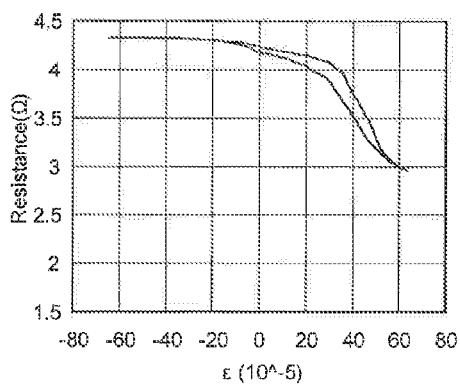
Figure 11C:
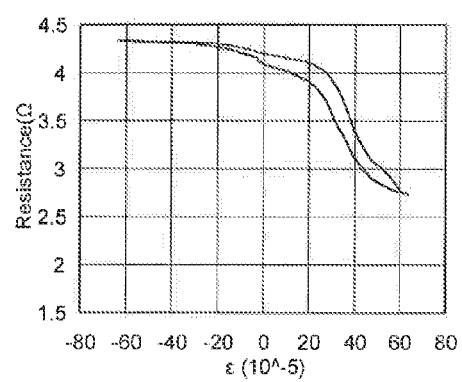
Figure 11D:
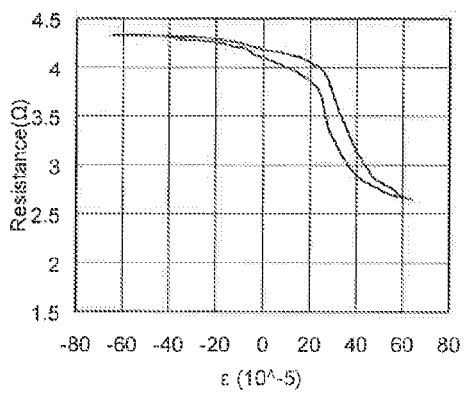
Figure 11E:
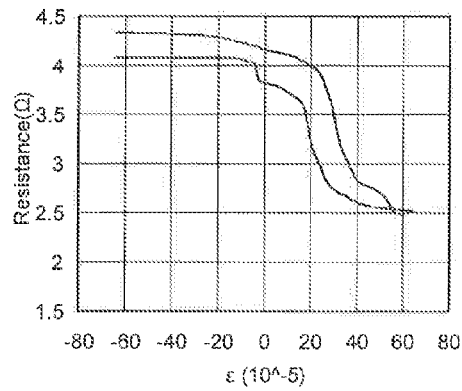

FIGS. 11B to 11E represent changes of electrical resistances in the sensing element of the first comparative example when an external magnetic field is fixed and strain is continuously swept between −0.8 (‰) and 0.8 (‰). In FIG. 11B, the evaluation is performed by applying an external magnetic field of 15 Oe. In FIG. 11C, an external magnetic field of 10 Oe is applied to perform the evaluation. In FIG. 11D, the evaluation is performed by applying an external magnetic field of 7.5 Oe. In FIG. 11E, the evaluation is performed by applying an external magnetic field of 5 Oe.

From FIG. 11B, in the first comparative example, the gauge factor obtained when the external magnetic field is 15 Oe is 1357. From FIG. 11C, in the first comparative example, the gauge factor obtained when the external magnetic field is 10 Oe is 1580. From FIG. 11D, the gauge factor obtained when the external magnetic field is 7.5 Oe is 2087.

On the other hand, as illustrated in FIG. 11E, when the external magnetic field is 5 Oe, the change of the electrical resistance when the strain is swept from −0.8 (‰) to 0.8 (‰) and is then swept from 0.8 (‰) to −0.8 (‰) is irreversible. From these results, in the first comparative example, the maximum gauge factor (2087) is obtained when the bias magnetic field is 7.5 Oe.

From the results of FIGS. 10A to 10E and FIGS. 11A to 11E, in the first example in which the bias layer 40 is provided, it is confirmed that the gauge factor is high, compared with the first comparative example.

Figure 12:
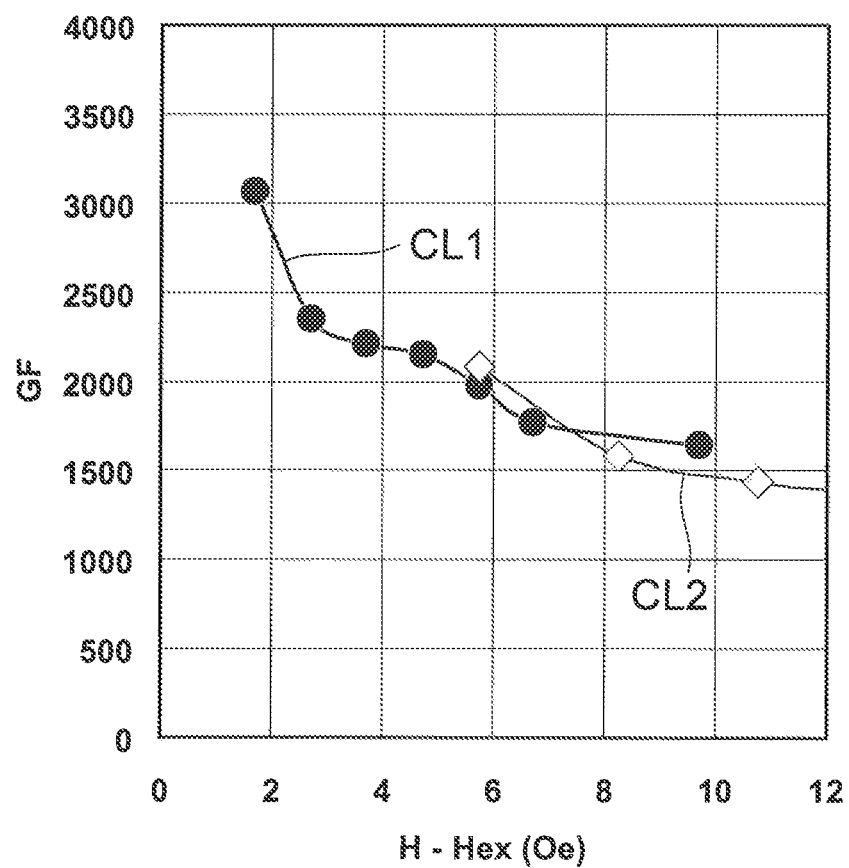
FIG. 12 is a graph illustrating an example of evaluation results of gauge factors in various bias electric fields.

FIG. 12 is a graph illustrating an example of evaluation results of gauge factors in various bias electric fields.

In order to review the results described with reference to FIGS. 10A to 10E and FIGS. 11A to 11E, the gauge factors are evaluated by various bias magnetic fields, with respect to the first example and the first comparative example. The horizontal axis in the graph of FIG. 12 represents a difference between a bias magnetic field used for evaluation and $H_{shift}$ of the RH loop in zero strain of FIG. 10A and FIG. 11A.

In the strain sensing element 100 according to the embodiment, in a magnetic field that is relatively close to a central position (position of $H_{shift}$) of the hysteresis loop of the RH loop in the zero strain, a relatively high gauge factor is obtained. This can be understood from the shape of the RH loop evaluated by applying different strains, as illustrated in FIG. 10A and FIG. 11A. In other words, if a bias magnetic field in which H−$H_{shift}$ is small is applied, a higher gauge factor is obtained.

As understood from a curve CL2 illustrated in FIG. 12, in the first comparative example, the maximum value (2087) of the gauge factor is obtained around 5.5 Oe of H—$H_{shift}$. In the bias magnetic field of 5.5 Oe or less, the movement of the magnetization of the second magnetic layer with respect to the strain is irreversible. On the other hand, as understood from a curve CL1 illustrated in FIG. 12, in the first example, a reversible strain sensor characteristic is obtained around 1.5 Oe of H−$H_{shift}$. As a result, the maximum value (3063) of the gauge factor is obtained around 1.5 Oe of H−$H_{shift}$. The maximum value (3063) of the gauge factor of the first example is larger than the maximum value (2087) of the gauge factor of the first comparative example. By providing the bias layer 40 as described above, it is possible to reduce the bias magnetic field in which the reversible strain sensor characteristic is obtained, and to confirm that the gauge factor is improved.

The principle capable of improving reversibility of the strain sensor characteristic by providing the bias layer 40 will be described with reference to the accompanying drawings.

FIGS. 13A to 13F are schematic diagrams illustrating in-plane angle dependency of free energy of a magnetization free layer of an embodiment.

FIGS. 14A to 14F are schematic diagrams illustrating in-plane angle dependency of free energy of a magnetization free layer of a comparative example.

FIGS. 13A, 13C, 13E, 14A, 14C and 14E are graphs illustrating the in-plane angle dependency of the free energy of the magnetization free layer. FIGS. 13B, 13D, 13F, 14B, 14D and 14F illustrate magnetization of the magnetization free layer and strain occurring in the magnetization free layer.

Figure 13A:
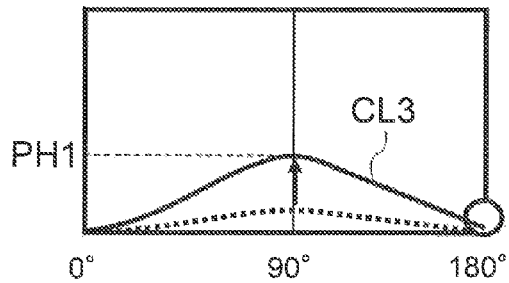
FIGS. 13A to 13F are schematic diagrams illustrating in-plane angle dependency of free energy of a magnetization free layer of an embodiment.

In the examples illustrated in FIGS. 13A to 13F and FIGS. 14A to 14F, a direction parallel to the magnetization 10m of the first magnetic layer 10 (magnetization pinned layer) is defined as 0°, and a direction anti-parallel thereto is defined as 180°. As described with reference to FIGS. 9A to 9D, the second magnetic layer 20 (magnetization free layer) has in-plane magnetic anisotropy in which the direction of 0° and 180° corresponds to a magnetization easy axis MA1 and the direction of 90° and 270° corresponds to a magnetization hard axis MA2 by the induced magnetic anisotropy due to the annealing in the magnetic field. This represents that in a case where a relative angle between the magnetization 10m of the first magnetic layer 10 and the magnetization 20m of the second magnetic layer 20 is 90° (or 270°), a distribution in which the free energy of the second magnetic layer 20 (magnetization free layer) becomes the maximum is obtained, as illustrated in FIG. 13A.

Figure 13B:
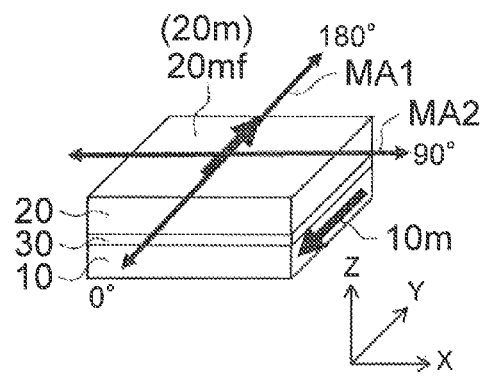
Figure 13C:
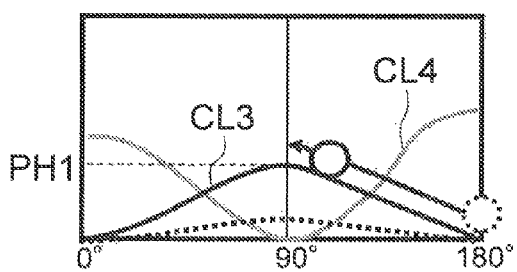
Figure 13D:
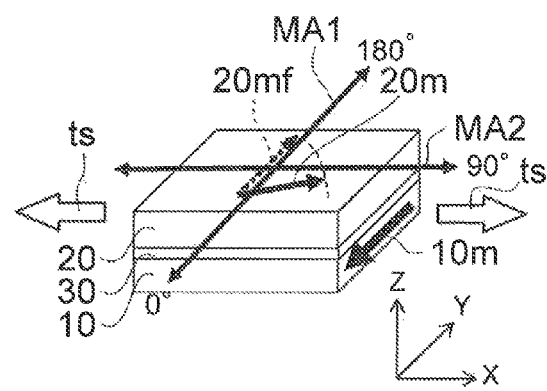

As illustrated in FIGS. 13A and 13B, an initial magnetization 20mf of the second magnetic layer 20 (magnetization free layer) is set to 180°. The state of rotation of the magnetization 20m due to the change of free energy in a case where stress is applied to the second magnetic layer 20 will be described with reference to FIGS. 13C to 13F. If the tensile stress ts is applied in the direction of 90° (or 270°) so that a curve CL3 illustrated in FIG. 13C is changed to a curve CL4, free energy due to magnetic strain energy in the direction of 0° and 180° increases. Then, the magnetization 20m of the second magnetic layer 20 is changed from the direction of 180° to the direction of 90° (or 270°).

Figure 13E:
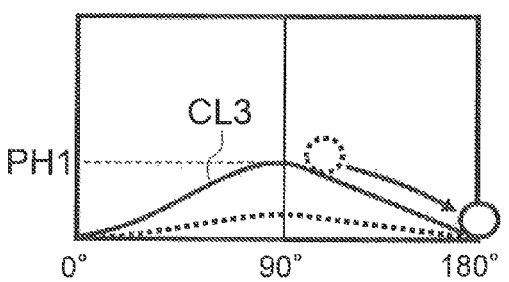
Figure 13F:
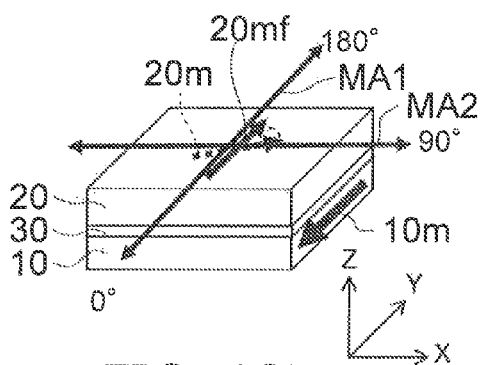

A height PH1 of a peak of energy distribution of the induced magnetic anisotropy represented as the curve CL3 in FIGS. 13A and 13B is proportional to the above-mentioned anisotropic magnetic field $H_k$. As illustrated in FIGS. 13A, 13C and 13E, in a case where the anisotropic magnetic field $H_k$ is large to a certain extent, the height PH1 of the peak of the energy distribution of the induced magnetic anisotropy around 90° is sufficiently large. Thus, the magnetization 20m of the second magnetic layer 20 that is changed from 180° to around 90° due to the tensile stress ts is easily returned to 180° when the tensile stress ts is removed. In other words, the reversibility of the electrical resistance change for the strain is improved.

On the other hand, as illustrated in FIG. 14C, in a case where the anisotropic magnetic field $H_k$ is low, the magnetization 20m of the second magnetic layer 20 has a component that passes a height PH2 of a peak of energy distribution of the induced magnetic anisotropy around 90° and goes to 0° without returning to 180° after the tensile stress ts is removed. This corresponds to a situation where the electrical resistance change for the strain is irreversible, and is described with reference to FIGS. 10E, 11E and 12.

In comparison of the first example and the first comparative example, even though the magnetostriction constant, the coercivity $H_c$ and the MR ratio of the first example in which the anisotropic magnetic field $H_k$ is improved by providing the bias layer 40 are respectively the same as the magnetostriction constant, the coercivity $H_c$ and the MR ratio of the first comparative example, the gauge factor of the first example shows a high value. It is considered that this phenomenon is based on the principle described in FIGS. 13A to 14F. In other words, the reason why the gauge factor of the first example shows the high value is because a reversible strain sensor characteristic is obtained without an extra bias magnetic field due to the improvement of the anisotropic magnetic field $H_k$.

As second to fourth examples according to the embodiment, the strain sensing element 100 having the following structure is manufactured.

Second Example

Underlayer 50: Ta (1 nm)/Ru (2 nm)
Pinning layer 60: $Ir_{22}Mn_{78}$ (7 nm)
Second magnetization pinned layer 12: $Co_{75}Fe_{25}$ (2.5 nm)
Magnetic coupling layer 13: Ru (0.9 nm)
First magnetization pinned layer 11: $Co_{40}Fe_{40}B_{20}$ (3 nm)
Spacer layer 30: MgO (2 nm)
Second magnetic layer 20 (magnetization free layer): $Co_{40}Fe_{40}B_{20}$ (4 nm)
Bias layer 40: Cu (2.4 nm to 5 nm)/$Fe_{50}Co_{50}$ (3 nm)/IrMn (7 nm)
Capping layer 70: Cu (1 nm)/Ta (2 nm)/Ru (5 nm)

Third Example

Underlayer 50: Ta (1 nm)/Ru (2 nm)
Pinning layer 60: $Ir_{22}Mn_{78}$ (7 nm)
Second magnetization pinned layer 12: $Co_{75}Fe_{25}$ (2.5 nm)
Magnetic coupling layer 13: Ru (0.9 nm)
First magnetization pinned layer 11: $Co_{40}Fe_{40}B_{20}$ (3 nm)
Spacer layer 30: MgO (2 nm)
Second magnetic layer 20 (magnetization free layer): $CO_{40}Fe_{40}B_{20}$ (4 nm)
Bias layer 40: Cu (2.4 nm to 5 nm)/$Fe_{50}Co_{50}$ (2 nm)/Ru (0.9 nm)/$Fe_{50}Co_{50}$ (2 nm)/IrMn (7 nm)
Capping layer 70: Cu (1 nm)/Ta (2 nm)/Ru (5 nm)

Fourth Embodiment

Underlayer 50: Ta (1 nm)/Ru (2 nm)
Pinning layer 60: $Ir_{22}Mn_{78}$ (7 nm)
Second magnetization pinned layer 12: $Co_{75}Fe_{25}$ (2.5 nm)
Magnetic coupling layer 13: Ru (0.9 nm)
First magnetization pinned layer 11: $Co_{40}Fe_{40}B_{20}$ (3 nm)
Spacer layer 30: MgO (2 nm)
Second magnetic layer 20 (magnetization free layer): $Co_{40}Fe_{40}B_{20}$ (4 nm)
Bias layer 40: Cu (2.4 nm to 5 nm)/$Fe_{50}Co_{50}$ (2 nm)/Ru (0.9 nm)/$Fe_{50}Co_{50}$ (4 nm)/Ru (0.9 nm)/$Fe_{50}Co_{50}$ (2 nm)/IrMn (7 nm)
Capping layer 70: Cu (1 nm)/Ta (2 nm)/Ru (5 nm)

The structure of the strain sensing element 100 of the third example is the same as the structure of the strain sensing element 100a illustrated in FIG. 3, similar to the first example. The structure of the bias layer 40 is the same as the structure of the bias layer 40b illustrated in FIG. 4B. In other words, the bias layer 40 of the third example has the structure of the separating layer 43/the first bias magnetic layer 41a/the first magnetic coupling layer 44a/the second bias magnetic layer 41b/the bias pinning layer 42.

The structure of the strain sensing element 100 of the second example is the same as the structure of the strain sensing element 100a illustrated in FIG. 3. The structure of the bias layer 40 is the same as the structure of the bias layer 40a illustrated in FIG. 4A. In other words, the bias layer 40 of the second embodiment has the structure of the separating layer 43/the first bias magnetic layer 41a/the bias pinning layer 42.

The structure of the strain sensing element 100 of the fourth example is the same as the structure of the strain sensing element 100a illustrated in FIG. 3. The structure of the bias layer 40 is the same as the structure of the bias layer 40c illustrated in FIG. 4C. In other words, the bias layer 40 of the fourth example has the structure of the separating layer 43/the first bias magnetic layer 41a/the first magnetic coupling layer 44a/the second bias magnetic layer 41b/a second magnetic coupling layer 44b/the third bias magnetic layer 41c/the bias pinning layer 42.

With respect to stacked bodies of the strain sensing elements 100 of the second to fourth examples, plural stacked bodies are created in each of the second to fourth examples by changing the thickness of Cu of the separating layer 43. Then, similar to the results illustrated in FIGS. 9A to 9D, evaluation of the magnetic characteristics is performed before element-processing.

FIGS. 15A to 15D are graphs illustrating examples of results of magnetic characteristics before the stacked bodies of the second to fourth examples are element-processed.

Figure 15A:
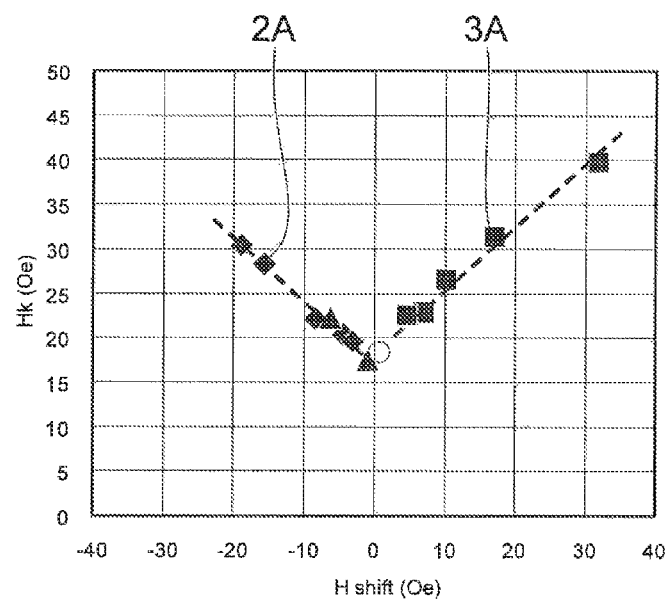
FIGS. 15A to 15D are graphs illustrating examples of results of magnetic characteristics before the stacked bodies of the second to fourth examples are element-processed.

FIG. 15A illustrates an example of a plotted result in which analysis is performed by the method illustrated in FIGS. 9A to 9D to estimate $H_{shift}$ and $H_k$, and in which the horizontal axis represents $H_{shift}$ and the vertical axis represents $H_k$.

FIG. 15A illustrates the plotted result of the first comparative example in which the bias layer 40 is not provided. In FIG. 15A, the result of the third example is represented as "black squares". In FIG. 15A, the result of the second example is represented as "black rhombuses". In FIG. 15A, the result of the fourth example is represented as "black triangles". In FIG. 15A, the result of the first comparative example is represented as "white round".

As understood from FIG. 15A, it can be understood that $H_{shift}$ has a negative value in the second example and the fourth example having odd-numbered bias magnetic layers. In the third example having even-numbered bias magnetic layers, it can be understood that $H_{shift}$ has a positive value. In the second to fourth examples, as the thickness of Cu of the separating layer 43 is changed, a stacked body having $H_{shift}$ of a different absolute value is realized. In each of the second to fourth examples, it is confirmed that as the thickness of Cu of the separating layer 43 is thin, $H_{shift}$ has a large absolute value.

From FIG. 15A, it can be understood that as the absolute value of $H_{shift}$ is large, the anisotropic magnetic field is improved. From this result, it can be understood that it is possible to control the amount of improvement of the anisotropic magnetic field $H_k$ by adjusting the thickness of Cu of the separating layer 43. Here, if the anisotropic magnetic field $H_k$ is improved, the reversibility of the magnetization 20m of the second magnetic layer 20 for the strain is improved, but if a higher than necessary the anisotropic magnetic field $H_k$ is given, it is difficult to cause the change of the magnetization 20m of the second magnetic layer 20 for the strain. Thus, it is favorable to set the amount of improvement of the anisotropic magnetic field $H_k$ to an appropriate amount. It is favorable to set the anisotropic magnetic field $H_k$ to about 20 Oe or more to about 30 Oe or less, for example.

Figure 15B:
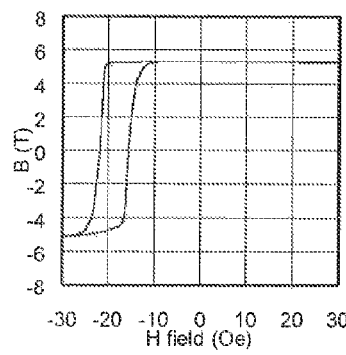

FIG. 15B illustrates an example of a BH loop obtained by evaluating a magnetic field applied in a direction where annealing in a magnetic field is performed as a positive magnetic field, with respect to an example 2A in which $H_{shift}$ in the second example is about −19 Oe.

Figure 15C:
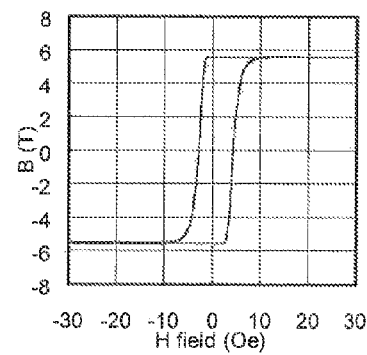

FIG. 15C illustrates an example of a BH loop obtained by evaluating a magnetic field applied in a direction where annealing in a magnetic field is performed as a positive magnetic field, with respect to the first comparative example.

Figure 15D:
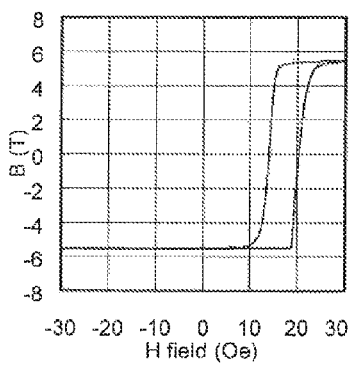

FIG. 15D illustrates an example of a BH loop obtained by evaluating a magnetic field applied in a direction where annealing in a magnetic field is performed as a positive magnetic field, with respect to an example 3A in which $H_{shift}$ in the third example is about 18 Oe.

First, with reference to FIG. 15C in the first comparative example, it can be understood that a hysteresis loop of the second magnetic layer 20 (magnetization free layer) is vertically symmetrical and has a satisfactory squareness. On the other hand, in the example 2A illustrated in FIG. 15B, it can be understood that the squareness is satisfactory on an upper side of a hysteresis loop of the second magnetic layer 20 (magnetization free layer) but the squareness is slightly weakened on a lower side. This means that the stability of magnetization on a side anti-parallel to the direction of the bias applied to the second magnetic layer 20 (magnetization free layer) from the bias layer 40 is slightly degraded. The weakening of the squareness in the example 2A represents that the stability of the magnetization is slightly degraded in a case where the second magnetic layer 20 (magnetization free layer) is parallel to the first magnetization pinned layer 11, as understood from FIG. 8A.

On the other hand, in the example 3A illustrated in FIG. 15C, it can be understood that the squareness is satisfactory on the lower side of the hysteresis loop of the second magnetic layer 20 (magnetization free layer), but the squareness is slightly weakened on the upper side. This means that the stability of magnetization on a side anti-parallel to the direction of the bias applied to the second magnetic layer 20 (magnetization free layer) from the bias layer 40 is slightly degraded. The weakening of the squareness in the example 3A represents that the stability of the magnetization is slightly degraded in a case where the second magnetic layer 20 (magnetization free layer) is anti-parallel to the first magnetization pinned layer 11, as understood from FIG. 8B.

Here, in the case of the tunneling type strain sensing element in which an insulating layer is used in the spacer layer 30, it is more favorable that the direction of the bias 20p be anti-parallel to the direction of the magnetization 11m of the first magnetization pinned layer 11. This is because it is easy to obtain a high gauge factor in a case where the strain sensing element is driven as a strain sensor between 90° and 180° since the change of electrical resistance is drastic in a case where a relative angle between a pinning layer and a free layer is changed between 90° and 180°, compared with a case where the relative angle therebetween is changed between 0° and 90°, in the tunneling type strain sensing element.

Accordingly, as in the second to fourth examples, in a case where the bias layer 40 is provided in a synthetic pinned type strain sensing element including a magnetization pinned layer of two-layer structure, it is more favorable to set the number of bias magnetic layers included in the bias layer 40 to an odd number. As described in FIGS. 15A to 15D, this is because the stability of magnetization is excellent in the direction anti-parallel to the first magnetization pinned layer 11 in a case where the odd-numbered bias magnetic layer is set.

However, even in a case where the even-numbered bias magnetic layer is used, by setting the thickness of Cu of the separating layer 43 to an appropriate value and preventing the excessive increase in the absolute value of $H_{shift}$, it is possible to maintain the stability of magnetization in the anti-parallel direction without weakening the stability.

It is favorable to set the direction of the bias applied to the second magnetic layer (magnetization free layer) from the bias layer 40 to 180° with respect to the pinning direction of the magnetization 11m of the first magnetization pinned layer 11.

FIGS. 16A to 16D are schematic diagrams illustrating another strain sensing element according to the embodiment.

In the above-described embodiment, a case where the direction of the bias applied to the second magnetic layer 20 (magnetization free layer) from the bias layer 40c is parallel or anti-parallel to the first magnetization pinned layer 11 is described. Here, the bias direction is not limited to the direction parallel and anti-parallel to the first magnetization pinned layer 11. The bias may be applied in an arbitrary direction.

Figure 16A:
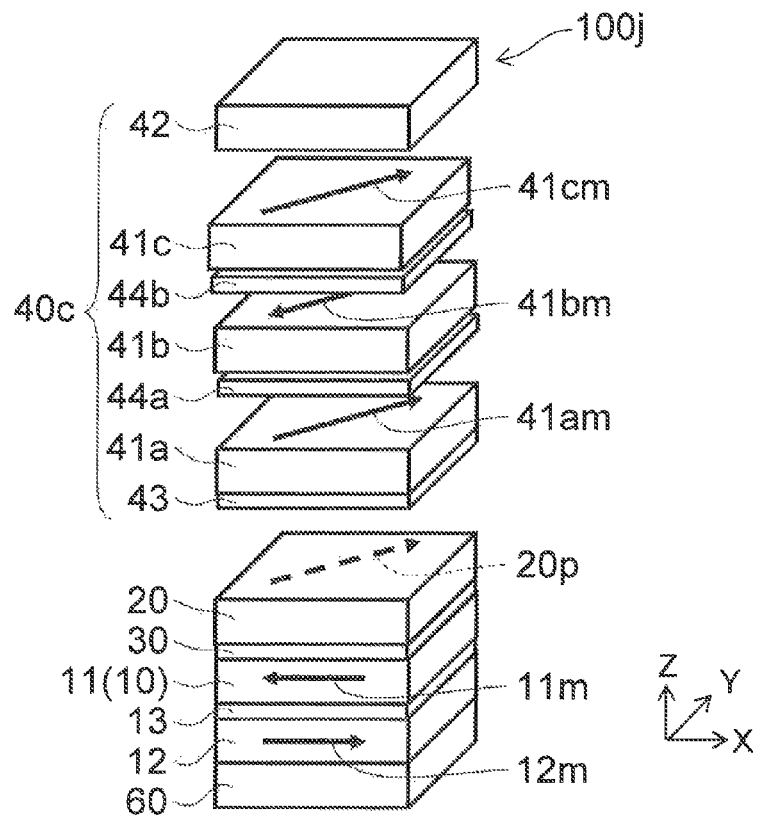
FIGS. 16A to 16D are schematic diagrams illustrating another strain sensing element according to the embodiment.
Figure 16B:
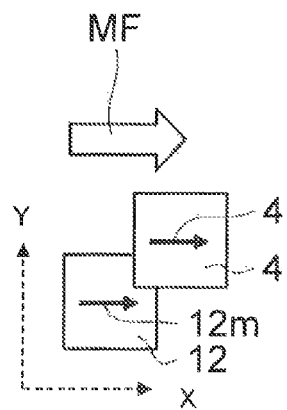

For example, as illustrated in FIG. 16A, the direction of the bias 20p may be set to 135° (or 225°) with respect to the direction of the magnetization 11m of the first magnetization pinned layer 11. Such a setting of the direction of the bias 20p may be performed according to two-stage annealing in a magnetic field as illustrated in FIGS. 16B and 16C, selection of the material used in the pinning layer 60 and selection of the material used in the bias pinning layer 42.

An anti-ferromagnetic material used in the pinning layer 60 or the bias pinning layer 42 has a different temperature at which the magnetization pinning occurs, according to its composition. For example, an ordered alloy based material such as PtMn has a high temperature at which the magnetization pinning occurs, compared with a material such as IrMn in which the magnetization pinning irregularly occurs. For example, the annealing in the magnetic field of two stages as illustrated in FIGS. 16B and 16C is performed using PtMn in the pinning layer 60 of a strain sensing element 100j illustrated in FIG. 16A and using IrMn in the bias pinning layer 42. Then, during annealing at 320° for ten hours, illustrated in FIG. 16B, the second magnetization pinned layer 12 in contact with the pinning layer 60 is fixed to the right direction. The third bias magnetic layer 41c in contact with the bias pinning layer 42 is fixed once in the right direction.

Figure 16C:
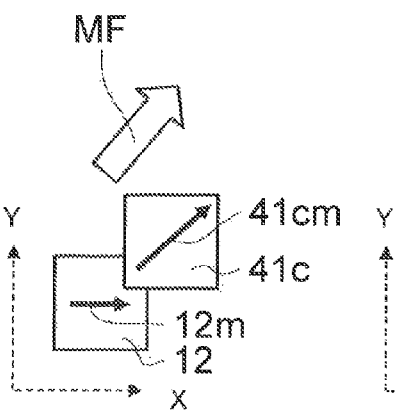
Figure 16D:
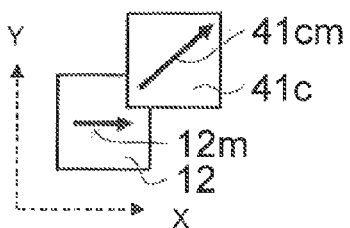

Then, for example, if the direction of a magnetic field MF is changed during annealing at 250° for one hour as illustrated in FIG. 16C, it is possible to perform setting such that a magnetization 41cm of the third bias magnetic layer 41c in contact with the bias pinning layer 42 is directed in an upper right direction while the magnetization 12m of the second magnetization pinned layer 12 in contact with the pinning layer 60 is maintained in the right direction. The direction of the magnetization is maintained after returning to a room temperature, as illustrated in FIG. 16D.

In this manner, it is possible to arbitrarily set the direction of the bias 20p to the first magnetization pinned layer 11 and the second magnetic layer 20 (magnetization free layer) according to the annealing method in the magnetic field, the material selection of the pinning layer 60 and the material selection of the bias pinning layer 42. Here, as described above, in the case of the tunneling type strain sensing element in which the insulating layer is used in the spacer layer 30, it is more favorable that the direction of the bias 20p be anti-parallel to the direction of the magnetization urn of the first magnetization pinned layer 11. Specifically, it is favorable to set the relative angle between the direction of the magnetization 11m of the first magnetization pinned layer 11 and the direction of the bias 20p to 90° or more and 270° or less, and it is more favorable to set the relative angle to 135° or more and 225° or less.

FIGS. 17A to 17D are schematic diagrams illustrating another strain sensing element according to the embodiment.

Figure 17A:
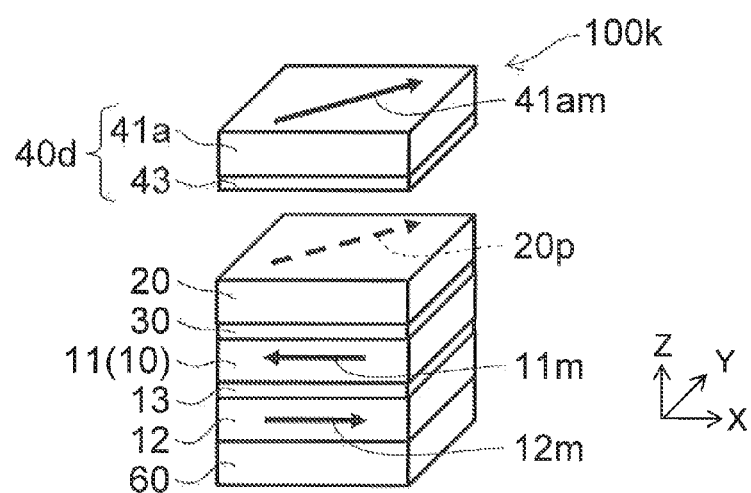
FIGS. 17A to 17D are schematic diagrams illustrating another strain sensing element according to the embodiment.
Figures 17B, 17C, 17D:
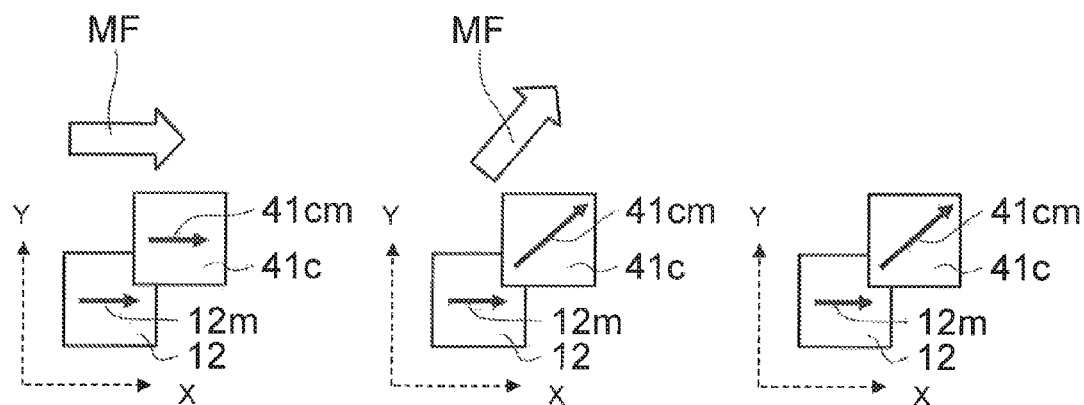

As illustrated in FIGS. 4D and 4E, even in the strain sensing element including the bias layers 40d and 4Oe that do not use the pinning layer 60, it is possible to arbitrarily set the directions of the first magnetization pinned layer 11 and the bias 20p. For example, as illustrated in FIG. 17A, it is possible to set the direction of the bias 20p to 135° (or 225°) with respect to the direction of the magnetization 11m of the first magnetization pinned layer 11. Such a setting of the direction of the bias 20p may be performed by magnetization in different directions at a low temperature around the room temperature after annealing in a magnetic field as illustrated in FIGS. 17B and 17C.

In the configuration illustrated in FIGS. 17A to 17D, the pinning of the first magnetization pinned layer 11 is performed by the pinning layer 60. On the other hand, since the first bias magnetic layer 41a is not provided with the bias pinning layer, a material such as a permanent magnet having a hard magnetic characteristic is used. In the case of such a strain sensing element 100k, it is not necessary to perform the annealing in the setting of the magnetization 41am of the first bias magnetic layer 41a. Thus, the pinning of the magnetization 11m of the first magnetization pinned layer 11 may be performed by the annealing in the magnetic field, and then, the first bias magnetic layer 41a of the hard magnetic material may be magnetized by applying a magnetic field after the annealing. Here, in a case where the tunneling type strain sensing element in which an insulating layer is used in the spacer layer 30 is used, for example, it is more favorable to set the direction of the bias 20p in a direction anti-parallel to the magnetization 11m of the first magnetization pinned layer 11. Specifically, it is favorable to set the relative angle between the direction of the first magnetization pinned layer 11 and the direction of the bias layer 20p to 90° or more and 270° or less, and it is more favorable to set the relative angle to 135° or more and 225° or less.

On the other hand, in order to broaden a dynamic range of the resistance changing strain, it is favorable to set the relative angle between the direction of the first magnetization pinned layer 11 and the direction of the bias 20p to 30° or more and 60° or less, or 120° or more and 150° or less.

Figure 18:
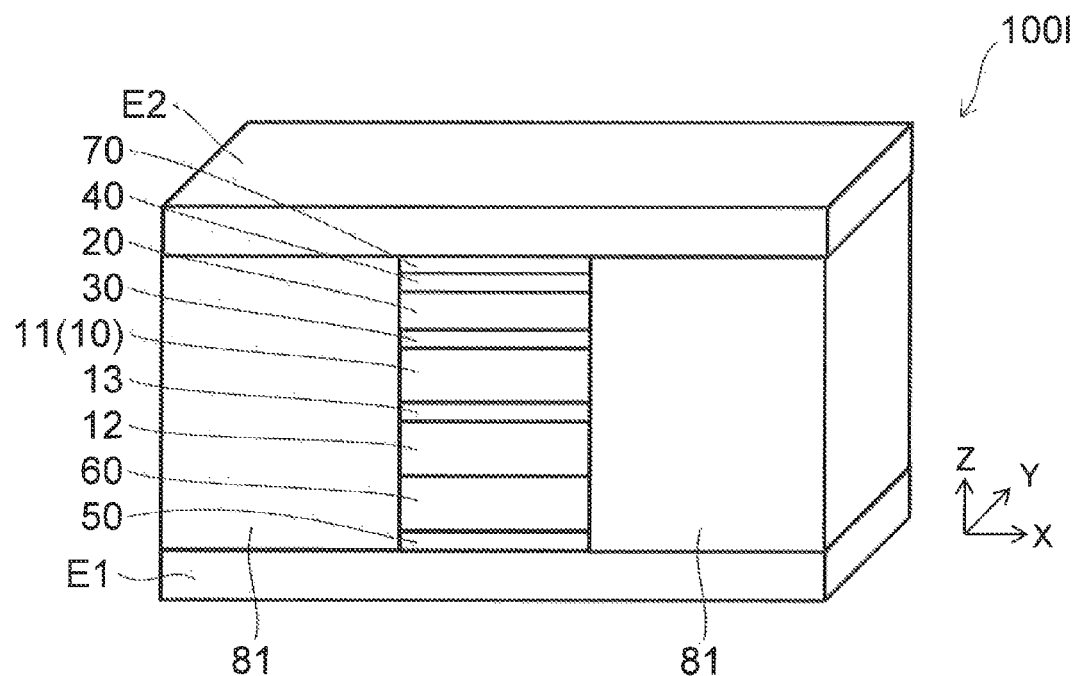
FIG. 18 is a schematic perspective view illustrating another strain sensing element used in the embodiment.

FIG. 18 is a schematic perspective view illustrating another strain sensing element used in the embodiment.

As illustrated in FIG. 18, in a strain sensing element 100l, an insulating layer is provided. In other words, two insulating layers 81 (insulating portions) that are separated from each other are provided between a first electrode E1 and a second electrode E2. The stacked body of an underlayer 50/a pinning layer 60/a second magnetization pinned layer 12/a magnetic coupling layer 13/a first magnetization pinned layer 11 (a first magnetic layer 10)/a spacer layer 30/a second magnetic layer 20/a bias layer 40/a capping layer 70 is disposed between the first electrode E1 and the second electrode E2. The stacked body is disposed between the first electrode E1 and the second electrode E2.

The stacked body includes the underlayer 50, the first magnetic layer 10 (the first magnetization free layer), the spacer layer 30, the second magnetic layer 20 (the second magnetization free layer), and the capping layer 70, in the case of the strain sensing element 100l. In other words, the insulating layers 81 are provided to face side walls of the stacked body.

Each insulating layer 81 may include, for example, aluminum oxide (for example, $Al_2O_3$), silicon oxide (for example, $SiO_2$), or the like. A leak current around the stacked body can be suppressed by the insulating layers 81.

Figure 19:
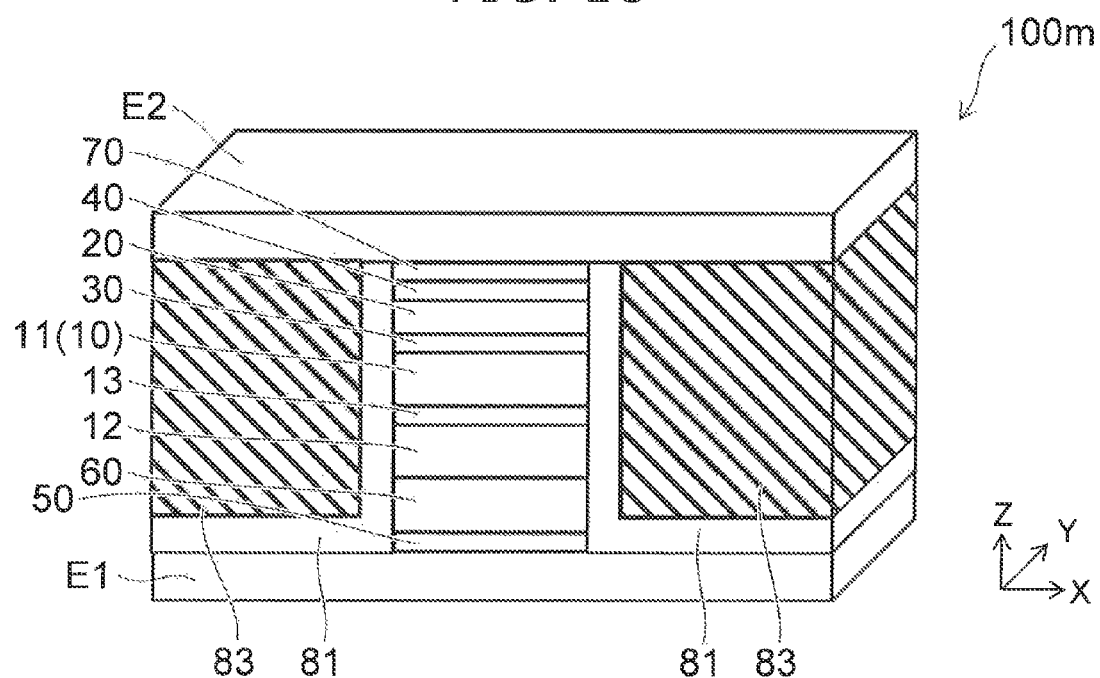
FIG. 19 is a schematic perspective view illustrating another strain sensing element used in the embodiment.

FIG. 19 is a schematic perspective view illustrating another strain sensing element used in the embodiment.

As illustrated in FIG. 19, a hard bias layer 83 is further provided in a strain sensing element 100m. In other words, two hard bias layers 83 (hard bias portions) that are separated from each other are provided between the first electrode E1 and the second electrode E2, and a stacked body of an underlayer 50/a pinning layer 60/a second magnetization pinned layer 12/a magnetic coupling layer 13/a first magnetization pinned layer 11 (a first magnetic layer 10)/a spacer layer 30/a second magnetic layer 20/a bias layer 40/a capping layer 70 is disposed between the first electrode E1 and the second electrode E2. Insulating layers 81 are disposed between the hard bias layers 83 and the stacked body. In the example, the insulating layers 81 extend between the hard bias layers 83 and the first electrode E1.

By the magnetization of the hard bias layers 83, at least one selected from the magnetization 10m of the first magnetic layer 10 and the magnetization 20m of the second magnetic layer 20 is set in a desired direction. By the hard bias layers 83, at least one selected from the magnetization 10m of the first magnetic layer 10 and the magnetization 20m of the second magnetic layer 20 can be set in the desired direction in a state where a force is not applied to the substrate.

The hard bias layer 83 includes, for example, a hard ferromagnetic material having relatively high magnetic anisotropy such as CoPt, CoCrPt or FePt. The hard bias layer 83 may include a structure in which a layer of a soft magnetic material such as FeCo or Fe and an antiferromagnetic layer are stacked. In such a case, the magnetization is directed along a predetermined direction due to exchange coupling. The thickness of the hard bias layer 83 (for example, the length along the direction from the first electrode E1 toward the second electrode E2) is, for example, 5 nm or more and 50 nm or less.

The hard bias layers 83 and the insulating layers 81 described above may be also applied to any one of the strain sensing elements to be described later.

Figure 20:
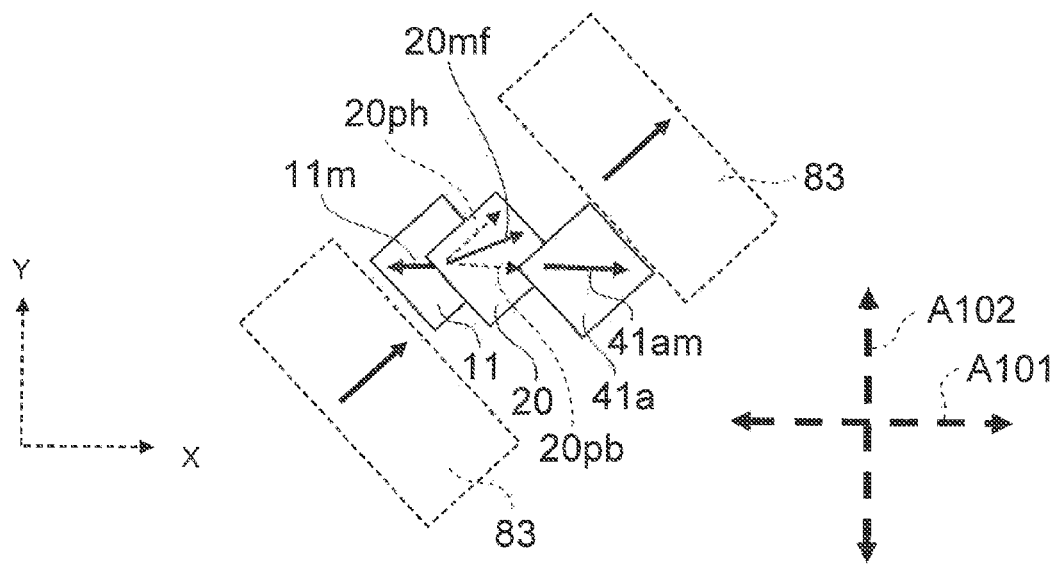
FIG. 20 is a schematic plan view illustrating an example of a bias direction of a bias layer and a bias direction of a hard bias.

FIG. 20 is a schematic plan view illustrating an example of a bias direction of a bias layer and a bias direction of a hard bias.

In the example in FIG. 20, a direction of a bias 20pb of the first bias magnetic layer 41a is set to be anti-parallel to the first magnetization pinned layer 11. The direction of a magnetic field bias 20ph of the hard bias layer 83 with respect to the first magnetization pinned layer 11 is set to 135° (or 225°).

The initial magnetization 20mf (the direction of the bias 20p) of the second magnetic layer 20 (magnetization free layer) is set to be between 135° and 180° (or between 180° and 225°) obtained from interference between the bias 20pb from the first bias magnetic layer 41a and the magnetic field bias 20ph from the hard bias layer 83. In a case where the hard bias layer 83 is provided in the strain sensing element of the embodiment including the bias layer 40 as described above, it is favorable that the initial magnetization 20mf (direction of the bias 20p) of the second magnetic layer 20 (magnetization free layer) be 90° or more and 270° or less with respect to the first magnetization pinned layer 11, and it is more favorable that the initial magnetization 20mf be 135° or more and 225° or less. Here, as indicated by arrow A101 and arrow A102 illustrated in FIG. 20, in a case where the direction of strain applied to the strain sensing element of the embodiment is parallel to or perpendicular to the direction of the magnetization 11m of the first magnetization pinned layer 11, it is possible to obtain an electrical resistance change that is monotonically increased or monotonically decreased in the range of 90° that is the dynamic magnetization range where the second magnetic layer 20 (magnetization free layer) is rotated due to the strain. Thus, this configuration is favorable.

Second Embodiment

Figure 21A:
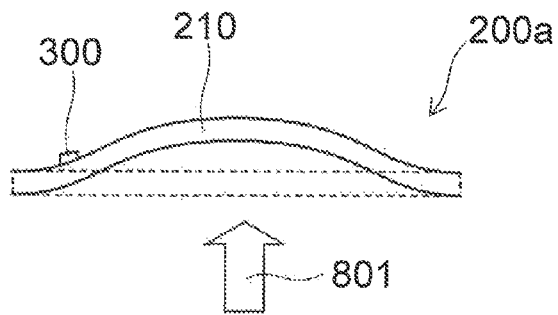
FIGS. 21A and 21B are schematic diagrams illustrating a strain sensing element according to a second embodiment.
Figure 21B:
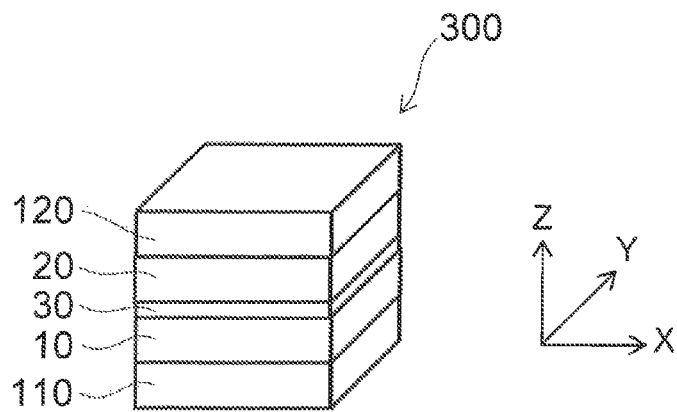

FIGS. 21A and 21B are schematic diagrams illustrating a strain sensing element according to a second embodiment.

FIG. 21A is a schematic cross-sectional view illustrating a pressure sensor in which the strain sensing element is used.

FIG. 21B is a schematic perspective view of the strain sensing element.

As illustrated in FIG. 21A, a strain sensing element 300 is used in a strain sensing element 200a. The pressure sensor 200a includes a substrate 210 and the strain sensing element 300. The substrate 210 has a flexible region. The strain sensing element 300 is provided on a part of the substrate 210. The strain sensing element 200a is the same as the pressure sensor 200 described above with reference to FIG. 1A.

As illustrated in FIG. 21B, the strain sensing element 300 according to the embodiment includes a lower bias layer 110, a lower magnetic layer 10, a spacer layer 30, an upper magnetic layer 20, and an upper bias layer 120.

The upper bias layer 120 is provided separately from the lower bias layer 110 in the stacking direction. The lower magnetic layer 10 is provided between the lower bias layer 110 and the upper bias layer 120. The spacer layer 30 is provided between the lower magnetic layer 10 and the upper bias layer 120. The upper magnetic layer 20 is provided between the spacer layer 30 and the upper bias layer 120.

The lower magnetic layer 10 serves as a first magnetization free layer where magnetization is changed according to bending of the substrate 210, for example. The upper magnetic layer 20 serves as a second magnetization free layer where magnetization is changed according to bending of the substrate 210, for example. As described later, when the substrate 210 is bent as a force is applied to the substrate 210, it is possible to cause a change in a relative angle of the magnetization of the lower magnetic layer 10 (the first magnetization free layer) and the magnetization of the upper magnetic layer 20 (the second magnetization free layer).

Next, an operation of the strain sensing element 300 will be described.

Figures 22A, 22B, 22C:
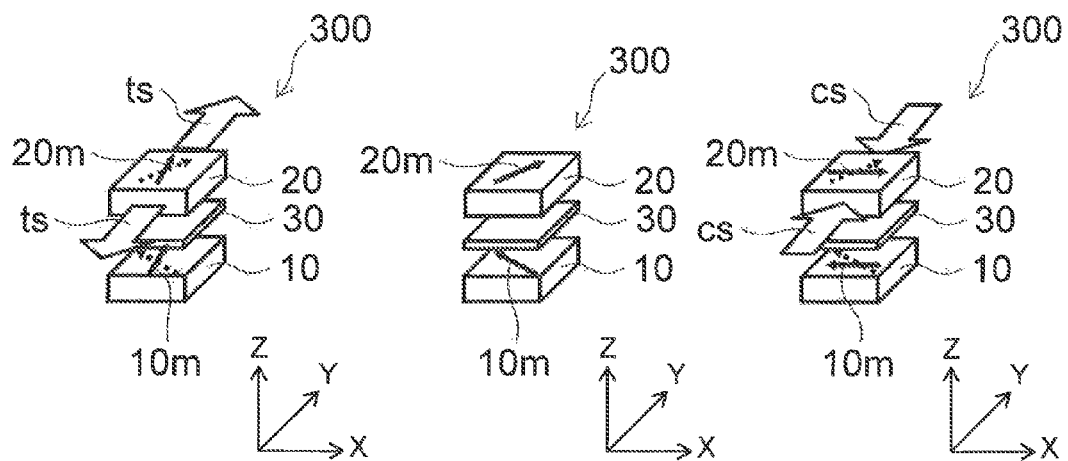
FIGS. 22A to 22C are schematic diagrams illustrating the operation of the strain sensing element according to the second embodiment.

FIGS. 22A to 22C are schematic diagrams illustrating the operation of the strain sensing element according to the second embodiment.

In FIGS. 22A to 22C, a case where the first magnetization free layer is used as the lower magnetic layer 10 and the second magnetization free layer is used as the upper magnetic layer 20 will be described as an example. In FIGS. 22A to 22C, for ease of understanding, the lower magnetic layer 10 (the first magnetization free layer), the spacer layer 30 and the upper magnetic layer 20 (the second magnetization free layer) among the respective layers of the strain sensing element 300 are shown.

The operation of the strain sensing element 300 functioning as a strain sensor is based on an application of an "inverse-magnetostriction effect" and a "magnetoresistance effect".

The "inverse-magnetostriction effect" is obtained in a ferromagnetic layer used in the magnetization free layer. The "magnetoresistance effect" occurs in a stacked film of the first magnetization free layer, the spacer layer, and the second magnetization free layer.

The "inverse-magnetostriction effect" is as illustrated above with reference to FIGS. 2A to 2C. In other words, due to the strain, the magnetization direction of the first magnetization free layer and the magnetization direction of the second magnetization free layer are changed, and the relative angle of the magnetization direction of the first magnetization free layer and the magnetization direction of the second magnetization free layer are changed. In other words, the MR effect occurs due to the inverse-magnetostriction effect.

In a case where the ferromagnetic material used in the first magnetization free layer and the second magnetization free layer has a positive magnetostriction constant, the magnetization direction changes so that the angle between the magnetization direction and a tensile strain direction becomes small and the angle between the magnetization direction and a compressive strain direction becomes large. In a case where the ferromagnetic material used in the first magnetization free layer and the second magnetization free layer have a negative magnetostriction constant, the magnetization direction changes so that the angle between the magnetization direction and the tensile strain direction becomes large and the angle between the magnetization direction and the compressive strain direction becomes small.

In a case where a combination of the materials of the stacked film of the first magnetization free layer, the spacer layer and the second magnetization free layer has a positive magnetoresistance effect, the electric resistance decreases when the relative angle between the first magnetization free layer and the second magnetization free layer is small. Further, in a case where the combination of the materials of the stacked film of the first magnetization free layer, the spacer layer and the second magnetization free layer has a negative magnetoresistance effect, the electric resistance increases when the relative angle between the first magnetization free layer and the second magnetization free layer is small.

Hereinafter, a case where each ferromagnetic material used in the first magnetization free layer and the second magnetization free layer has a positive magnetostriction constant and the stacked film of the first magnetization free layer, the spacer layer and the second magnetization free layer has the positive magnetoresistance effect will be described with respect to an example of the change of the magnetization.

As illustrated in FIG. 22B, the relative angle between the lower magnetic layer 10 (the first magnetization free layer) and the upper magnetic layer 20 (the second magnetization free layer) included in the magnetization free layer in an initial state where strain does not occur may be arbitrarily set by the bias direction from the lower bias layer 110 and the upper bias layer 120, or the bias magnetic field from the hard bias.

In the examples illustrated in FIGS. 22A to 22C, a state is shown where the direction of the bias applied to the lower magnetic layer 10 (the first magnetization free layer) from the lower bias layer 110 is set to be anti-parallel to the direction of the bias applied to the upper magnetic layer 20 (the second magnetization free layer) from the upper bias layer 120, and where the relative angle between the lower magnetic layer 10 (the first magnetization free layer) in the initial state and the upper magnetic layer 20 (the second magnetization free layer) in the initial state becomes greater than 0° and less than 180° by applying the hard bias in the bias direction from the lower bias layer 110 and the upper bias layer 120 and in the vertical direction in the plane. Details of the setting method of the initial magnetization direction will be described later.

In FIG. 22A, in a case where a tensile strain occurs based on the tensile stress ts in the arrow direction, the magnetization 10*m* of the lower magnetic layer 10 (the first magnetization free layer) and the magnetization 20*m* of the upper magnetic layer 20 (the second magnetization free layer) are changed from the initial magnetization direction where the strain does not occur so that the angle with respect to the direction where the tensile stress ts is applied becomes small. In the example illustrated in FIG. 22A, in a case where the tensile stress ts is applied, the relative angle between the magnetization 10*m* of the lower magnetic layer 10 (the first magnetization free layer) and the magnetization 20*m* of the upper magnetic layer 20 (the second magnetization free layer) becomes small, compared with the case of the no-strain initial magnetization direction. Thus, the electrical resistance of the strain sensing element 300 is decreased.

On the other hand, in FIG. 22C, in a case where a compressive strain occurs based on the compressive stress cs in the arrow direction, the magnetization 10*m* of the lower magnetic layer 10 (the first magnetization free layer) and the magnetization 20*m* of the upper magnetic layer 20 (the second magnetization free layer) are changed from the no-strain initial magnetization direction so that the angle with respect to the direction where the compressive stress cs is applied becomes large. In the example illustrated in FIG. 22C, in a case where the compressive stress cs is applied, the relative angle between the magnetization 10*m* of the lower magnetic layer 10 (the first magnetization free layer) and the magnetization 20*m* of the upper magnetic layer 20 (the second magnetization free layer) becomes large, compared with the case of the no-strain initial magnetization direction. Thus, the electrical resistance of the strain sensing element 300 is increased.

As illustrated in FIG. 21B, in the strain sensing element 300 that includes the lower bias layer 110 provided in contact with the lower magnetic layer 10 (the first magnetization free layer) and the upper bias layer 120 provided in contact with the upper magnetic layer 20 (the second magnetization free layer), it is possible to increase the anisotropic magnetic field of the lower magnetic layer 10 (the first magnetization free layer) and the anisotropic magnetic field of the upper magnetic layer 20 (the second magnetization free layer) up to appropriate values, by magnetic coupling from the lower bias layer 110 to the lower magnetic layer 10 (the first magnetization free layer) and magnetic coupling from the upper bias layer 120 to the upper magnetic layer 20 (the second magnetization free layer). By increasing the anisotropic magnetic field of the lower magnetic layer 10 (the first magnetization free layer) and the anisotropic magnetic field of the upper magnetic layer 20 (the second magnetization free layer), it is possible to enhance reversibility of the change of the magnetization 10m of the lower magnetic layer 10 (the first magnetization free layer) and the magnetization 20m of the upper magnetic layer 20 (the second magnetization free layer), and to obtain a high gauge factor. The principle of the enhancement of the reversibility of the change of the magnetizations 10m and 20m of the lower magnetic layer 10 (the first magnetization free layer) and the upper magnetic layer 20 (the second magnetization free layer) with respect to the strain is the same as described in the first embodiment.

In a case where the size of the strain sensing element 300 becomes small, a diamagnetic field occurs inside the lower magnetic layer 10 (the first magnetization free layer) and the upper magnetic layer 20 (the second magnetization free layer) due to the influence of magnetic poles in element end parts of the lower magnetic layer 10 (the first magnetization free layer) and the upper magnetic layer 20 (the second magnetization free layer), and thus, the magnetization 10m of the lower magnetic layer 10 (the first magnetization free layer) and the magnetization 20m of the upper magnetic layer 20 (the second magnetization free layer) may be disturbed. If the magnetization 10m of the lower magnetic layer 10 (the first magnetization free layer) and the magnetization 20m of the upper magnetic layer 20 (the second magnetization free layer) are disturbed, the change of the relative angle between the magnetization 10m of the lower magnetic layer 10 (the first magnetization free layer) and the magnetization 20m of the upper magnetic layer 20 (the second magnetization free layer) due to the strain of the strain sensing element 300 may be reduced. To reduce the diamagnetic field of the lower magnetic layer 10 (the first magnetization free layer) and the upper magnetic layer 20 (the second magnetization free layer) is an important factor for providing a strain sensor of high sensitivity in the strain sensing element 300 having a small size. To improve the anisotropic magnetic fields of the lower magnetic layer 10 (the first magnetization free layer) and the upper magnetic layer 20 (the second magnetization free layer) is also effective to reduce such an influence of the diamagnetic field. Thus, it is possible to realize a high sensitivity of strain sensing in the strain sensing element 300 having the relatively small size. Further, it is possible to provide the strain sensing element 300 with high resolution and high sensitivity.

As illustrated in FIG. 21B, by independently providing the lower bias layer 110 and the upper bias layer 120 with respect to the lower magnetic layer 10 and the upper magnetic layer 20, it is possible to arbitrarily set the initial magnetization directions of the lower magnetic layer 10 and the upper magnetic layer 20.

An example of the strain sensing element 300 according to the second embodiment will be described.

Figure 23:
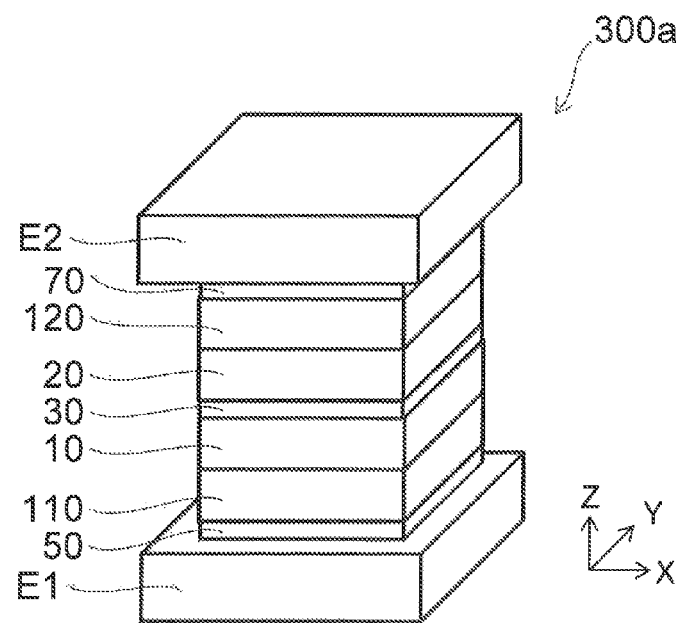
FIG. 23 is a schematic perspective view illustrating a strain sensing element used in the second embodiment.

FIG. 23 is a schematic perspective view illustrating a strain sensing element used in the second embodiment.

As illustrated in FIG. 23, a strain sensing element 300a used in the embodiment includes a first electrode E1, an underlayer 50, a lower bias layer 110, a lower magnetic layer 10, a spacer layer 30, an upper magnetic layer 20, an upper bias layer 120, a capping layer 70, and a second electrode E2. The underlayer 50 is provided between the first electrode E1 and the second electrode E2. The lower bias layer 110 is provided between the underlayer 50 and the second electrode E2. The lower magnetic layer 10 is provided between the lower bias layer 110 and the second electrode E2. The spacer layer 30 is provided between the lower magnetic layer 10 and the second electrode E2. The upper magnetic layer 20 is provided between the spacer layer 30 and the second electrode E2. The upper bias layer 120 is provided between the upper magnetic layer 20 and the second electrode E2. The capping layer 70 is provided between the upper bias layer 120 and the second electrode E2.

The underlayer 50 includes, for example, Ta/Ru. The thickness of the Ta layer (length in the Z-axis direction) is, for example, 3 nm. The thickness of the Ru layer is, for example, 2 nm.

The lower bias layer 110 includes, for example, IrMn (7 nm)/$Fe_{50}Co_{50}$ (3 nm)/Cu (2.5 nm).

The lower magnetic layer 10 (the first magnetization free layer) includes, for example, $Co_{40}Fe_{40}B_{20}$ (4 nm).

The spacer layer 30 includes, for example, MgO (2 nm).

The upper magnetic layer 20 (the second magnetization free layer) includes, for example, $Co_{40}Fe_{40}B_{20}$ (4 nm). The upper bias layer 120 includes, for example, Cu (2.5 nm)/$Fe_{50}Co_{50}$ (2 nm)/Ru (0.9 nm)/$Fe_{50}Co_{50}$ (2 nm)/IrMn (7 nm).

The capping layer 70 includes, for example, Ta (2 nm)/Ru (5 nm).

The material of each layer in the second embodiment may be the same material as in the same layer in the first embodiment. That is, the lower magnetic layer (the first magnetization free layer) and the upper magnetic layer (the second magnetization free layer) of the second embodiment may use the same material as in the magnetization free layer of the first embodiment. The lower bias layer and the upper bias layer of the second embodiment may use the same material as in the bias layer of the first embodiment.

(Details of Bias Layers in Second Embodiment)

FIG. 24A and FIG. 24B are schematic perspective views illustrating the bias layers of the second embodiment.

FIGS. 24A and 24B illustrate examples of variations of structures of the lower bias layer 110 and the upper bias layer 120 that are provided with respect to the stacked body of the lower magnetic layer 10 (the first magnetization free layer)/the spacer layer 30/the upper magnetic layer 20 (the second magnetization free layer), which are examples of variations of structures of the lower bias layer 110 in which the lower magnetic layer 10 is provided between the spacer layer 30 and the lower bias layer 110, and the upper bias layer 120 in which the upper magnetic layer 20 is provided between the spacer layer 30 and the upper bias layer 120.

A lower bias layer 110a illustrated in FIG. 24A includes a lower bias pinning layer 42a, a lower first bias magnetic layer 111a (a first bias magnetic layer), and a lower separating layer 43a. The lower first bias magnetic layer 111a is provided between the lower bias pinning layer 42a and the lower separating layer 43a.

An upper bias layer 120a illustrated in FIG. 24A includes an upper separating layer 43b, an upper first bias magnetic layer 121a (a second bias magnetic layer), an upper first magnetic coupling layer 124a (a first magnetic coupling layer), an upper second bias magnetic layer 121b (a third bias magnetic layer), and an upper bias pinning layer 42b. The upper first bias magnetic layer 121a is provided between the upper separating layer 43b and the upper bias pinning layer 42b. The upper first magnetic coupling layer 124a is provided between the upper first bias magnetic layer 121a and the upper bias pinning layer 42b. The upper second bias magnetic layer 121b is provided between the upper first magnetic coupling layer 124a and the upper bias pinning layer 42b.

The lower first bias magnetic layer 111a is formed of a magnetic material, for example, and the direction of a magnetization 11am is fixed in one direction by the lower bias pinning layer 42a. A bias 10p is applied to the lower magnetic layer 10 (the first magnetization free layer) due to magnetic coupling such as exchange coupling to the lower magnetic layer 10 (the first magnetization free layer) from the lower bias layer 110a in which the magnetization is fixed in one direction.

The upper second bias magnetic layer 121b is formed of a magnetic material, for example, and the direction of a magnetization 21bm is fixed in one direction by the upper bias pinning layer 42b. The upper second bias magnetic layer 121b and the upper first bias magnetic layer 121a in which the magnetizations are fixed in one direction are magnetically coupled to be anti-parallel through the upper magnetic coupling layer 124a, and a bias 20p is applied to the upper magnetic layer 20 (the second magnetization free layer) due to magnetic coupling such as exchange coupling to the upper magnetic layer 20 (the second magnetization free layer) from the upper first bias magnetic layer 121a.

The lower separating layer 43a is formed of a non-magnetic material or the like, for example, and is disposed to adjust the strength of the magnetic coupling between the lower first bias magnetic layer 111a and the lower magnetic layer 10 (the first magnetization free layer) by physically separating the lower first bias magnetic layer 111a from the lower magnetic layer 10 (the first magnetization free layer). Here, it may not be necessary to provide the lower separating layer 43a according to the material of the lower first bias magnetic layer 111a.

The lower separating layer 43a may include, for example, Cu (2.5 nm). The upper separating layer 43b may include, for example, Cu (2.5 nm). The lower first bias magnetic layer 111a may include, for example, $Fe_{50}Co_{50}$ of 3 nm. The upper first bias magnetic layer 121a may include, for example, $Fe_{50}Co_{50}$ of 2 nm. The upper first magnetic coupling layer 124a may include, for example, Ru of 0.9 nm. The upper second bias magnetic layer 121b may include, for example, $Fe_{50}Co_{50}$ of 2 nm. The lower bias pinning layer 42a may include, for example, IrMn of 7 nm. The upper bias pinning layer 42b may include, for example, IrMn of 7 nm.

Each of the lower first bias magnetic layer 111a, the upper first bias magnetic layer 121a and the upper second bias magnetic layer 121b includes, for example, at least one selected from the group consisting of Co, Fe and Ni. As each of the lower first bias magnetic layer 111a, the upper first bias magnetic layer 121a and the upper second bias magnetic layer 121b, an alloy including at least one material selected from these materials may be used. For example, a $Co_xFe_{100-x}$ alloy, a $Ni_xFe_{100-x}$ alloy or a material in which a non-magnetic element is added to these alloys may be used. In the $Co_xFe_{100-x}$ alloy, x is 0 at. % or more and 100 at. % or less. In the $Ni_xFe_{100-x}$ alloy, x is 0 at. % or more and 100 at. % or less.

As each of the lower first bias magnetic layer 111a, the upper first bias magnetic layer 121a and the upper second bias magnetic layer 121b, for example, a $(Co_xFe_{100-x})_{100-y}B_y$ alloy may be used. In the $(Co_xFe_{100-x})_{100-y}B_y$ alloy, x is 0 at. % or more and 100 at. % or less, and y is 0 at. % or more and 30 at. % or less. By using an amorphous alloy of $(Co_xFe_{100-x})_{10-y}B_y$ as each of the lower first bias magnetic layer 111a, the upper first bias magnetic layer 121a and the upper second bias magnetic layer 121b, it is possible to suppress the fluctuation between the strain sensing elements 300 even in a case where the size of the sensing element is small.

It is favorable that the thickness of each of the lower first bias magnetic layer 111a, the upper first bias magnetic layer 121a and the upper second bias magnetic layer 121b be 1.5 nm or more and 5 nm or less, for example. Thus, it is possible to sufficiently obtain the strength of the unidirectional anisotropic magnetic field due to the lower bias pinning layer 42a and the upper bias pinning layer 42b, for example. As each of the lower first bias magnetic layer 111a, the upper first bias magnetic layer 121a and the upper second bias magnetic layer 121b, for example, $Fe_{50}Co_{50}$ of 3 nm may be used.

Each of the lower separating layer 43a and the upper separating layer 43b may include, for example, a non-magnetic material. As each of the lower separating layer 43a and the upper separating layer 43b, a layer including at least one element selected from the group consisting of Cu, Ru, Rh, Ir, V, Cr, Nb, Mo, Ta, W, Rr, Au, Ag, Pt, Pd, Ti, Zr, and Hf may be used. For example, Cu of 5 nm may be used as each of the lower separating layer 43a and the upper separating layer 43b.

The lower bias pinning layer 42a provides unidirectional anisotropy to the lower first bias magnetic layer 111a formed in contact with the lower bias pinning layer 42a to fix the magnetization 111am. The lower bias pinning layer 42a includes, for example, an antiferromagnetic layer. The lower bias pinning layer 42a includes, for example, at least one selected from the group consisting of IrMn, PtMn, PdPtMn and RuRhMn. The thickness of the lower bias pinning layer 42a is set appropriately to provide unidirectional anisotropy of sufficient strength.

The upper bias pinning layer 42b provides unidirectional anisotropy to the upper second bias magnetic layer 121b formed in contact with the upper bias pinning layer 42b to fix the magnetization 121bm. The upper bias pinning layer 42b includes, for example, an antiferromagnetic layer. The upper bias pinning layer 42b includes, for example, at least one selected from the group consisting of IrMn, PtMn, PdPtMn and RuRhMn. The thickness of the upper bias pinning layer 42b is set appropriately to provide unidirectional anisotropy of sufficient strength.

When PtMn or PdPtMn is used as each of the lower bias pinning layer 42a and the upper bias pinning layer 42b, it is favorable that the thickness of each of the lower bias pinning layer 42a and the upper bias pinning layer 42b be 8 nm or more and 20 nm or less. It is more favorable that the thickness of each of the lower bias pinning layer 42a and the upper bias pinning layer 42b be 10 nm or more and 15 nm or less. In a case where IrMn is used as each of the lower bias pinning layer 42a and the upper bias pinning layer 42b, it is possible to provide the unidirectional anisotropy with a thin pinning layer, compared with a case where PtMn is used as each of the lower bias pinning layer 42a and the upper bias pinning layer 42b. In such a case, it is favorable that the thickness of each of the lower bias pinning layer 42a and the upper bias pinning layer 42b be 4 nm or more and 18 nm or less. It is more favorable that the thickness of each of the lower bias pinning layer 42a and the upper bias pinning layer 42b be 5 nm or more and 15 nm or less. Each of the lower bias pinning layer 42a and the upper bias pinning layer 42b includes, for example, an $Ir_{22}Mn_{78}$ layer having a thickness of 7 nm.

A hard magnetic layer may be used as each of the lower bias pinning layer 42a and the upper bias pinning layer 42b. As the hard magnetic layer, for example, CoPt, $(Co_xPt_{100-x})_{100-y}Cr_y$, FePt, or the like may be used. In the case of CoPt, the ratio of Co is 50 at. % or more and 85 at. % or less. In the case of $(Co_xPt_{100-x})_{100-y}Cr_y$, x is 50 at. % or more and 85 at. % or less, and y is 0 at. % or more and 40 at. % or less. In the case of FePt, the ratio of Pt is 40 at. % or more and 60 at. % or less.

The upper first magnetic coupling layer 124a causes antiferromagnetic coupling to occur between the upper first bias magnetic layer 121a and the upper second bias magnetic layer 121b. The upper first magnetic coupling layer 124a forms a synthetic pinned structure. For example, Ru is used as the upper first magnetic coupling layer 124a. It is favorable that the thickness of the upper first magnetic coupling layer 124a be 0.8 nm or more and 1 nm or less. A material other than Ru may be used as the upper first magnetic coupling layer 124a as long as the material can cause sufficient antiferromagnetic coupling to occur between the upper first bias magnetic layer 121a and the upper second bias magnetic layer 121b. The thickness of the upper first magnetic coupling layer 124a may be set to be a thickness of 0.8 nm or more and 1 nm or less that corresponds to the second peak (2nd peak) of Ruderman-Kittel-Kasuya-Yosida (RKKY) coupling. Further, the thickness of the upper first magnetic coupling layer 124a may be set to be a thickness of 0.3 nm or more and 0.6 nm or less that corresponds to the first peak (1st peak) of RKKY coupling. For example, Ru having a thickness of 0.9 nm is used as the upper first magnetic coupling layer 124a. Thus, highly reliable coupling is obtained more stably.

It is favorable that the thickness of each of the upper first bias magnetic layer 121a and the upper second bias magnetic layer 121b be, for example, 1.5 nm or more and 5 nm or less. Thus, for example, it is possible to increase the strength of the unidirectional anisotropic magnetic field due to the upper bias pinning layer 42b. It is favorable that the magnetic film thickness of the upper first bias magnetic layer 121a (the product of a saturation magnetization Bs and a thickness t (Bs·t)) be substantially equal to the magnetic film thickness of the upper second bias magnetic layer 121b.

In a case where the same magnetic material is used in the upper first bias magnetic layer 121a and the upper second bias magnetic layer 121b, it is favorable to match the thickness of the upper first bias magnetic layer 121a with the thickness of the upper second bias magnetic layer 121b. In a case where different magnetic materials are used in the upper first bias magnetic layer 121a and the upper second bias magnetic layer 121b, for example, in a case where $Co_{40}Fe_{40}B_{20}$ is used in the upper first bias magnetic layer 121a and $Co_{75}Fe_{25}$ is used in the upper second bias magnetic layer 121b, in a thin film, the saturation magnetization of $Co_{40}Fe_{40}B_{20}$ is about 1.9 T (teslas), and the saturation magnetization of $Co_{75}Fe_{25}$ is about 2.1 T. For example, in a case where a $Co_{40}Fe_{40}B_{20}$ layer having a thickness of 3 nm is used as the upper first bias magnetic layer 121a, the magnetic film thickness of the upper first bias magnetic layer 121a is 1.9 T×3 nm, which is 5.7 Tnm. The thickness of the upper second bias magnetic layer 121b to obtain a magnetic film thickness that is equal to the above-mentioned magnetic film thickness is 5.7 Tnm/2.1 T, which is 2.7 nm. In such a case, it is favorable that the upper second bias magnetic layer 121b includes a $Co_{75}Fe_{25}$ layer having a thickness of about 2.7 nm.

FIG. 24B is a schematic perspective view illustrating another bias layer of the second embodiment.

A lower bias layer 110b illustrated in FIG. 24B includes a lower bias pinning layer 42a, a lower third bias magnetic layer 111c, a lower second magnetic coupling layer 114b (a second magnetic coupling layer), a lower second bias magnetic layer 111b (a fourth bias magnetic layer), a lower first magnetic coupling layer 114a, a lower first bias magnetic layer 111a, and a lower separating layer 43a. The lower third bias magnetic layer 111c is provided between the lower bias pinning layer 42a and the lower separating layer 43a. The lower second magnetic coupling layer 114b is provided between the lower third bias magnetic layer 111c and the lower separating layer 43a. The lower second bias magnetic layer 111b is provided between the lower second magnetic coupling layer 114b and the lower separating layer 43a. The lower first magnetic coupling layer 114a is provided between the lower second bias magnetic layer 111b and the lower separating layer 43a. The lower first bias magnetic layer 111a is provided between the lower first magnetic coupling layer 114a and the lower separating layer 43a.

An upper bias layer 120b illustrated in FIG. 24B includes an upper separating layer 43b, the upper first bias magnetic layer 121a, an upper first magnetic coupling layer 124a, the upper second bias magnetic layer 121b, and the upper bias pinning layer 42b. The upper first bias magnetic layer 121a is provided between the upper separating layer 43b and the upper bias pinning layer 42b. The upper first magnetic coupling layer 124a is provided between the upper first bias magnetic layer 121a and the upper bias pinning layer 42b. The upper second bias magnetic layer 121b is provided between the upper first magnetic coupling layer 124a and the upper bias pinning layer 42b.

In FIG. 24A, the bias magnetic layer of a single layer is provided in the lower bias layer 110a, but in FIG. 24B, the bias magnetic layers of a three-layer structure are provided in the lower bias layer 110b through the lower first magnetic coupling layer 114a and the lower second magnetic coupling layer 114b. The plural bias magnetic layers may be configured so that the magnetization directions of the adjacent bias magnetic layers are opposite through the magnetic coupling layers. By setting the magnetization directions to be anti-parallel using the plural bias magnetic layers as described above, it is possible to suppress the stray magnetic field from the bias magnetic layers to the outside, and to suppress magnetic interference other than bias application due to exchange coupling to the magnetization free layer.

In FIG. 24B, since the plural bias magnetic layers are used in both of the lower bias layer 110b and the upper bias layer 120b, it is possible to suppress the stray magnetic field from the bias magnetic layers to the outside by both of the bias layers (the lower bias layer 110b and the upper bias layer 120b).

As illustrated in the lower bias layer 110b in FIG. 24B, in a case where three bias magnetic layers are used, a magnetization 111am of the lower first bias magnetic layer 111a and a magnetization 111cm of the lower third bias magnetic layer 111c are directed in the same direction, and only a magnetization 111bm of the lower second bias magnetic layer 111b is directed in the opposite direction. In this manner, in a case where odd-numbered plural bias magnetic layers are used, from the viewpoint of reduction of the leakage magnetic field, it is favorable that the sum of the magnetic film thicknesses of the bias magnetic layers directed in the same direction be equal to the sum of the magnetic film thicknesses of the bias magnetic layers directed in the opposite direction. For example, as illustrated in FIG. 24B, in a case where three bias magnetic layers are used, it is favorable that the sum of the magnetic film thickness of the lower first bias magnetic layer 111a and the magnetic film thickness of the lower third bias magnetic layer 111c be set to be equal to the magnetic film thickness of the lower second bias magnetic layer 111b.

The materials of the respective layers included in FIG. 24B may use the same materials as in FIG. 24A.

The lower bias pinning layer 42a may include, for example, IrMn of 7 nm. The lower third bias magnetic layer 111c may include, for example, $Fe_{50}Co_{50}$ of 2 nm. The lower second bias magnetic coupling layer 114b may include, for example, Ru of 0.9 nm. The lower first bias magnetic layer 111a may include, for example, $Fe_{50}Co_{50}$ of 4 nm. The lower first magnetic coupling layer 114a may include, for example, Ru of 0.9 nm. The lower first bias magnetic layer 111a may include, for example, $Fe_{50}Co_{50}$ of 2 nm. The lower separating layer 43a may include, for example, Cu of 2.5 nm.

The upper separating layer 43b may include, for example, Cu of 2.5 nm. The upper first bias magnetic layer 121a may include, for example, $Fe_{50}Co_{50}$ of 2 nm. The upper first magnetic coupling layer 124a may include, for example, Ru of 0.9 nm. The upper second bias magnetic layer 121b may include, for example, $Fe_{50}Co_{50}$ of 2 nm. The upper bias pinning layer 42b may include, for example, IrMn of 7 nm.

In FIG. 24A, a case where the bias magnetic layer of a single layer is used in the lower bias layer 110a and the bias magnetic layers of a two-layer structure are used in the upper bias layer 120a is described as an example. In FIG. 24B, a case where the bias magnetic layers of a three-layer structure are used in the lower bias layer 110b and the bias magnetic layers of a two-layer structure are used in the upper bias layer 120b is described as an example. It is possible to appropriately adjust the number of bias magnetic layers included in the lower bias layers 110a and 110b and the upper bias layers 120a and 120b.

The bias layer may include four or more bias magnetic layers.

In a case where the number of the bias magnetic layers respectively included in the lower bias layer 110 and the upper bias layer 120 is set to odd-even or even-odd, the directions of the biases applied to the lower magnetic layer 10 (the first magnetization free layer) and the upper magnetic layer 20 (the second magnetization free layer) become anti-parallel. In a case where the number of the bias magnetic layers respectively included in the lower bias layer 110 and the upper bias layer 120 is set to odd-odd or even-even, the directions of the biases applied to the lower magnetic layer 10 (the first magnetization free layer) and the upper magnetic layer 20 (the second magnetization free layer) become parallel. In either case, it is possible to achieve the function of a strain sensor. In a case where the directions of the biases respectively applied to the lower magnetic layer 10 (first magnetization free layer) and the upper magnetic layer 20 (second magnetization free layer) are anti-parallel, it is possible to obtain an operation in which the anti-parallel magnetization alignments are closed like scissors due to strain, and to realize a high gauge factor, which is more favorable.

Here, in the case of the tunneling type strain sensing element in which an insulating layer is used in the spacer layer 30, it is favorable that the directions of the biases applied to the lower magnetic layer 10 (the first magnetization free layer) and the upper magnetic layer 20 (the second magnetization free layer) be anti-parallel to each other from the viewpoint of increasing the electrical resistance change. The reason is as follows: That is, since the electrical resistance change is large in a case where the relative angle between a pinning layer and a free layer changes between 90° and 180° in the tunneling type strain sensing element, compared with a case where the relative angle between the pinning layer and the free layer changes between 0° and 90°, when the strain sensing element is driven between 90° and 180° as a strain sensor, a high gauge factor is easily obtained. As the relative angle between the pinning layer and the free layer is close to 180°, the electrical resistance change per unit relative angle change becomes large. Accordingly, it is favorable that the number of bias magnetic layers included in each of the lower magnetic layer 10 (the first magnetization free layer) and the upper magnetic layer 20 (the second magnetization free layer) be set to odd-even or even-odd.

As a fifth example according to the embodiment, the strain sensing element 300 having the following structure is manufactured.

Fifth Example

Underlayer 50: Ta (1 nm)/Ru (2 nm)
Lower bias layer 110: $Ir_{22}Mn_{78}$ (7 nm)/$Fe_{50}Co_{50}$ (3 nm)/Cu (2.5 nm)
Lower magnetic layer 10 (First magnetization free layer): $Co_{40}Fe_4B_{20}$ (4 nm)
Spacer layer 30: MgO (2 nm)
Upper magnetic layer 20 (Second magnetization free layer): $Co_{40}Fe_{40}B_{20}$ (4 nm)
Upper bias layer 120: Cu (2.5 nm)/$Fe_{50}Co_{50}$ (2 nm)/Ru (0.9 nm)/$Fe_{50}Co_{50}$ (2 nm)/IrMn (7 nm)
Capping layer 70: Ta (2 nm)/Ru (5 nm)

The structure of the strain sensing element 300 of the fifth example is the same as the structure of the strain sensing element 300a illustrated in FIG. 23. The structure of the lower bias layer 110 is the same as the structure of the lower bias layer 110a illustrated in FIG. 24A. The lower bias layer 110 includes the lower bias pinning layer 42a/the lower first bias magnetic layer 111a/the lower separating layer 43a. The structure of the upper bias layer 120 is the same as that of the upper bias layer 120a illustrated in FIG. 24A. The upper bias layer 120 includes the upper separating layer 43b/the upper first bias magnetic layer 121a/the upper first magnetic coupling layer 124a/the upper second bias magnetic layer 121b/the upper bias pinning layer 42b.

As a second comparative example, a strain sensing element having the following structure is manufactured, Second Comparative Example Underlayer 50: Ta (1 nm)/Ru (15 nm)
Lower magnetic layer 10 (first magnetization free layer): $Co_{40}Fe_{40}B_{20}$ (4 nm)
Spacer layer 30: MgO (2 nm)
Upper magnetic layer 20 (second magnetization free layer): $Co_{40}Fe_{40}B_{20}$ (4 nm)
Capping layer 70: Cu (15 nm)/Ta (2 nm)/Ru (5 nm)

In the second comparative example, the bias layer is not provided.

With respect to a stacked body of the fifth example, annealing is performed while a magnetic field of 6500 Oe (oersteds) is applied for one hour at 320° C., after molding. Thus, pinning of magnetizations of the lower bias layer 110 and the upper bias layer 120 is performed.

FIGS. 25A to 25D are graphs illustrating examples of results of magnetic characteristics before the stacked body of the fifth example is element-processed.

FIG. 25A illustrates an example of a B—H loop obtained by evaluating a magnetic field applied in a direction where the annealing in the magnetic field is performed as a positive magnetic field, in the fifth example. FIG. 25B illustrates an example of a B—H loop obtained by evaluation of a magnetic field applied in a direction, in the plane, perpendicular to the direction where the annealing in the magnetic field is performed, in the fifth example. FIG. 25C illustrates an example of a B—H loop obtained by evaluating a magnetic field applied in a direction where the annealing in the magnetic field is performed as a positive magnetic field, in the second comparative example. FIG. 25D illustrates an example of a B—H loop obtained by evaluation of a magnetic field applied in a direction, in the plane, perpendicular to the direction where the annealing in the magnetic field is performed, in the second comparative example.

In the B—H loop illustrated in FIG. 25A, it can be understood that one loop shape of a magnetization easy axis with a satisfactory squareness is obtained in each of a negative side magnetic field and a positive side magnetic field, and the shapes are anti-parallel in a zero magnetic field. In the B—H loop illustrated in FIG. 25B, a loop shape of a typical magnetization hard axis is obtained. As a result, it can be understood that in-plane induced magnetic anisotropy in which the direction of the annealing in the magnetic field is used as the magnetization easy axis is obtained in each magnetization free layer of the fifth example.

In the B—H loop illustrated in FIG. 25C, a loop shape of a magnetization easy axis with a satisfactory squareness is obtained. In the B—H loop illustrated in FIG. 25B, a loop shape of a typical magnetization hard axis is obtained. As a result, it can be understood that in-plane induced magnetic anisotropy in which the direction of the annealing in the magnetic field is used as the magnetization easy axis is obtained in the magnetization free layer. As understood from FIG. 25C, in the second comparative example in which the bias layer is not provided, the lower magnetic layer 10 and the upper magnetic layer 20 are reversed at the same time and are parallel to each other in a zero magnetic field. An anisotropic magnetic field $H_k$ indicating the strength of the in-plane induced magnetic anisotropy is estimated as 16.9 Oe, which is an average value of the lower magnetic layer 10 and the upper magnetic layer 20.

From the B—H loop in FIG. 25A, the lower magnetic field 10 (the first magnetization free layer) is biased to the negative magnetic field side. Here, $H_{shift}$ is estimated as −8.8 Oe. The coercivity $H_c$ is estimated as 3.4 Oe. From the BH loop in FIG. 25A, the upper magnetic field 20 (the second magnetization free layer) is biased to the positive magnetic field side. Here, $H_{shift}$ is estimated as 10.5 Oe. The coercivity $H_c$ is estimated as 3.1 Oe.

The coercivity is a characteristic index indicating the easiness of magnetization rotation. The coercivity of about 3 Oe may be a value in which the magnetization rotation due to the inverse-magnetostriction effect sufficiently and easily occurs. As a result of the evaluation of the magnetostriction constant of the fifth example, the average value of the magnetostriction constants of the magnetization free layers of the two-layer structure is calculated as 20 ppm. This value may be a sufficiently high value for occurrence of the magnetization rotation due to high strain. An anisotropic magnetic field $H_k$ calculated from the BH loop illustrated in FIG. 25B relating to the strength of the induced magnetic anisotropy is estimated as 18.7 Oe. Thus, it is confirmed that the anisotropic magnetic field is improved by providing the bias layer, compared with the second comparative example.

From the results of FIGS. 25A to 25D, the configuration of the magnetization free layer of the fifth example is the same as the configuration of the magnetization free layer of the second comparative example. The coercivity of the fifth example is the same as the coercivity of the second comparative example. The magnetostriction constant of the fifth example is the same as the magnetostriction constant of the second comparative example.

In the fifth example, it can be understood that the anisotropic magnetic field is improved by providing the bias layer, compared with the second comparative example. In the fifth example, the bias is applied to the lower magnetic layer 10 from the lower bias layer 110. The bias is applied to the upper magnetic layer 20 from the upper bias layer 120. The direction of the bias applied to the lower magnetic layer 10 from the lower bias layer 110 is anti-parallel to the direction of the bias applied to the upper magnetic layer 20 from the upper bias layer 120. Thus, it can be understood that the magnetization 10m of the lower magnetic layer 10 (the first magnetization free layer) is anti-parallel to the magnetization 20m of the upper magnetic layer 20 (the second magnetization free layer) in a zero magnetic field.

The stacked body of the fifth example is processed by photolithography and milling as a Current-perpendicular-to-the-plane (CPP) element. The element size of the Current-perpendicular-to-the-plane (CPP) element is set to 20 m×20 μm.

FIGS. 26A to 26D are graphs illustrating examples of results of strain sensor characteristics of the strain sensing element of the fifth example.

Evaluation of the strain sensor characteristics illustrated in FIGS. 26A to 26D is performed by substrate bending method. Strain application is performed for a wafer obtained by cutting a wafer of the strain sensing element 300 in a stripe shape, by a four-point bending method using a knife edge. A road cell is additionally provided to the knife edge that bends the stripe-shaped wafer, and strain applied to the strain sensing element 300 on a front surface of the wafer is calculated by the load measured by the load cell. In the calculation of the strain, a general logical expression of a two-side support beam represented by the above-mentioned expression (1) described with reference to FIGS. 10A to 10E is used. The direction of the strain application is as described with reference to FIGS. 10A to 10E.

In the example illustrated in FIG. 26A, with respect to the strain sensing element 300 of the fifth example having an element size of 20 μm×20 μm, the strain applied to the strain sensing element 300 is set as a fixed value with an interval of 0.2 (‰) between −0.8 (‰) and 0.8 (‰). FIG. 26A illustrates respective examples of results obtained by measuring magnetic field dependency of electrical resistance in respective strains. An external magnetic field direction at the time of measurement is a direction perpendicular to the direction of magnetization of each bias layer in the plane. From FIG. 26A, it can be understood that the shape of the R—H loop is changed by the value of the applied strain. This means that the in-plane magnetic anisotropy of the magnetization free layer is changed by the inverse-magnetostriction effect.

FIGS. 26B to 26D represent changes of electrical resistances in the strain sensing element 300 of the fifth example when an external magnetic field is fixed and strain is continuously swept between −0.8 (‰) and 0.8 (‰). The strain is swept from −0.8 (‰) to 0.8 (‰), and then, is swept from 0.8 (‰) to −0.8 (‰). These results represent the strain sensor characteristics. In FIG. 26B, the evaluation is performed by applying an external magnetic field of 5 Oe. In FIG. 26C, an external magnetic field of 2 Oe is applied to perform the evaluation. In FIG. 26D, the evaluation is performed by applying an external magnetic field of 0 Oe.

In the strain sensing element 300 of the embodiment, it is possible to obtain a high gauge factor by applying an appropriate bias magnetic field. The external magnetic field may also be applied by providing a hard bias to a side wall of the strain sensing element. In the strain sensing element 300 of the fifth example, the evaluation is performed by simply applying the external magnetic field using a coil. The gauge factor of the fifth example is estimated from the change of the electrical resistance with respect to the strain, from FIGS. 26B to 26D.

The gauge factor is represented by the above-mentioned expression (2) with reference to FIGS. 10A to 10E. From FIG. 26B, in the fifth example, the gauge factor obtained when the external magnetic field is 5 Oe is 1713. From FIG. 26C, in the fifth example, the gauge factor obtained when the external magnetic field is 2 Oe is 2587. From FIG. 26D, in the fifth example, the gauge factor obtained when the external magnetic field is 0 Oe is 3570. From these results, in the fifth example, the maximum gauge factor (3570) is obtained when the bias magnetic field is 0 Oe.

From the results of FIGS. 26A to 26D, in the fifth example in which the bias layer is provided, it is confirmed that the high gauge factor is obtained when the external magnetic field is zero. It is considered that the reason is because appropriate anti-parallel biases are applied to the lower magnetic layer 10 (the first magnetization free layer) and the upper magnetic layer 20 (the second magnetization free layer) in the zero magnetic field by providing the bias layer and the reversibility of the strain sensor characteristics can thus be enhanced. It is considered that the enhancement of the reversibility as the bias layer is provided is based on the same principle described above with reference to FIGS. 13A to 13F. It is considered that this is because a reversible strain sensor characteristic is obtained without an extra bias magnetic field by the enhancement of the anisotropic magnetic field.

As a sixth example according to the embodiment, the strain sensing element 300 having the following structure is manufactured.

Sixth Example

Underlayer 50: Ta (1 nm)/Ru (2 nm)
Lower bias layer 110: $Ir_{22}Mn_{78}$ (7 nm)/$Fe_{50}Co_{50}$ (2 nm)/Ru (0.9 nm)/$Fe_{50}Co_{50}$ (4 nm)/Ru (0.9 mm)/$Fe_{50}Co_{50}$ (2 nm)/Cu (2.5 nm)
Lower magnetic layer 10 (first magnetization free layer): $Co_{40}Fe_{50}B_{20}$ (4 nm)
Spacer layer 30: MgO (2 nm)
Upper magnetic layer 20 (second magnetization free layer): $Co_{40}Fe_{40}B_{20}$ (4 nm)
Upper bias layer 120: Cu (2.5 nm)/$Fe_{50}Co_{50}$ (2 nm)/Ru (0.9 nm)/$Fe_{50}Co_{50}$ (2 nm)/IrMn (7 nm)
Capping layer 70: Ta (2 nm)/Ru (5 nm)

The structure of the strain sensing element 300 of the sixth example is the same as the structure of the strain sensing element 300a illustrated in FIG. 23. The structure of the lower bias layer 110 is the same as the structure of the lower bias layer 110b illustrated in FIG. 24B. The lower bias layer 110 includes the lower bias pinning layer 42a/the lower third bias magnetic layer 111c/the lower second magnetic coupling layer 114b/the lower second bias magnetic layer 111b/the lower first magnetic coupling layer 114a/the lower first bias magnetic layer 111a/the lower separating layer 43a. The structure of the upper bias layer 120 is the same as the structure of the upper bias layer 120b illustrated in FIG. 24B. The upper bias layer 120 includes the upper separating layer 43b/the upper first bias magnetic layer 121a/the upper first magnetic coupling layer 124a/the upper second bias magnetic layer 121b/the upper bias pinning layer 42b. The sixth example is different from the fifth example in that the lower bias layer 110 of the fifth example includes the bias magnetic layer of the single layer, whereas the lower bias layer 110 of the sixth example includes the bias magnetic layers of a three-layer structure.

FIGS. 27A to 27D are graphs illustrating examples of results of strain sensor characteristics of the strain sensing element of the sixth example.

Similar to the fifth example, the evaluation of the strain sensor characteristics is performed.

In the example illustrated in FIG. 27A, with respect to the strain sensing element 300 of the sixth example having an element size of 20 μm×20 μm, the strain applied to the strain sensing element 300 is set as a fixed value with an interval of 0.2 (‰) between −0.8 (‰) and 0.8 (‰). FIG. 27A illustrates respective examples of results obtained by measuring magnetic field dependency of electrical resistance in respective strains. An external magnetic field direction at the time of measurement is a direction perpendicular to the direction of magnetization of each bias layer in the plane. From FIG. 27A, it can be understood that the shape of the R—H loop is changed by the value of the applied strain. This means that the in-plane magnetic anisotropy of the magnetization free layer is changed by the inverse-magnetostriction effect.

FIGS. 27B to 27D represent changes of electrical resistances in the strain sensing element 300 of the sixth example when an external magnetic field is fixed and strain is continuously swept between −0.8 (‰) and 0.8 (‰). The strain is swept from −0.8 (‰) to 0.8 (‰), and then, is swept from 0.8 (‰) to −0.8 (‰). These results represent the strain sensor characteristics. In FIG. 27D, the evaluation is performed by applying an external magnetic field of 0 Oe.

In the strain sensing element 300 of the embodiment, it is possible to obtain a high gauge factor by applying an appropriate bias magnetic field. The external magnetic field may also be applied by providing a hard bias to a side wall of the strain sensing element. In the strain sensing element 300 of the sixth example, the evaluation is performed by simply applying the external magnetic field using a coil. The gauge factor of the sixth example is estimated from the change of the electrical resistance with respect to the strain, from FIGS. 27B to 27D.

The gauge factor is represented by the above-mentioned expression (2) with respect to FIGS. 10A to 10E. From FIG. 27B, in the sixth example, the gauge factor obtained when the external magnetic field is 5 Oe is 2276. From FIG. 27C, in the sixth example, the gauge factor obtained when the external magnetic field is 2 Oe is 4270. From FIG. 27D, in the sixth example, the gauge factor obtained when the external magnetic field is 0 Oe is 4980. From these results, in the sixth example, the maximum gauge factor (4980) is obtained when the bias magnetic field is 0 Oe.

The gauge factor of the sixth example is higher than the gauge factor of the fifth example. It is considered that in the sixth embodiment, since both of the lower bias layer 110 and the upper bias layer 120 include the plural bias magnetic layers, it is possible to reduce the influence of the leakage of magnetic field from the bias magnetic layers, and thus, to confirm a high gauge factor. Thus, it is favorable to set the number of the bias layers to plural layers.

As a seventh example according to the embodiment, the strain sensing element 300 having the following structure is manufactured.

Seventh Example

Underlayer 50: Ta (1 nm)/Ru (2 nm)
Lower bias layer 110: $Ir_{22}Mn_{78}$ (7 nm)/$Fe_{50}Co_{50}$ (3 nm)/Cu (2.5 nm)
Lower magnetic layer 10 (first magnetization free layer): $Fe_{80}B_{20}$ (4 nm)/$Co_{40}Fe_{40}B_{20}$ (0.5 nm)

Spacer layer 30: MgO (2 nm)

Upper magnetic layer 20 (second magnetization free layer): $Co_{40}Fe_{40}B_{20}$ (0.5 nm)/$Fe_{80}B_{20}$ (4 nm)

Upper bias layer 120: Cu (2.5 nm)/$Fe_{50}Co_{50}$ (2 nm)/Ru (0.9 nm)/$Fe_{50}Co_{50}$ (2 nm)/IrMn (7 nm)

Capping layer 70: Ta (2 nm)/Ru (5 nm)

The structure of the strain sensing element 300 of the seventh example is the same as the structure of the strain sensing element 300a illustrated in FIG. 23. The structure of the lower bias layer 110 is the same as the structure of the lower bias layer 110a illustrated in FIG. 24A. The lower bias layer 110 includes the lower bias pinning layer 42a/the lower first bias magnetic layer 111a/the lower separating layer 43a. The structure of the upper bias layer 120 is the same as the structure of the upper bias layer 120a illustrated in FIG. 24A. The upper bias layer 120a includes the upper separating layer 43b/the upper first bias magnetic layer 121a/the upper first magnetic coupling layer 124a/the upper second bias magnetic layer 121b/the upper bias pinning layer 42b. The seventh example is different from the fifth example in that the lower magnetic layer 10 and the upper magnetic layer 20 in the fifth example include $Co_{40}Fe_{40}B_{20}$ (4 nm), whereas the lower magnetic layer 10 and the upper magnetic layer 20 in the seventh example include $Co_{40}Fe_{40}B_{20}$ (0.5 nm)/$Fe_{80}B_{20}$ (4 nm).

As a result of evaluation of the magnetic characteristic of the magnetization free layer of the seventh example including $Fe_{40}B_{20}$ (0.5 nm)/$Fe_{80}B_{20}$ (4 nm), a coercivity $H_c$ is 3 Oe, and a magnetostriction constant is 26 ppm. The coercivity of the seventh example is smaller than $Co_{40}Fe_{40}B_{20}$ (4 nm) of the fifth example. The magnetostriction constant of the seventh example is larger than the magnetostriction constant of the fifth example. By using the amorphous magnetic layer including an alloy containing Fe and B as the magnetization free layer as described above, it is possible to achieve a low $H_c$ and a high magnetorestriction constant.

FIGS. 28A to 28D are graphs illustrating examples of results of strain sensor characteristics of the strain sensing element of the seventh example.

Similar to the fifth example, the evaluation of the strain sensor characteristics is performed.

Figure 28A:
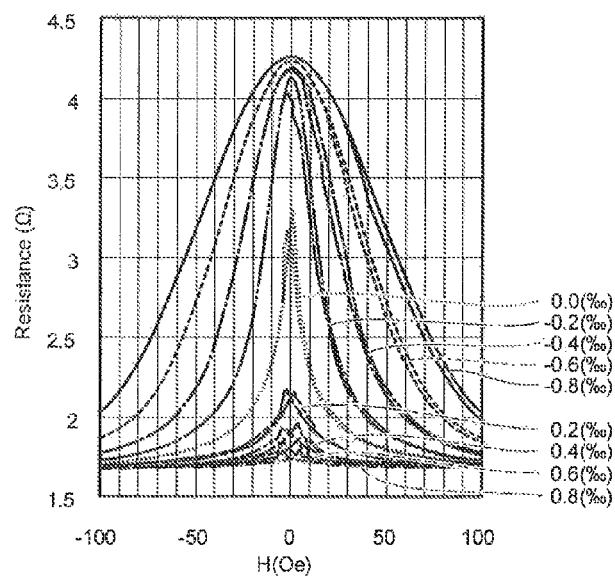
FIGS. 28A to 28D are graphs illustrating examples of results of strain sensor characteristics of the strain sensing element of the seventh example.

In the example illustrated in FIG. 28A, with respect to the strain sensing element 300 of the seventh example having an element size of 20 µm×20 µm, the strain applied to the strain sensing element 300 is set as a fixed value with an interval of 0.2 (‰) between −0.8 (‰) and 0.8 (‰). FIG. 28A illustrates respective examples of results obtained by measuring magnetic field dependency of electrical resistance in respective strains. An external magnetic field direction at the time of measurement is a direction perpendicular to the direction of magnetization of each bias layer in the plane. From FIG. 28A, it can be understood that the shape of the R—H loop is changed by the value of the applied strain. This means that the in-plane magnetic anisotropy of the magnetization free layer is changed by the inverse-magnetostriction effect.

Figure 28B:
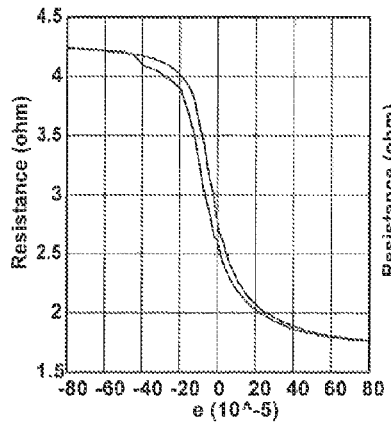
Figure 28C:
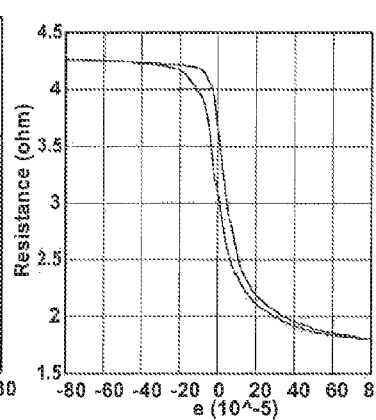
Figure 28D:
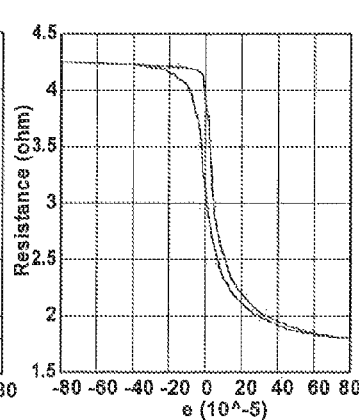

FIGS. 28B to 28D represent changes of electrical resistances in the strain sensing element 300 of the seventh example when an external magnetic field is fixed and strain is continuously swept between −0.8 (‰) and 0.8 (‰). The strain is swept from −0.8 (‰) to 0.8 (‰), and then, is swept from 0.8 (‰) to −0.8 (‰). These results represent the strain sensor characteristics. In FIG. 28B, the evaluation is performed by applying an external magnetic field of 5 Oe. In FIG. 28C, the evaluation is performed by applying an external magnetic field of 2 Oe. In FIG. 28D, the evaluation is performed by applying an external magnetic field of 0 Oe.

In the strain sensing element 300 of the embodiment, it is possible to obtain a high gauge factor by applying an appropriate bias magnetic field. The external magnetic field may also be applied by providing a hard bias to a side wall of the strain sensing element. In the strain sensing element 300 of the seventh example, the evaluation is performed by simply applying the external magnetic field using a coil. The gauge factor of the seventh example is estimated from the change of the electrical resistance with respect to the strain, from FIGS. 28B to 28D.

The gauge factor is represented by the above-mentioned expression (2) with respect to FIGS. 10A to 10E. From FIG. 28B, in the seventh example, the gauge factor obtained when the external magnetic field is 5 Oe is 3086. From FIG. 28C, in the seventh example, the gauge factor obtained when the external magnetic field is 2 Oe is 4418. From FIG. 28D, in the seventh example, the gauge factor obtained when the external magnetic field is 0 Oe is 5290. From these results, in the seventh example, the maximum gauge factor (5290) is obtained when the bias magnetic field is 0 Oe.

The gauge factor of the seventh example is higher than the gauge factor of the fifth example. This is because in the seventh example, the magnetization free layer including the Fe—B alloy in which the coercivity $H_c$ is low and also the magnetostriction constant is high is used in the lower magnetic layer 10 and the upper magnetic layer 20.

FIGS. 29A to 29D are schematic diagrams illustrating another strain sensing element according to the embodiment.

In the above-described embodiment, a case where the direction of the bias applied to the lower magnetic layer 10 (the first magnetization free layer) from the lower bias layer 110 is parallel or anti-parallel to the direction of the bias applied to the upper magnetic layer 20 (the second magnetization free layer) from the upper bias layer 120 is described. Here, the bias direction is not limited to the parallel and anti-parallel directions. The bias may be applied in an arbitrary direction.

Figure 29A:
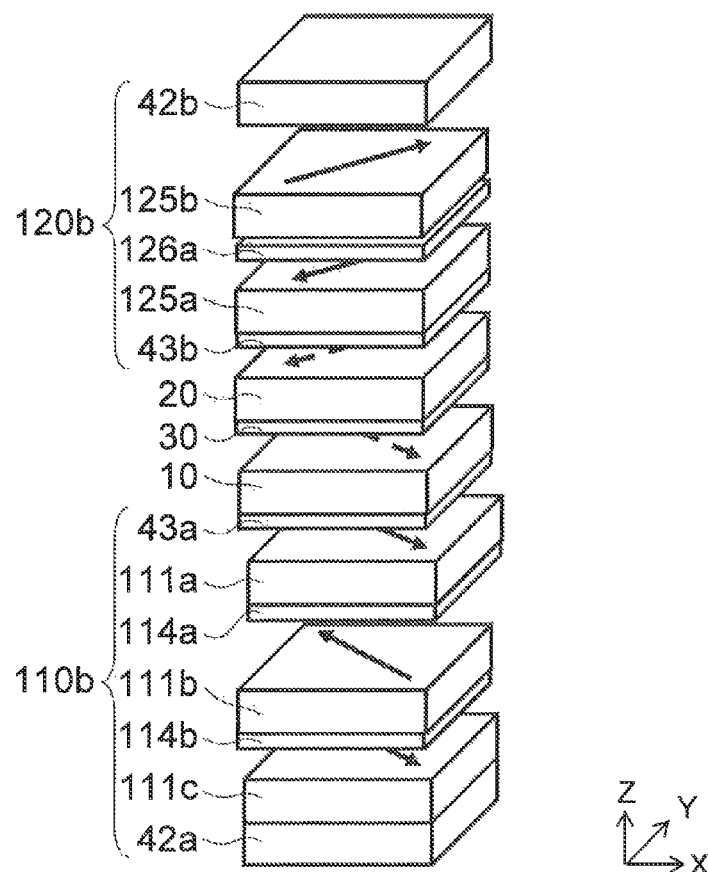
FIGS. 29A to 29D are schematic diagrams illustrating another strain sensing element according to the embodiment.
Figure 29B:
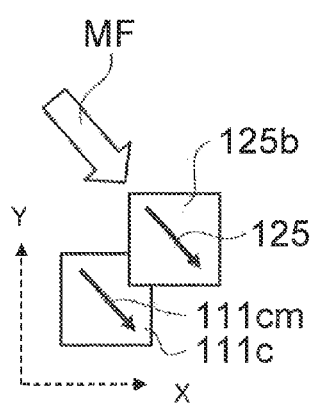

For example, as illustrated in FIG. 29A, a relative angle between the bias direction of the lower bias layer 110b and the bias direction of the upper bias layer 120b may be set to 90°. Such a setting of the bias direction may be performed according to two-stage annealing in a magnetic field as illustrated in FIGS. 29B and 29C, selection of the material used in the lower bias pinning layer 42a and selection of the material used in the upper bias pinning layer 42b.

Anti-ferromagnetic materials used in the lower bias pinning layer 42a and the upper bias pinning layer 42b have different temperatures at which the magnetization pinning occurs, according to their compositions. For example, an ordered alloy based material such as PtMn has a high temperature at which the magnetization pinning occurs, compared with a material such as IrMn in which the magnetization pinning irregularly occurs. For example, the annealing in the magnetic field of two stages as illustrated in FIGS. 29B and 29C is performed using PtMn in the lower bias pinning layer 42a of a strain sensing element 300b illustrated in FIG. 29A and using IrMn in the upper bias pinning layer 42b. Then, during annealing at 320° for ten hours, illustrated in FIG. 29B, the lower third bias magnetic layer 111c in contact with the lower bias pinning layer 42a is fixed in a lower right direction. The upper second bias magnetic layer 125b in contact with the upper bias pinning layer 42b is once fixed in the lower right direction.

Figure 29C:
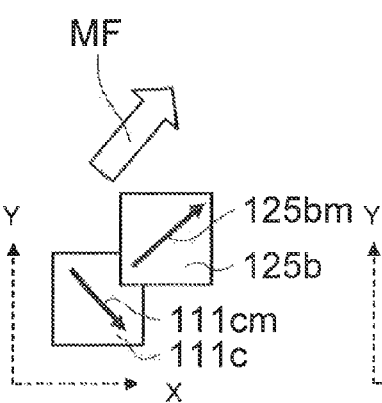
Figure 29D:
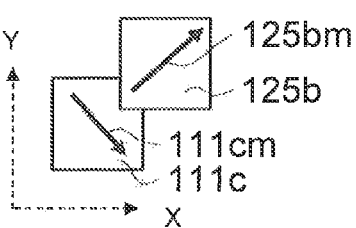

Then, for example, if the direction of a magnetic field MF is changed during annealing at 250° C. for one hour as illustrated in FIG. 29C, it is possible to perform setting such that while a magnetization 111cm of the lower first bias magnetic layer 111c in contact with the lower bias pinning layer 42a is directed in a lower right direction, the magnetization 125bm of the upper second bias magnetic layer 125b in contact with the upper bias pinning layer 42b is directed in the upper right direction. The directions of the magnetizations 111cm and 125bm are also maintained after returning to room temperature, as illustrated in FIG. 29D.

In this manner, it is possible to arbitrarily set the bias direction to the lower magnetic layer 10 (the first magnetization free layer) and the upper magnetic layer 20 (the second magnetization free layer) according to the annealing method in the magnetic field, the material selection of the lower bias pinning layer 42a and the material selection of the upper bias pinning layer 42b. Here, as described above, in the case of using the tunneling type strain sensing element in which the insulating layer is used in the spacer layer 30, it is more favorable that the bias direction to the lower magnetic layer 10 (the first magnetization free layer) be anti-parallel to the bias direction to the upper magnetic layer 20 (the second magnetization free layer). Specifically, it is favorable to set the relative angle between the bias direction to the lower magnetic layer 10 (the first magnetization free layer) and the bias direction to the upper magnetic layer 20 (the second magnetization free layer) to 90° or more and 270° or less, and it is more favorable to set the relative angle to 135° or more and 225° or less.

In order to broaden a dynamic range of the resistance changing strain, it is favorable to set the relative angle between the bias direction to the lower magnetic layer 10 (the first magnetization free layer) and the bias direction of the upper magnetic layer 20 (the second magnetization free layer) to 45° or more and 135° or less.

Although not shown, the setting of the arbitrary bias directions as illustrated in FIGS. 29A to 29D may also be available using a bias layer that does not use a bias pinning layer, similar to the relationship between FIGS. 16A to 16D and FIGS. 17A to 17D.

Further, in the second embodiment, similar to FIG. 18 of the first embodiment and FIG. 19 of the first embodiment, it is possible to use an imbedded insulating layer and a hard bias around the strain sensing element.

Figure 30:
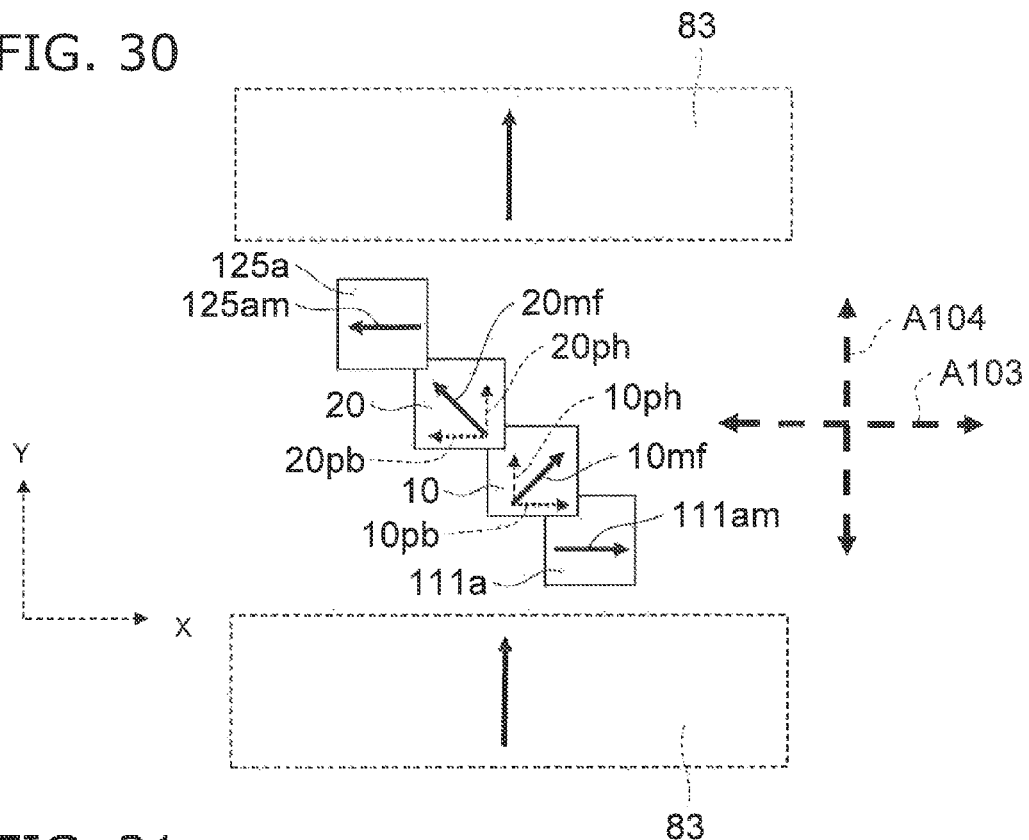
FIG. 30 is a schematic plan view illustrating an example of a bias direction of each bias layer and a bias direction of a hard bias in the second embodiment.

FIG. 30 is a schematic plan view illustrating an example of a bias direction of each bias layer and a bias direction of a hard bias in the second embodiment.

In the example in FIG. 30, the bias direction of the upper bias layer 120 is set to be anti-parallel to the bias direction of the lower bias layer 110. The direction of a magnetic field bias of the hard bias layer 83 with respect to the upper first bias magnetic layer 125a is set to 90° (or 270°). The direction of a magnetic field bias of the hard bias layer 83 with respect to the lower first bias magnetic layer 111a is set to 90° (or 270°).

An initial magnetization 10mf (direction of the bias 1op) of the lower magnetic layer 10 (the first magnetization free layer) is set to be between 0° and 90°, for example, 45° from interference between the bias 10pb from the lower first bias magnetic layer 111a and the magnetic field bias 10ph from the hard bias layer 83. The initial magnetization 20mf (direction of the bias 20p) of the upper magnetic layer 20 (the second magnetization free layer) is set to be between 90° and 180°, for example, 135° from interference between the bias 20pb from the upper first bias magnetic layer 125a and the magnetic field bias 20ph from the hard bias layer 83. The relative angle between the initial magnetization 10mf (direction of the bias 10p) of the lower magnetic layer 10 (the first magnetization free layer) and the initial magnetization 20mf (direction of the bias 20p) of the upper magnetic layer 20 (the second magnetization free layer) is set to, for example, 90°.

In a case where the hard bias layer 83 is provided in the strain sensing element of the embodiment including the lower bias layer 110 and the upper bias layer 120 as described above, it is favorable to set the relative angle between the initial magnetization 10mf (direction of the bias 10p) of the lower magnetic layer 10 (the first magnetization free layer) and the initial magnetization 20mf (direction of the bias 20p) of the upper magnetic layer 20 (the second magnetization free layer) to 90° or more and 270° or less, and it is more favorable to set the relative angle to 135° or more and 225° or less. Here, as indicated by arrow A103 and arrow A104 illustrated in FIG. 30, in a case where the direction of strain applied to the strain sensing element of the embodiment is parallel to or perpendicular to the magnetization directions of the bias magnetic layers of both bias layers, it is possible to obtain an electrical resistance change that is monotonically increased or monotonically decreased in the range of 90° that is the dynamic magnetization range where the magnetization free layer is rotated due to the strain. Thus, this configuration is favorable.

Third Embodiment

Figure 31:
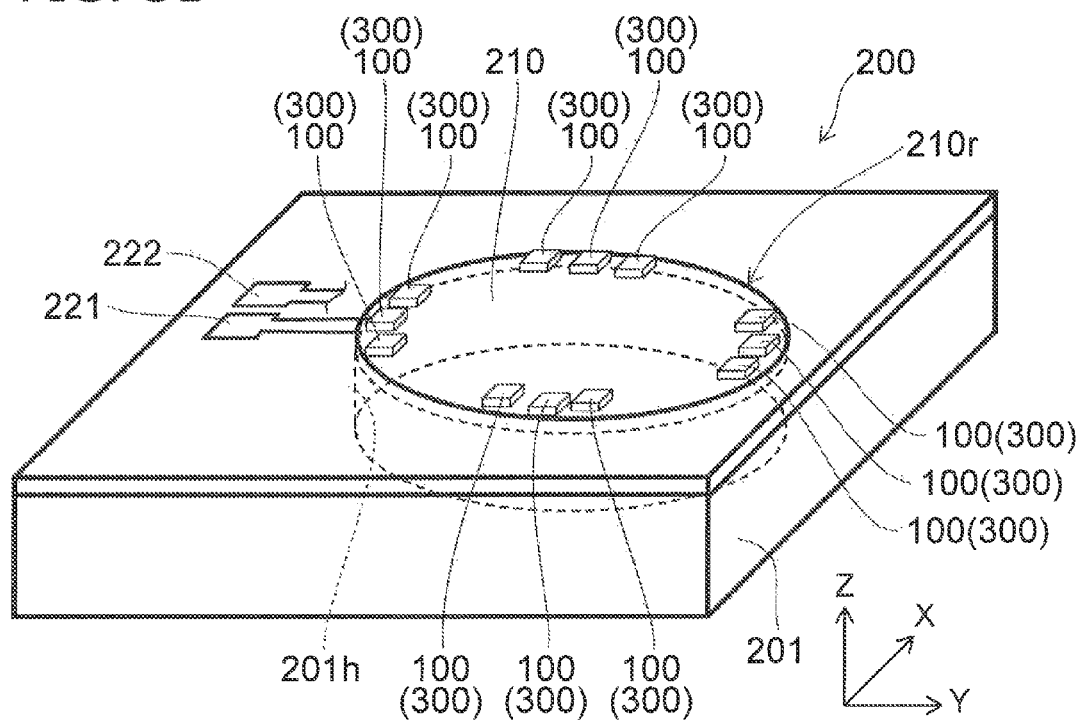
FIG. 31 is a schematic perspective view illustrating a pressure sensor according to a third embodiment.

FIG. 31 is a schematic perspective view illustrating a pressure sensor according to a third embodiment.

As illustrated in FIG. 31, a pressure sensor 200 according to the embodiment includes a support unit 201, a substrate 210, and a strain sensing element 100. The pressure sensor 200 according to the embodiment may include the strain sensing element 300 according to the second embodiment, instead of the strain sensing element 100 according to the first embodiment.

The substrate 210 is supported by the support unit 201. The substrate 210 has, for example, a flexible region. The substrate 210 is, for example, a diaphragm. The substrate 210 may be formed integrally with the support unit 201 or may be provided separately therefrom. The substrate 210 may include the same material as that of the support unit 201, or a material different from that of the support unit 201. A portion of the support unit 201 may be removed, so that the substrate 210 may be the thin portion of the support unit 201.

The thickness of the substrate 210 is thinner than the thickness of the support unit 201. In a case where the substrate 210 and the support unit 201 may include the same material, and in a case where the substrate 210 and the support unit 201 are integrally formed, the thin portion is used as the substrate 210, and the thick portion is used as the support unit 201.

The support unit 201 may have a through-hole 201h formed through the support unit 201 in the thickness direction, and the substrate 210 may be provided to cover the through-hole 201h. In such a case, for example, the film of the material used to form the substrate 210 may extend onto a portion of the support unit 201 other than the through-hole 201h. In such a case, the portion that overlaps the through-hole 201h, in the film of the material used as the substrate 210, is used to form the substrate 210.

The substrate 210 has an outer edge 210r. In a case where the substrate 210 and the support unit 201 include the same material and are integrally formed, the outer edge of the thin portion is used as the outer edge 210r of the substrate 210. In a case where the support unit 201 has the through-hole 201h formed through the support unit 201 in the thickness direction and the substrate 210 is provided to cover the through-hole 201h, the outer edge of the portion that overlaps the through-hole 201h, in the film of the material used as the substrate 210, is used as the outer edge 210r of the substrate 210.

The support unit 201 may continuously support the outer edge 210r of the substrate 210, or may support a part of the outer edge 210r of the substrate 210.

The strain sensing element 100 is provided on the substrate 210. For example, the strain sensing element 100 is provided on a part of the substrate 210. In the example, plural strain sensing elements 100 are provided on the substrate 210. The number of the strain sensing elements provided on the film part may be 1.

A first interconnect 221 and a second interconnect 222 are provided in the pressure sensor 200 illustrated in FIG. 31. The first interconnect 221 is connected to the strain sensing element 100. The second interconnect 222 is connected to the strain sensing element 100. For example, an inter-layer insulating film is provided between the first interconnect 221 and the second interconnect 222 to electrically insulate the first interconnect 221 from the second interconnect 222. A voltage is applied between the first interconnect 221 and the second interconnect 222, and thus, the voltage is applied to the strain sensing elements 100 through the first interconnect 221 and the second interconnect 222. If pressure is applied to the pressure sensor 200, the substrate 210 is deformed. In the strain sensing element 100, an electrical resistance R is changed as the substrate 210 is deformed. It is possible to sense the pressure by sensing the change of the electrical resistance R through the first interconnect 221 and the second interconnect 222.

The support unit 201 may include, for example, a plate-shaped substrate. A hollow part (through-hole 201h) is provided inside the substrate, for example.

The support unit 201 may include, for example, a semiconductor material such as silicon, a conductive material such as a metal, or an insulating material. The support unit 201 may include silicon oxide or silicon nitride, for example. The inside of the hollow part (through-hole 201h) is in a decompression state (vacuum state), for example. The inside of the hollow part (through-hole 201h) may be filled with gas such as air, or liquid. The inside of the hollow part (through-hole 201h) may be designed so that the substrate 210 can be bent. The inside of the hollow part (through-hole 201h) may be connected to the outside atmosphere.

The substrate 210 is provided above the hollow part (through-hole 201h). A portion of the support unit 201 may be thinly machined to be used as the substrate 210. The thickness of the substrate 210 (the length in the z-axis direction) is thinner than the thickness (the length in the z-axis direction) of the support unit 201.

If pressure is applied to the substrate 210, the substrate 210 is deformed. The pressure corresponds to pressure to be sensed by the pressure sensor 200. The applied pressure includes pressure due to sound waves, ultrasonic waves or the like. In a case where the pressure due to the sound waves, the ultrasonic waves or the like is sensed, the pressure sensor 200 functions as a microphone.

The substrate 210 includes, for example, an insulating material. The substrate 210 includes at least one selected from silicon oxide, silicon nitride and silicon oxynitride, for example. The substrate 210 may include, for example, a semiconductor material such as silicon. Further, the substrate 210 may include, for example, a metallic material.

The thickness of the substrate 210 is 0.1 μm or more and 3 μm or less, for example. It is favorable that the thickness be 0.2 μm or more and 1.5 μm or less. The substrate 210 may include a stacked body of a silicon oxide film having a thickness of 0.2 μm and a silicon film having a thickness of 0.4 μm.

FIGS. 32A to 32D are schematic plan views illustrating the relationship between the shape of the substrate and the direction of the bias layer of the first embodiment.

Figure 32A:
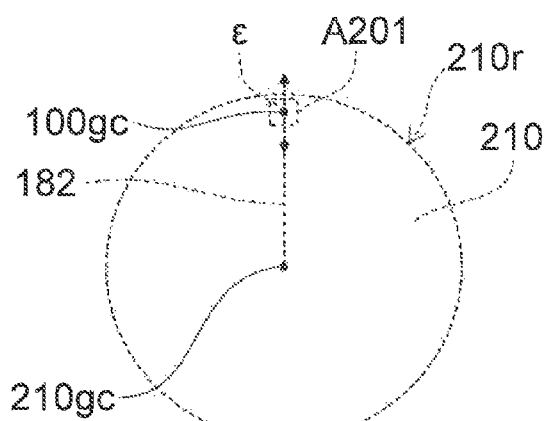
FIGS. 32A to 32D are schematic plan views illustrating the relationship between the shape of the substrate and the direction of the bias layer of the first embodiment.
Figure 32D:
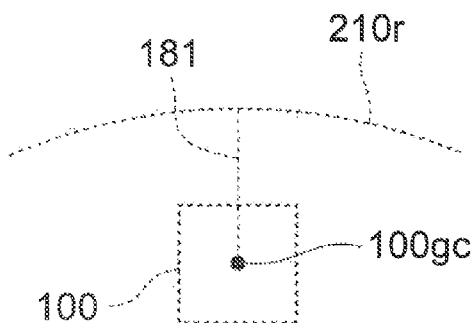
Figure 32B:
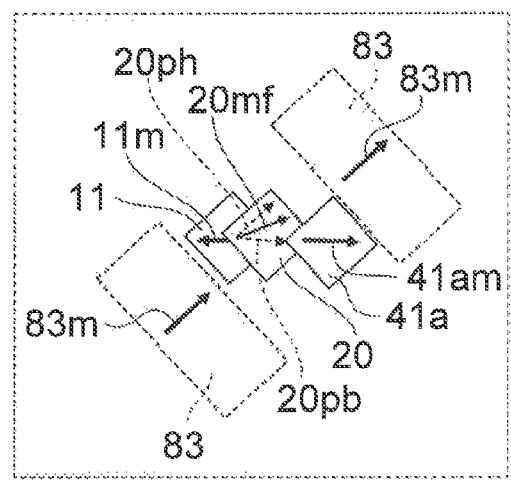
Figure 32C:
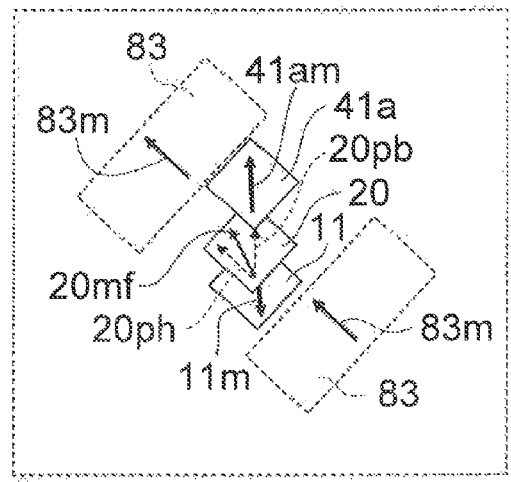

FIG. 32A is a perspective plan view illustrating the substrate 210. FIGS. 32B and 32C are schematic enlarged views illustrating a region A201 illustrated in FIG. 32A. FIG. 32D is a schematic enlarged view illustrating a portion where the strain sensing element 100 is provided.

In a case where the substrate 210 is a circular diaphragm, a strain ϵ is applied in a radial direction from its centroid. As illustrated in FIGS. 32A and 32B, for example, it is possible to set the magnetization 11m of the first magnetization pinned layer 11 and the magnetization 41am of the first bias magnetic layer 41a to be perpendicular to the direction of the strain ϵ. In other words, as illustrated in FIGS. 32B and 32D, for example, it is possible to set an angle formed by the magnetization urn of the first magnetization pinned layer 11 and the magnetization 41am of the first bias magnetic layer 41a, and a first straight line 181 that connects an outer edge 210r and a centroid 100gc of the strain sensing element 100 in the shortest distance to be perpendicular (90°). For example, if the angle is set to be 75° or more and 105° or less, it is possible to obtain the same characteristic as in the case of 90°. Alternatively, as illustrated in FIGS. 32A and 32B, for example, it is possible to set an angle formed by the magnetization 11m of the first magnetization pinned layer 11 and the magnetization 41am of the first bias magnetic layer 41a, and a second straight line 182 that connects a centroid 210gc of the substrate 210 and a centroid 100gc of the strain sensing element 100 in the shortest distance to be perpendicular (90°). For example, if the angle is set to be 75° or more and 105° or less, it is possible to obtain the same characteristic as in the case of 90°. It is possible to set the direction of the hard bias 83m to be shifted from the parallel direction and the perpendicular direction with respect to the direction of the strain ϵ. For example, it is possible to set the direction to be 45° or 135°. By performing the setting as described above, it is possible to shift the initial magnetization 20mf (direction of the bias 20p) of the second magnetic layer 20 (magnetization free layer) from the parallel direction and the perpendicular direction with respect to the direction of the strain ϵ, and to obtain the change of the electrical resistance R with respect to positive or negative pressure. It is favorable to adjust the initial magnetization 20mf (direction of the bias 20p) of the second magnetic layer 20 (magnetization free layer) by the bias 20pb from the first bias magnetic layer 41a and the magnetic field bias 20ph from the hard bias layer 83, and to set the initial magnetization 20mf (direction of the bias 20p) of the second magnetic layer 20 (magnetization free layer) to about 45° or about 135° with respect to the direction of the strain ϵ.

As illustrated in FIGS. 32A and 32C, for example, it is possible to set the magnetization 11m of the first magnetization pinned layer 11 and the magnetization 41am of the first bias magnetic layer 41a to be parallel to the direction of the strain ϵ. In other words, as illustrated in FIGS. 32C and 32D, for example, it is possible to set an angle formed by the magnetization 11m of the first magnetization pinned layer 11 and the magnetization 41am of the first bias magnetic layer 41a, and the first straight line 181 that connects the outer edge 210r and the centroid 100gc of the strain sensing element 100 in the shortest distance to be parallel (0°). For example, if the angle is set to be 0° or more and 15° or less, it is possible to obtain the same characteristic as in the case of 0°. Alternatively, as illustrated in FIGS. 32A and 32C, for example, it is possible to set an angle formed by the magnetization 11am of the first magnetization pinned layer 11 and the magnetization 41am of the first bias magnetic layer 41a, and the second straight line 182 that connects the centroid 210gc of the substrate 210 and the centroid 100gc of the strain sensing element 100 in the shortest distance to be parallel (0°). For example, if the angle is set to be 0° or more and 15° or less, it is possible to obtain the same characteristic as in the case of 0°. It is possible to set the direction of the hard bias 83m to be shifted from the parallel direction and the perpendicular direction with respect to the direction of the strain ε. For example, it is possible to set the direction to be 45° or 135°. By performing the setting as described above, it is possible to shift the initial magnetization 20mf (direction of the bias 20p) of the second magnetic layer 20 (magnetization free layer) from the parallel direction and the perpendicular direction with respect to the direction of the strain ε, and to obtain the change of the electrical resistance R with respect to positive or negative pressure. It is favorable to adjust the initial magnetization 20mf (direction of the bias 20p) of the second magnetic layer 20 (magnetization free layer) by the bias 20pb from the first bias magnetic layer 41a and the magnetic field bias 20ph from the hard bias layer 83, and to set the initial magnetization 20mf (direction of the bias 20p) of the second magnetic layer 20 (magnetization free layer) to about 45° or about 135° with respect to the direction of the strain ε.

In FIGS. 32A to 32D, an example is illustrated in which the substrate 210 is the circular diaphragm, but even in a diaphragm having a different shape, it may be considered that the strain ε occurs in a perpendicular direction to the outer edge 210r, and thus, it is possible to design the magnetization direction. In a case where the outer edge 210r is not a straight line but a curve, it is possible to consider that a direction perpendicular to the outer edge 210r is capable of being considered as a straight line in a minute range as a direction where the strain occurs.

FIGS. 33A to 33D are schematic plan views illustrating the relationship between the shape of the substrate and the direction of the bias layer of the second embodiment.

FIG. 33A is a perspective plan view illustrating the substrate 210. FIGS. 33B and 33C are schematic enlarged views illustrating a region A202 illustrated in FIG. 33A. FIG. 33D is a schematic enlarged view illustrating a portion where the strain sensing element 100 is provided.

In a case where the substrate 210 is a circular diaphragm, the strain ε is applied in the radial direction from the centroid. As illustrated in FIGS. 33A and 33B, for example, it is possible to set the magnetization 111am of the lower first bias magnetic layer 111a and the magnetization 121am of the upper first bias magnetic layer 121a to be perpendicular to the direction of the strain ε. In other words, as illustrated in FIGS. 33B and 33D, for example, it is possible to set an angle formed by the magnetization 111am of the lower first bias magnetic layer 111a and the magnetization 121am of the upper first bias magnetic layer 121a, and the first straight line 181 that connects the outer edge 210r and the centroid 100gc of the strain sensing element 100 in the shortest distance to be perpendicular (90°). For example, if the angle is set to be 75° or more and 105° or less, it is possible to obtain the same characteristic as in the case of 90°. Alternatively, as illustrated in FIGS. 33A and 33B, for example, it is possible to set an angle formed by the magnetization 111am of the lower first bias magnetic layer 111a and the magnetization 121am of the upper first bias magnetic layer 121a, and the second straight line 182 that connects the centroid 210gc of the substrate 210 and the centroid 100gc of the strain sensing element 100 in the shortest distance to be perpendicular (90°). For example, if the angle is set to be 75° or more and 105° or less, it is possible to obtain the same characteristic as in the case of 90°. It is possible to set the direction of the hard bias 83m to be parallel to the direction of the strain ε, for example. By performing the setting as described above, it is possible to shift the initial magnetization 10mf (direction of the bias 10p) of the lower magnetic layer 10 (the first magnetization free layer) and the initial magnetization 20mf (direction of the bias 20p) of the upper magnetic layer 20 (the second magnetization free layer) from the parallel direction and the perpendicular direction with respect to the direction of the strain ε, and to obtain the change of the electrical resistance R with respect to positive or negative pressure. It is favorable to adjust the initial magnetization 10mf (direction of the bias 10p) of the lower magnetic layer 10 (the first magnetization free layer) and the initial magnetization 20mf (direction of the bias 20p) of the upper magnetic layer 20 (the second magnetization free layer) by the bias 10pb from the lower first bias magnetic layer 111a, the bias 20pb from the upper first bias magnetic layer 121a, and the magnetic field biases 10ph and 20ph from the hard bias layer 83. Thus, it is possible to set a relative angle between the initial magnetization 10mf (direction of the bias 10p) of the lower magnetic layer 10 (the first magnetization free layer) and the initial magnetization 20mf (direction of the bias 20p) of the upper magnetic layer 20 (the second magnetization free layer) and the direction of the strain ε to be larger than, for example, 0° and smaller than 90°. For example, it is possible to set the relative angle to about 45°.

As illustrated in FIGS. 33A and 33C, for example, it is possible to set the magnetization 111am of the lower first bias magnetic layer 111a and the magnetization 121am of the upper first bias magnetic layer 121a to be parallel to the direction of the strain ε. In other words, as illustrated in FIGS. 33C and 33D, for example, it is possible to set an angle formed by the magnetization 111am of the lower first bias magnetic layer 111a and the magnetization 121am of the upper first bias magnetic layer 121a, and the first straight line 181 that connects the outer edge 210r and the centroid 100gc of the strain sensing element 100 in the shortest distance to be parallel (0°). For example, if the angle is set to be 0° or more and 15° or less, it is possible to obtain the same characteristic as in the case of 0°. Alternatively, as illustrated in FIGS. 33A and 33C, for example, it is possible to set an angle formed by the magnetization 111am of the lower first bias magnetic layer 111a and the magnetization 121am of the upper first bias magnetic layer 121a, and the second straight line 182 that connects the centroid 210gc of the substrate 210 and the centroid 100gc of the strain sensing element 100 in the shortest distance to be parallel (0°). For example, if the angle is set to be 0° or more and 15° or less, it is possible to obtain the same characteristic as in the case of 0°. It is possible to set the direction of the hard bias 83m to be perpendicular to the direction of the strain ε. By performing the setting as described above, it is possible to shift the initial magnetization 10mf (direction of the bias 10p) of the lower magnetic layer 10 (the first magnetization free layer) and the initial magnetization 20mf (direction of the bias 20p) of the upper magnetic layer 20 (the second magnetization free layer) from the parallel direction and the perpendicular direction with respect to the direction of the strain ε, and to obtain the change of the electrical resistance R with respect to positive or negative pressure. It is favorable to adjust the initial magnetization $10mf$ (direction of the bias $10p$) of the lower magnetic layer 10 (the first magnetization free layer) and the initial magnetization $20mf$ (direction of the bias $20p$) of the upper magnetic layer 20 (the second magnetization free layer) by the bias $10pb$ from the lower first bias magnetic layer 111*a*, the bias $20pb$ from the upper first bias magnetic layer 121*a*, and the magnetic field biases $10ph$ and $20ph$ from the hard bias layer 83. Thus, it is possible to set the relative angle between the initial magnetization $10mf$ (direction of the bias $10p$) of the lower magnetic layer 10 (the first magnetization free layer) and the initial magnetization $20mf$ (direction of the bias $20p$) of the upper magnetic layer 20 (the second magnetization free layer), and the direction of the strain $\epsilon$ to be larger than, for example, 0° and smaller than 90°. For example, it is possible to set the relative angle to about 45°.

In FIGS. 33A to 33D, an example is illustrated in which the substrate 210 is the circular diaphragm, but even in a diaphragm having a different shape, it may be considered that the strain $\epsilon$ occurs in a perpendicular direction to the outer edge 210*r*, and thus, it is possible to design the magnetization direction. In a case where the outer edge 210*r* is not a straight line but a curve, it is possible to consider that a direction perpendicular to the outer edge 210*r* capable of being considered as a straight line in a minute range as a direction where the strain occurs.

Figure 34A:
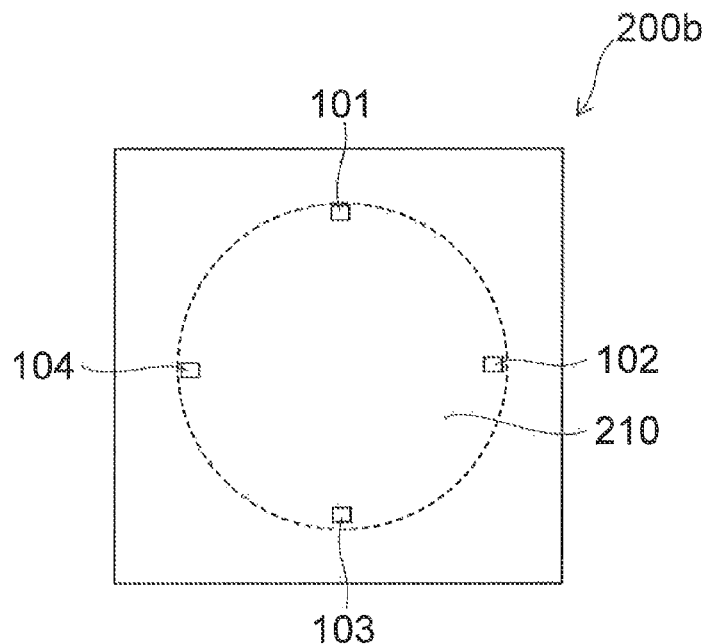
FIGS. 34A and 34B are schematic diagrams illustrating another pressure sensor according to the third embodiment.
Figure 34B:
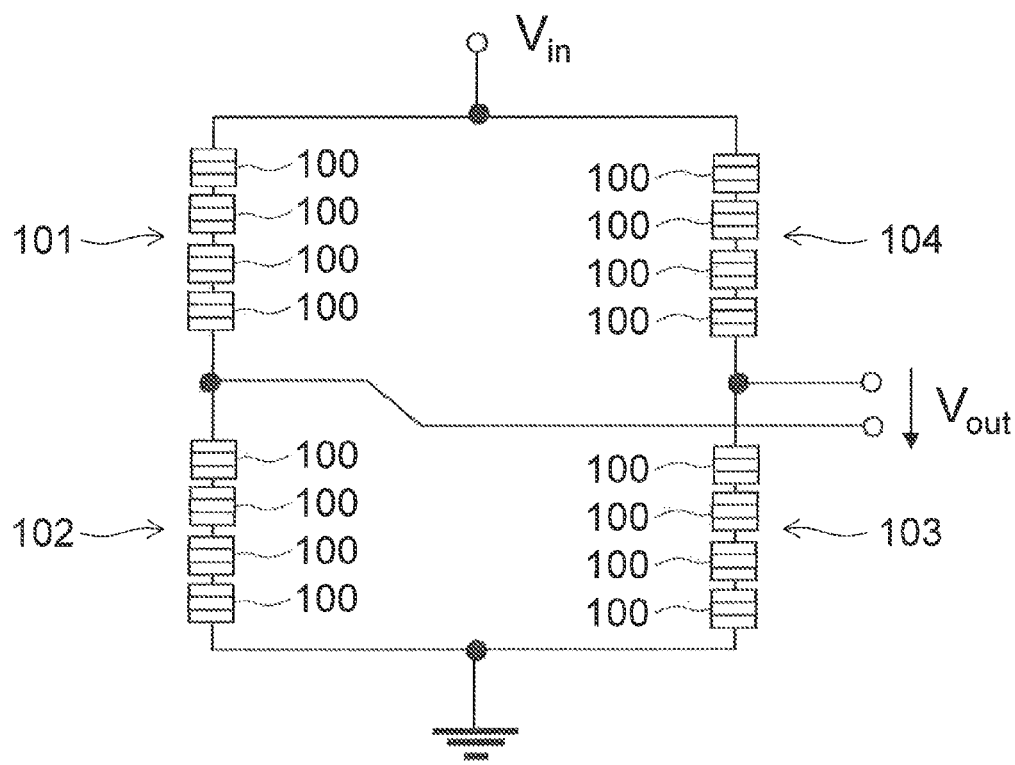

FIGS. 34A and 34B are schematic diagrams illustrating another pressure sensor according to the third embodiment.

As illustrated in FIGS. 34A and 34B, plural strain sensing elements 100 may be disposed on the substrate 210. That is, a pressure sensor 200*b* illustrated in FIGS. 34A and 34B includes a first strain sensing element unit 101, a second strain sensing element unit 102, a third strain sensing element unit 103, and a fourth strain sensing element unit 104. The first strain sensing element unit 101, the second strain sensing element unit 102, the third strain sensing element unit 103 and the fourth strain sensing element unit 104 include the plural strain sensing elements 100. In order to obtain the change of the same electrical resistance R with respect to the pressure in the plural strain sensing elements 100, the plural strain sensing elements 100 are connected in series or in parallel, thereby increasing the SN ratio, as described later.

In the examples of FIGS. 34A and 34B, the plural strain sensing elements 100 are disposed, but one strain sensing element 100 may be disposed. In the examples of FIGS. 34A and 34B, a variation of disposition on the substrate 210 of a circular shape is illustrated.

The strain sensing element 100 is only required to have a very small size.

Thus, it is possible to sufficiently decrease the area of the strain sensing element 100 compared with the area of the substrate 210 that is deformed due to pressure. For example, it is possible to set the area of the strain sensing element 100 to ⅕ or less of the area of the substrate 210.

For example, in a case where the diameter size of the substrate 210 is about 60 μm, it is possible to set the size of the strain sensing element 100 to 12 μm or less. In a case where the diameter size of the substrate 210 is about 600 μm, it is possible to set the size of the strain sensing element 100 to 120 μm or less.

In such a case, it is not necessary to excessively decrease the sizes of the strain sensing elements 100, respectively, in consideration of machining accuracy or the like of the strain sensing element 100. Thus, it is possible to set the size of the strain sensing element 100 to 0.05 μm or more and 30 μm or less, for example.

In the example of FIG. 34A, the planar shape of the substrate 210 is circular, but the planar shape of the substrate 210 is not limited to the circle. The planar shape of the substrate 210 may be an ellipse, a rectangular polygon such as a square or a rectangle, or the like, for example.

The plural strain sensing elements 100 provided on the substrate 210 may be connected in series. When setting the number of the strain sensing elements 100 in which the plural strain sensing elements 100 are connected in series as N, an electrical signal that is obtained is N times that of a case where the number of the strain sensing elements 100 is 1. On the other hand, the thermal noise and the Schottky noise increase by a factor of $N^{1/2}$. In other words, the SN ratio (signal-noise ratio (SNR)) increases by a factor of $N^{1/2}$. By increasing the number N of the strain sensing elements 100 connected in series, it is possible to enhance the SN ratio without increasing the size of the substrate 210.

The bias voltage applied to one strain sensing element 100 is, for example, 50 millivolts (mv) or more and 150 mV or less. In a case where N strain sensing elements 100 are connected in series, the bias voltage is 50 mV×N or more and 150 mV×N or less. For example, in a case where the number N of the strain sensing elements 100 connected in series is 25, the bias voltage is 1.25 V or more and 3.75 V or less.

If the value of the bias voltage is 1 V or more, the design of the electronic circuit that processes the electrical signal obtained from the strain sensing elements 100 becomes simple and is favorable from a practical point of view.

In the electronic circuit that processes the electrical signals obtained from the strain sensing elements 100, it is not favorable that the bias voltage (the voltage between terminals) exceed 10 V. In the embodiment, the number N of the strain sensing elements 100 connected in series and the bias voltage are set so that an appropriate voltage range is set.

For example, in a case where the plural strain sensing elements 100 are electrically connected in series, it is favorable that the voltage be 1 V or more and 10 V or less. For example, the voltage that is applied between the terminals of the plural strain sensing elements 100 that are electrically connected in series (between the terminal of one end and the terminal of the other end) is 1 V or more and 10 V or less.

To generate the voltage, it is favorable that the number N of the strain sensing elements 100 connected in series be 20 mV or more and 200 mV or less in a case where the bias voltage applied to one strain sensing element 100 is 50 mV. In a case where the bias voltage applied to the one strain sensing element 100 is 150 mV, it is favorable that the number N of the strain sensing elements 100 connected in series be 6 or more and 200 or less, and it is preferable that the number N of the strain sensing elements 100 connected in series be 7 or more and 66 or less.

At least a portion of the plural strain sensing elements 100 may be electrically connected in parallel.

As shown in FIG. 34B, the plural strain sensing elements 100 may be connected such that the plural strain sensing elements 100 form a Wheatstone bridge circuit. Thus, for example, it is possible to perform temperature compensation for the detection characteristics.

Figure 35A:
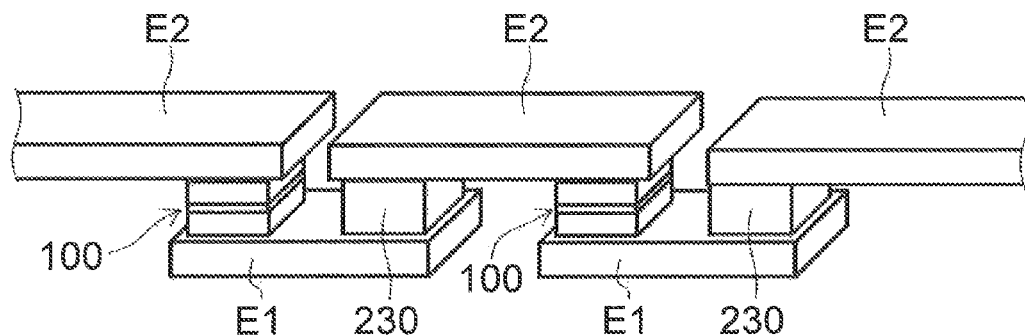
FIGS. 35A to 35C are schematic perspective views illustrating pressure sensors according to the third embodiment.
Figure 35B:
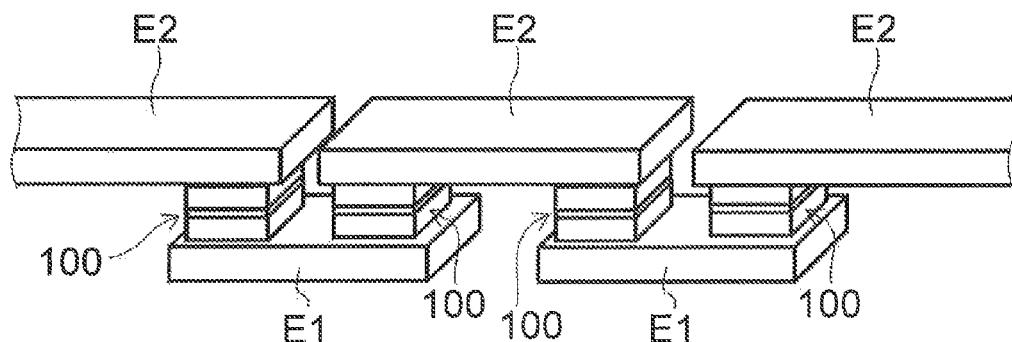
Figure 35C:
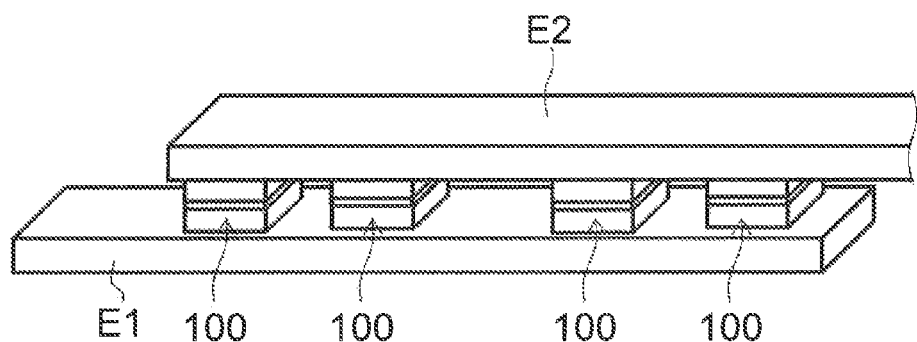

FIGS. 35A to 35C are schematic perspective views illustrating pressure sensors according to the third embodiment.

FIGS. 35A to 35C illustrate examples of connections of the plural strain sensing elements 100.

As illustrated in FIG. 35A, in a case where the plural strain sensing elements 100 are electrically connected in series, the strain sensing elements 100 and via contacts 230 are provided between the first electrode E1 (for example, the second interconnect 222) and the second electrode E2 (for example, the first interconnect 221). Thus, the conduction direction is in one direction. The current conducted through the plural strain sensing elements 100 is downward or upward. In this connection, the signal-noise characteristics of the plural strain sensing elements 100 may be similar to each other. As shown in FIG. 35B, the strain sensing elements 100 are disposed between the first electrode E1 and the second electrode E2 without the via contacts 230 being provided. In the example, the direction of the current conducted through the strain sensing element 100 is reversed between two adjacent strain sensing elements 100. In this connection, the density of the disposition of the plural strain sensing elements 100 is high.

As shown in FIG. 35C, the plural strain sensing elements 100 are provided between one first electrode E1 and one second electrode E2. The plural strain sensing elements 100 are connected in parallel.

Hereinafter, an example of a method for manufacturing a pressure sensor according to the embodiment will be described. An example of a method for manufacturing the pressure sensor is described below.

FIGS. 36A to 36E are schematic cross-sectional views sequentially illustrating processes of the method for manufacturing the pressure sensor according to the embodiment.

Figure 36A:
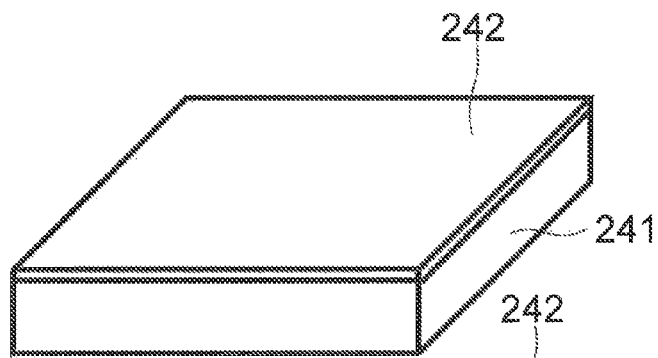
FIGS. 36A to 36E are schematic cross-sectional views sequentially illustrating processes of the method for manufacturing the pressure sensor according to the embodiment.

As shown in FIG. 36A, a thin film 242 is formed on a substrate 241 (for example, Si substrate). The substrate 241 is used to form the support unit 201. The thin film 242 is used to form the substrate 210.

For example, the thin film 242 of $SiO_x/Si$ is formed on the Si substrate by sputtering. A metal layer such as an $SiO_x$ single layer, an SiN single layer or Al may be used as the thin film 242. Further, a flexible plastic material such as polyimide or paraxylene-based polymer may be used as the thin film 242. SOI (Silicon On Insulator) substrates may be used as the substrate 241 and the thin film 242. In the SOI, for example, a stacked film of $SiO_2/Si$ is formed on the Si substrate by bonding the substrates.

Figure 36B:
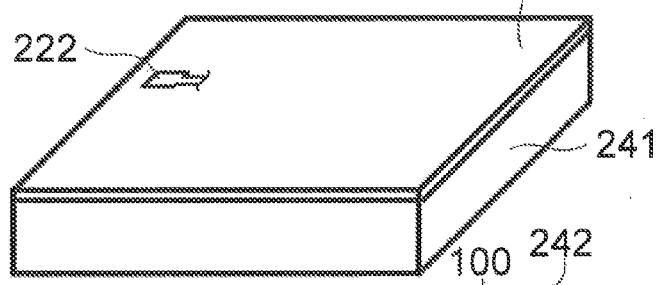

As illustrated in FIG. 36B, the second interconnect 222 is formed. In this process, a conductive film that is used to form the second interconnect 222 is formed, and the conductive film is patterned by photolithography and etching. In a case where an insulating film is filled around the second interconnect 222, lift-off process may be applied. In the lift-off process, for example, the insulating film is formed on the entire surface after etching the pattern of the second interconnect 222 and prior to peeling the resist, and then, the resist is removed.

Figure 36C:
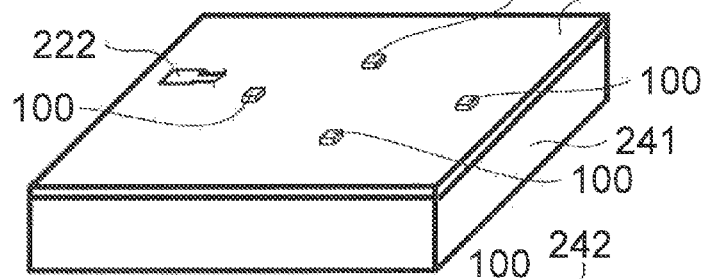

As illustrated in FIG. 36C, the strain sensing element 100 is formed. In the process, a stacked body that is used to form the strain sensing element 100 is formed, and then, the stacked body is patterned by photolithography and etching. In a case where the side wall of the stacked body of the strain sensing element 100 is embedded in the insulating layer 81, lift-off process may be applied. In the lift-off process, for example, the insulating layer 81 is formed on the entire surface after patterning the stacked body and prior to peeling the resist, and then, the resist is removed.

Figure 36D:
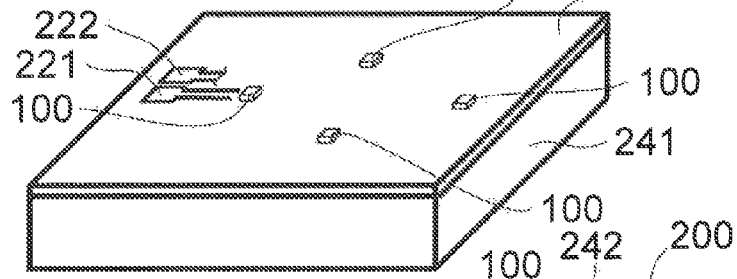

As illustrated in FIG. 36D, the first interconnect 221 is formed. In the process, a conductive film that is used to form the first interconnect 221 is formed, and then, the conductive film is patterned by photolithography and etching. In a case where an insulating film is filled around the first interconnect 221, lift-off process may be applied. In the lift-off process, the insulating film is formed on the entire surface after patterning the first interconnect 221 and prior to peeling the resist, and then, the resist is removed.

Figure 36E:
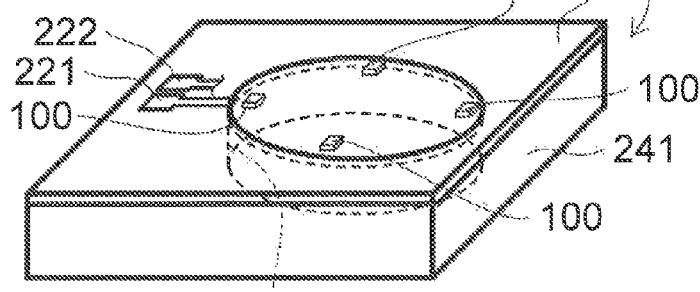

As illustrated in FIG. 36E, the hollow portion 201a is formed by performing etching from the back surface of the substrate 241.

Thus, the substrate 210 and the support unit 201 are formed. For example, in a case where the stacked film of $SiO_x/Si$ is used as the thin film 242 used to form the substrate 210, a deep digging process of the substrate 241 is performed from the back surface (the lower surface) of the thin film 242 toward the front surface (the upper surface) thereof. Thus, the hollow portion 201a is formed. For example, a double-sided aligner exposure apparatus may be used to form the hollow portion 201a. Thus, it is possible to form the hole pattern of the resist on the back surface to match the position of the strain sensing element 100 on the front surface.

A Bosch process using, for example, RIE may be used to etch the Si substrate. In the Bosch process, for example, an etching process using $SF_6$ gas and a deposition process using $C_4F_8$ gas are repeated. Thus, selective etching of the substrate 241 in the depth direction (the Z-axis direction) is performed while suppressing the etching of the side wall of the substrate 241. For example, an $SiO_x$ layer is used as an end point of the etching. In other words, the etching is stopped using the $SiO_x$ layer having an etching selection ratio different from that of Si. The $SiO_x$ layer that functions as the etching stopper layer may be used as a portion of the substrate 210. After the etching, the $SiO_x$ layer may be removed, for example, by processing of anhydrous hydrogen fluoride, alcohol, or the like.

In this manner, the pressure sensor 200 according to the embodiment is formed. The other pressure sensors according to the embodiments may also be manufactured by similar methods.

Fourth Embodiment

Figure 37A:
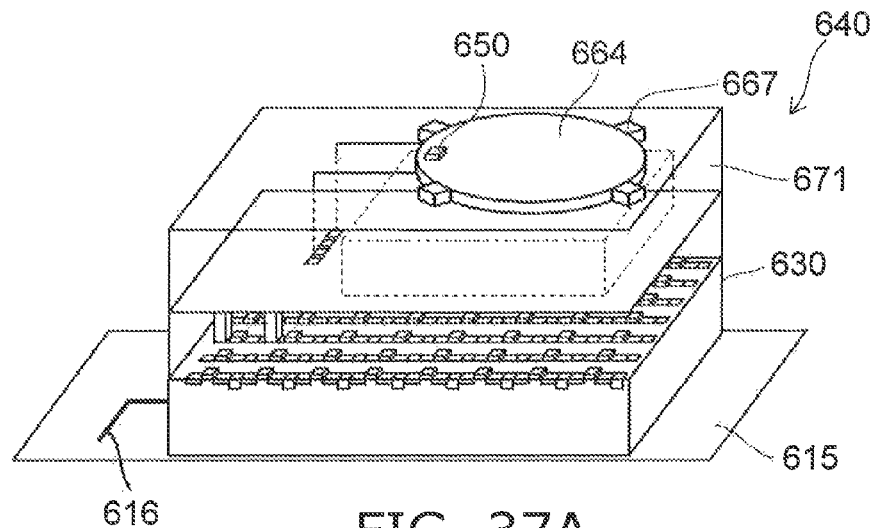
FIGS. 37A to 37C are schematic diagrams illustrating a pressure sensor according to a fourth embodiment.
Figure 37B:
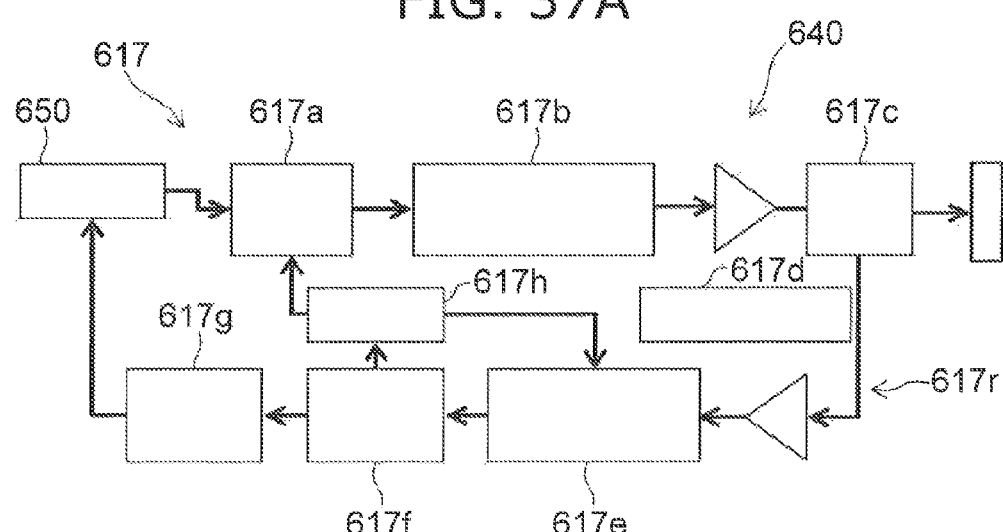
Figure 37C:
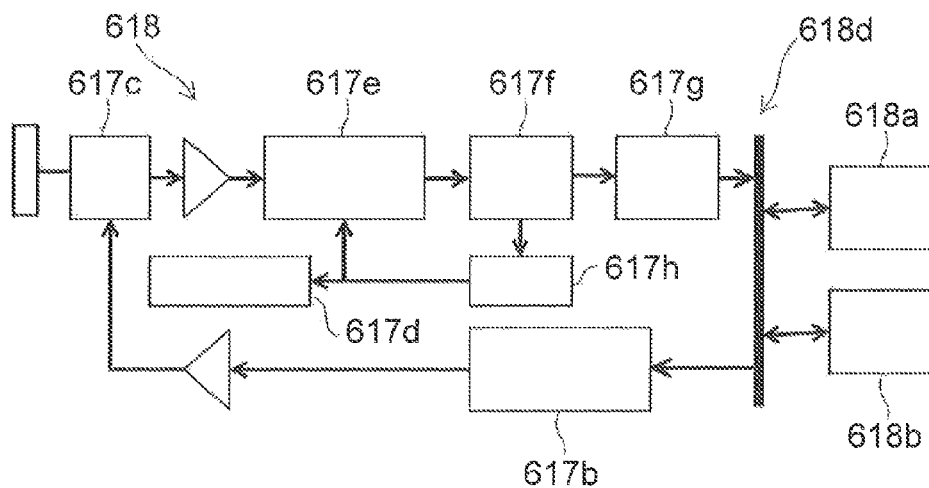

FIGS. 37A to 37C are schematic diagrams illustrating a pressure sensor according to a fourth embodiment. FIG. 37A is a schematic perspective view, and FIGS. 37B and 37C are block diagrams illustrating a pressure sensor 640.

As shown in FIGS. 37A and 37B, a base unit 671, a sensing unit 650, a semiconductor circuit unit 630, an antenna 615, an electrical interconnect 616, a transmitting circuit 617, and a receiving circuit 617r are provided in the pressure sensor 640.

The antenna 615 is electrically connected to the semiconductor circuit unit 630 via the electrical interconnect 616.

The transmitting circuit 617 performs a wireless transmission of data based on an electrical signal flowing in the sensing unit 650. At least a portion of the transmitting circuit 617 may be provided in the semiconductor circuit unit 630.

The receiving circuit 617r receives a control signal from an electronic device 618d. At least a portion of the receiving circuit 617r may be provided in the semiconductor circuit unit 430. By providing the receiving circuit 617r, it is possible to control the operation of the pressure sensor 640 by operating the electronic device 618d, for example.

As illustrated in FIG. 37B, for example, an AD converter 617a that is connected to the sensing unit 650 and a Manchester encoding unit 617b may be provided in the transmitting circuit 617. Further, a switching unit 617c may be provided to perform switching between transmitting and receiving. In such a case, a timing controller 617d may be provided, and the switching of the switching unit 617c may be controlled by the timing controller 617d. A data correcting unit 617e, a synchronizing unit 617f, a determining unit 617g, and a voltage controlled oscillator 617h (VCO) may be further provided.

As illustrated in FIG. 37C, a receiving unit 618 is provided in the electronic device 618d used in combination with the pressure sensor 640. An electronic device such as a portable terminal may be used as the electronic device 618d.

In such a case, the electronic device 618d that includes the receiving unit 618 may be used in combination with the pressure sensor 640 that includes the transmitting circuit 617.

The Manchester encoding unit 617b, the switching unit 617c, the timing controller 617d, the data correcting unit 617e, the synchronizing unit 617f, the determining unit 617g, the voltage controlled oscillator 617h, a memory unit 618a, and a central processing unit (CPU) 618b may be provided in the electronic device 618d.

In this example, the pressure sensor 640 further includes a pinning unit 667. The pinning unit 667 fixes a film part 664 to the base unit 671. The thickness dimension of the pinning unit 667 may be thicker than that of the film part 664 so that the pinning unit 667 is not deflected even when the external pressure is applied.

For example, the pinning unit 667 may be provided at uniform intervals at the circumferential edge of the film part 664.

Further, the pinning unit 667 may be provided to continuously surround the entire periphery of the film part 664.

The pinning unit 667 may be formed of, for example, the same material as that of the base unit 671. In such a case, the pinning unit 667 may be formed of, for example, silicon or the like.

The pinning unit 667 may also be formed of, for example, the same material as that of the film part 664.

An example of a method for manufacturing the pressure sensor according to the embodiment will be described.

FIG. 38A, FIG. 38B, FIG. 39A, FIG. 39B, FIG. 40A, FIG. 40B, FIG. 41A, FIG. 41B, FIG. 42A, FIG. 42B, FIG. 43A, FIG. 43B, FIG. 44A, FIG. 44B, FIG. 45A, FIG. 45B, FIG. 46A, FIG. 46B, FIG. 47A, FIG. 47B, FIG. 48A, FIG. 48B, FIG. 49A and FIG. 49B are schematic diagrams illustrating the method for manufacturing the pressure sensor according to the embodiment.

Figure 38A:
FIGS. 38A and 38B are schematic diagrams illustrating the method for manufacturing the pressure sensor according to the embodiment.
Figure 38B:
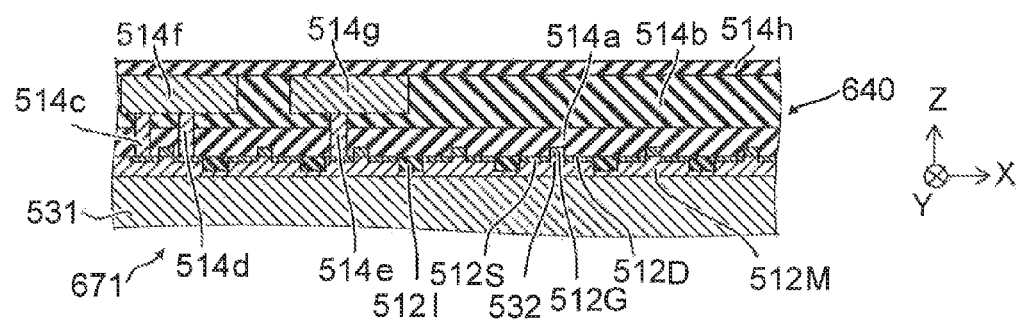
Figure 39A:
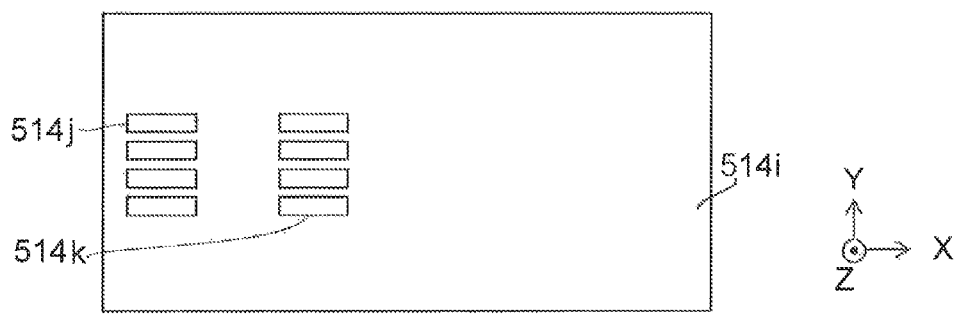
FIGS. 39A and 39B are schematic diagrams illustrating the method for manufacturing the pressure sensor according to the embodiment.
Figure 39B:
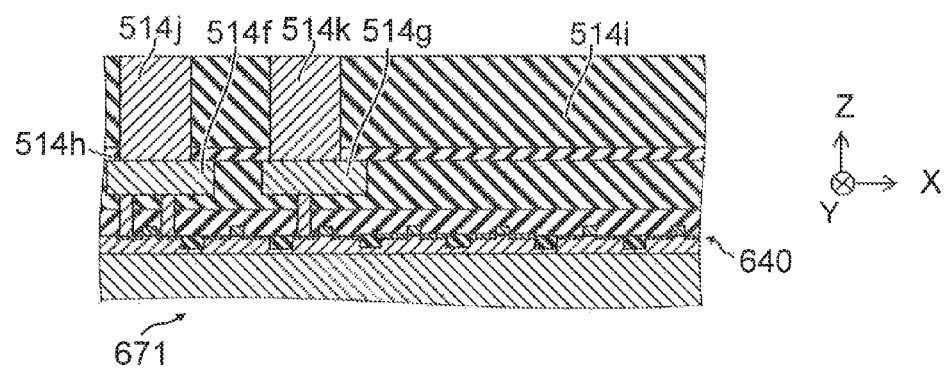

FIG. 38A, FIG. 39A, . . . , and FIG. 49A are schematic plan views, and FIG. 38B, FIG. 39B, . . . , and FIG. 49B are schematic cross-sectional views.

As illustrated in FIGS. 38A and 38B, a semiconductor layer 512M is formed at the front surface portion of a semiconductor substrate 531. Subsequently, an element-isolation insulating layer 512I is formed on the upper surface of the semiconductor layer 512M. Then, a gate 512G is formed on the semiconductor layer 512M with an insulating layer (not shown) interposed therebetween. Subsequently, a transistor 532 is formed by forming a source 512S and a drain 512D on both sides of the gate 512G. Then, an inter-layer insulating film 514a is formed on the transistor 532, and an inter-layer insulating film 514b is formed on the inter-layer insulating film 514a.

Subsequently, trenches and holes are formed in a portion of the inter-layer insulating films 514a and 514b in a region where a non-hollow portion is to be formed. Then, connecting pillars 514c to 514e are formed by filling a conductive material into the holes. In such a case, for example, the connecting pillar 514c is electrically connected to the source 512S of one transistor 532, and the connecting pillar 514d is electrically connected to the drain 512D of the one transistor 532. For example, the connecting pillar 514e is electrically connected to the source 512S of another transistor 532. Then, interconnect units 514f and 514g are formed by filling a conductive material into the trenches. The interconnect unit 514f is electrically connected to the connecting pillar 514c and the connecting pillar 514d. The interconnect unit 514g is electrically connected to the connecting pillar 514e. Then, an inter-layer insulating film 514h is formed on the inter-layer insulating film 514b.

As illustrated in FIGS. 39A and 39B, an inter-layer insulating film 514i made of silicon oxide ($SiO_2$) is formed on the inter-layer insulating film 514h by, for example, chemical vapor deposition (CVD). Then, holes are formed at predetermined positions of the inter-layer insulating film 514i, and a conductive material (for example, a metallic material) is filled into the holes. Then, the upper surface is planarized by chemical mechanical polishing (CMP). Thus, a connecting pillar 514j that is connected to the interconnect unit 514f and a connecting pillar 514k that is connected to the interconnect unit 514g are formed.

Figure 40A:
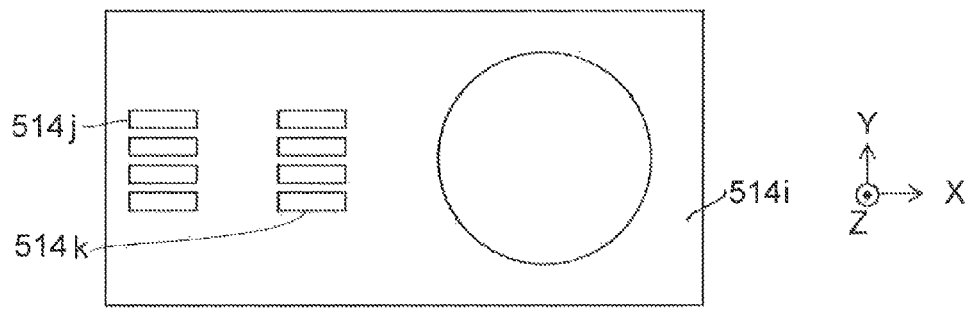
FIGS. 40A and 40B are schematic diagrams illustrating the method for manufacturing the pressure sensor according to the embodiment.
Figure 40B:
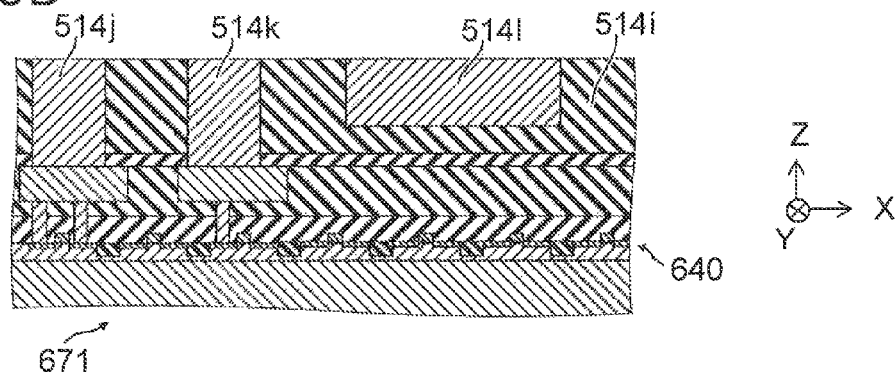

As illustrated in FIGS. 40A and 40B, a recess is formed in a region of the inter-layer insulating film 514i where a hollow portion 570 is to be formed, and a sacrificial layer 514l is filled into the recess. The sacrificial layer 514l may be formed of, for example, a material that can form a film at a low temperature. The material that can form the film at the low temperature is, for example, silicon-germanium (SiGe), or the like.

Figure 41A:
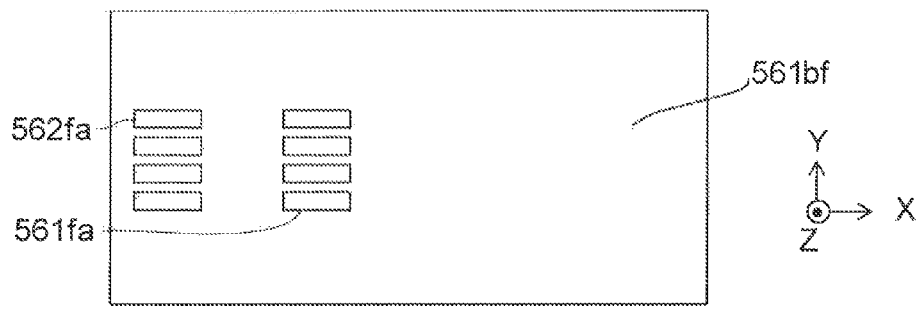
FIGS. 41A and 41B are schematic diagrams illustrating the method for manufacturing the pressure sensor according to the embodiment.
Figure 41B:
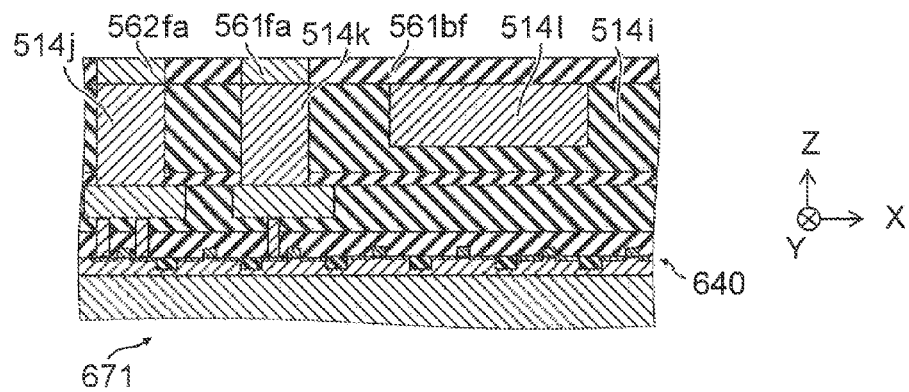

As illustrated in FIGS. 41A and 41B, an insulating film 561bf that is used to form a film part 564 is formed on the inter-layer insulating film 514i and the sacrificial layer 514l. The insulating film 561bf may be formed of, for example, silicon oxide ($SiO_2$), or the like. A connecting pillar 561fa and a connecting pillar 562fa are formed by providing plural holes in the insulating film 561bf and by filling a conductive material (for example, a metal material) into the plural holes. The connecting pillar 561fa is electrically connected to the connecting pillar 514k, and the connecting pillar 562fa is electrically connected to the connecting pillar 514j.

As illustrated in FIGS. 42A and 42B, a conductive layer 561f that is used to form an interconnect 557 is formed on the insulating film 561bf, the connecting pillar 561fa and the connecting pillar 562fa.

As illustrated in FIGS. 43A and 43B, a stacked film 550f is formed on the conductive layer 561f.

Figure 44A:
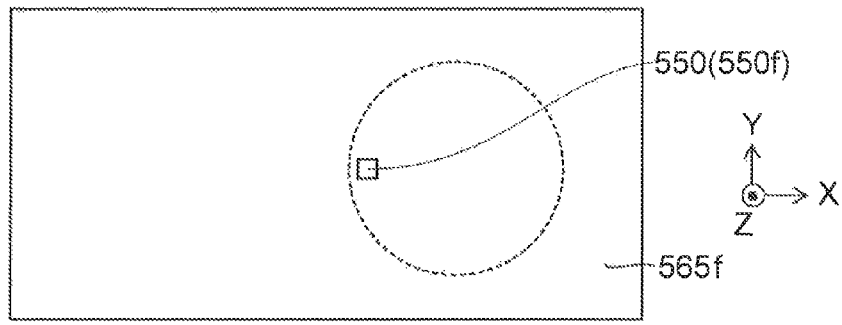
FIGS. 44A and 44B are schematic diagrams illustrating the method for manufacturing the pressure sensor according to the embodiment.
Figure 44B:
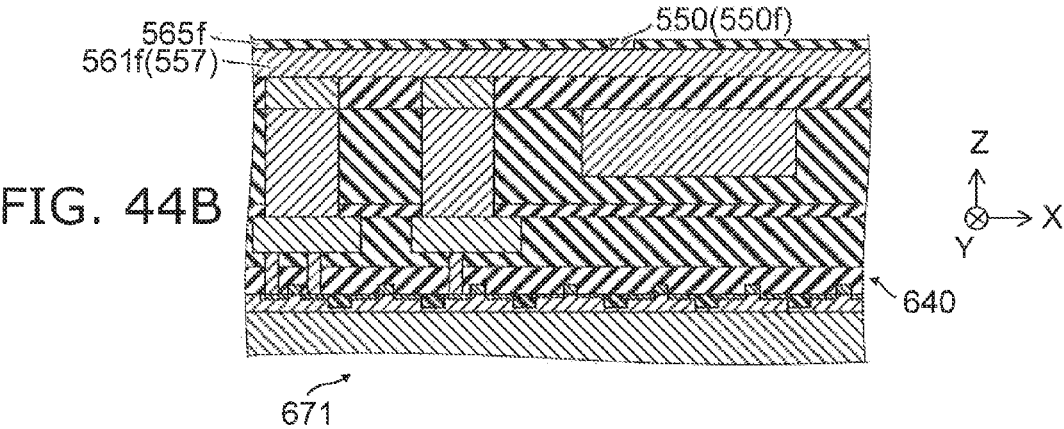

As illustrated in FIGS. 44A and 44B, the stacked film 550f is patterned into a predetermined shape, and an insulating film 565f that is used to form an insulating layer 565 is formed on the stacked film 550f. The insulating film 565f may be formed by, for example, silicon oxide ($SiO_2$), or the like.

Figure 45A:
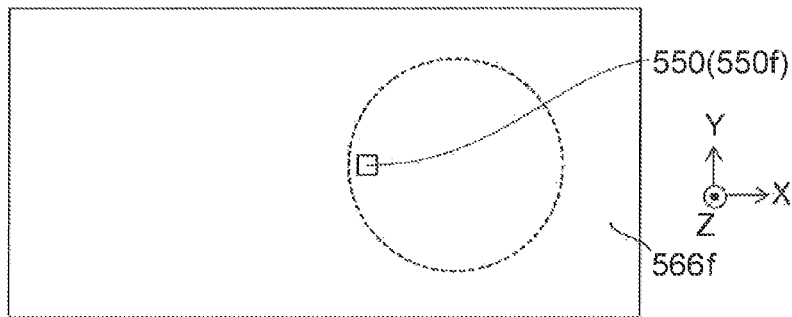
FIGS. 45A and 45B are schematic diagrams illustrating the method for manufacturing the pressure sensor according to the embodiment.
Figure 45B:
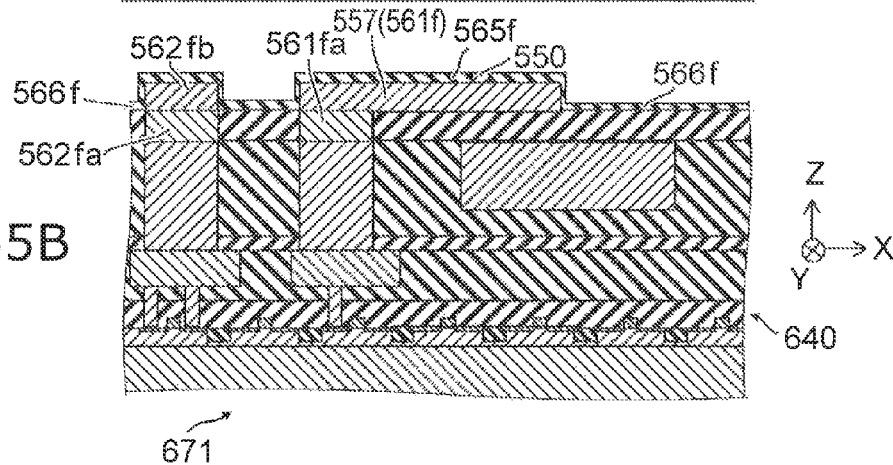

Then, as illustrated in FIG. 45A and FIG. 45B, a portion of the insulating film 565f is removed, and the conductive layer 561f is patterned into a predetermined shape. Thus, the interconnect 557 is formed. At this time, a portion of the conductive layer 561f becomes a connecting pillar 562fb that is electrically connected to the connecting pillar 562fa. Further, an insulating film 566f that is used to form an insulating layer 566 is formed thereon.

Figure 46A:
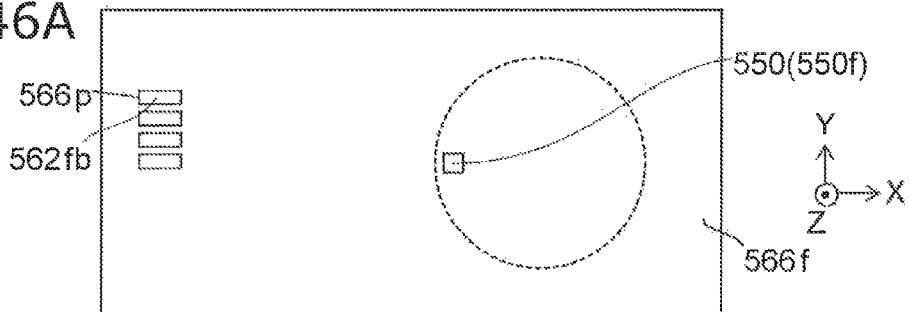
FIGS. 46A and 46B are schematic diagrams illustrating the method for manufacturing the pressure sensor according to the embodiment.
Figure 46B:
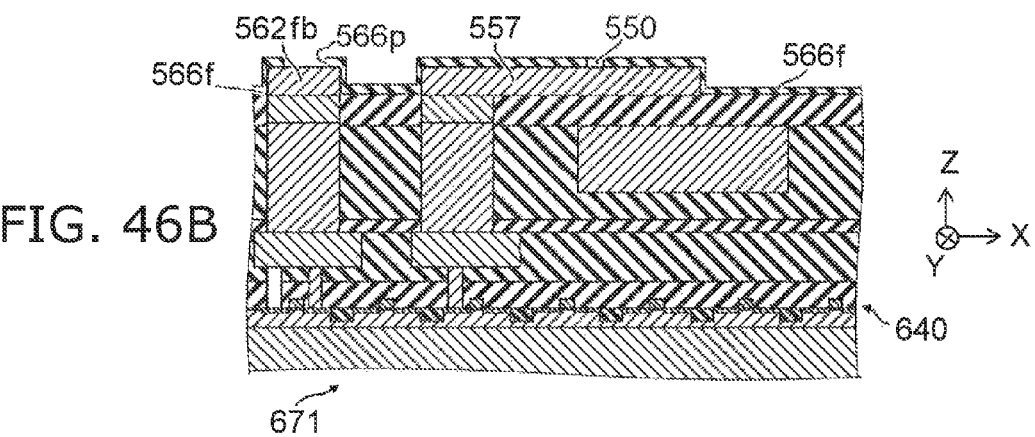

As illustrated in FIGS. 46A and 46B, an opening 566p is formed in the insulating film 566f. Thus, the connecting pillar 562fb is exposed.

Figure 47A:
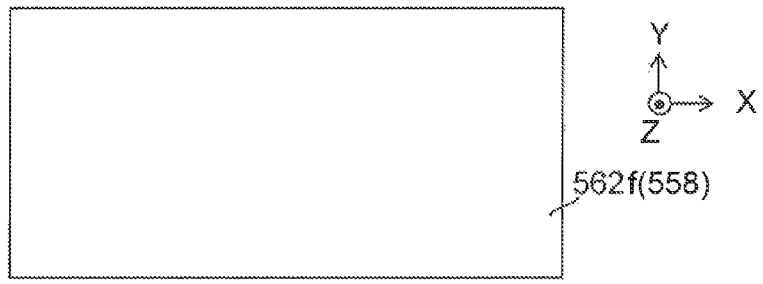
FIGS. 47A and 47B are schematic diagrams illustrating the method for manufacturing the pressure sensor according to the embodiment.
Figure 47B:
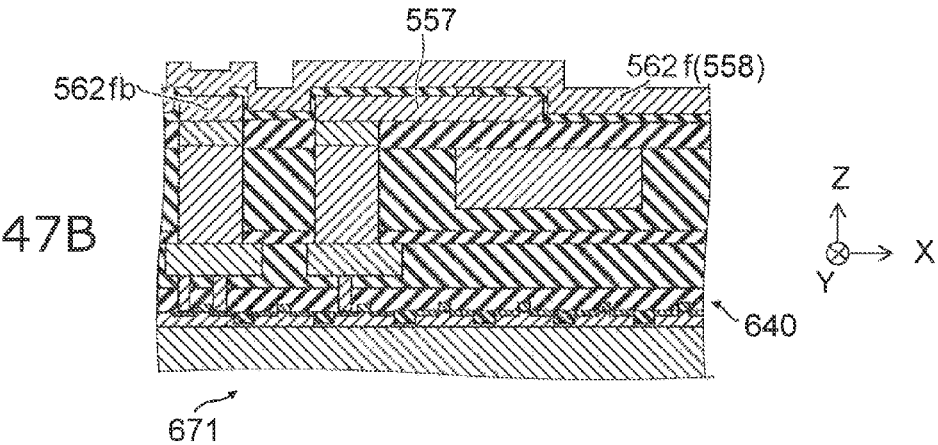

As illustrated in FIGS. 47A and 47B, a conductive layer 562f that is used to form an interconnect 558 is formed on the upper surface. A portion of the conductive layer 562f is electrically connected to the connecting pillar 562fb. As illustrated in FIGS. 48A and 48B, the conductive layer 562f is patterned into a predetermined shape. Thus, the interconnect 558 is formed. The interconnect 558 is electrically connected to the connecting pillar 562fb.

As illustrated in FIGS. 49A and 49B, an opening 566o having a predetermined shape is formed in the insulating film 566f. The insulating film 561bf is patterned via the opening 566o, and the sacrificial layer 514l is removed via the opening 566o. Thus, the hollow portion 570 is formed. The removal of the sacrificial layer 514l may be performed by, for example, wet etching.

To form a pinning unit 567 to have a ring shape, for example, a space between the edge of the non-hollow portion above the hollow portion 570 and the film part 564 may be filled with an insulating film.

Thus, the pressure sensor is formed.

Fifth Embodiment

Figure 50:
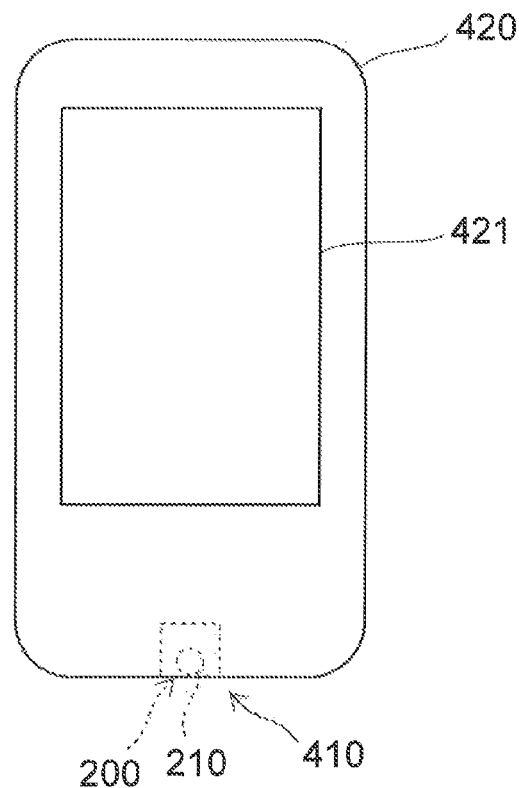
FIG. 50 is a schematic plan view illustrating a microphone according to the fourth embodiment.

FIG. 50 is a schematic plan view illustrating a microphone according to the fourth embodiment.

As illustrated in FIG. 50, a microphone 410 includes any pressure sensor (for example, the pressure sensor 200) according to the embodiments described above or a pressure sensor according to a modification of these pressure sensors. Hereinafter, the microphone 410 that includes the pressure sensor 200 will be described as an example.

The microphone 410 is embedded in an end portion of a personal digital assistant 420. The substrate 210 of the pressure sensor 200 that is provided in the microphone 410 may be substantially parallel to, for example, a surface of the personal digital assistant 420 where a display unit 421 is provided. The disposition of the substrate 210 is not limited to the above illustration and may be appropriately modified.

Since the microphone 410 includes the pressure sensor 200 or the like, it is possible to achieve high sensitivity with respect to frequencies in a wide band.

Further, a case where the microphone 410 is embedded in the personal digital assistant 420 is illustrated, but this is not limiting. The microphone 410 may also be embedded in, for example, an IC recorder, a pin microphone, or the like.

Sixth Embodiment

The embodiment relates to an acoustic microphone using the pressure sensor of the embodiments described above.

Figure 51:
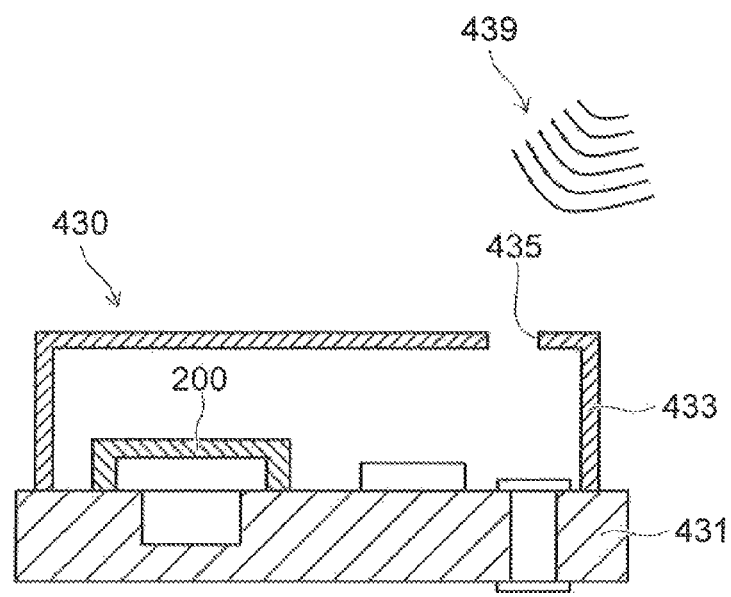
FIG. 51 is a schematic cross-sectional view illustrating an acoustic microphone according to the fifth embodiment.

FIG. 51 is a schematic cross-sectional view illustrating an acoustic microphone according to the fifth embodiment.

An acoustic microphone 430 according to the embodiment includes a printed circuit board 431, a cover 433, and the pressure sensor 200. The printed circuit board 431 includes, for example, a circuit such as an amplifier. An acoustic hole 435 is provided in the cover 433. Sound 439 passes through the acoustic hole 435 to enter the inside of the cover 433.

Any of the pressure sensors described in regard to the embodiments described above or a pressure sensor according to a modification of these pressure sensors may be used as the pressure sensor 200.

The acoustic microphone 430 responds to sound pressure. The acoustic microphone 430 of high sensitivity is obtained by using the pressure sensor 200 of high sensitivity. For example, the pressure sensor 200 is mounted on the printed circuit board 431, and then, electrical signal lines are provided. The cover 433 is provided on the printed circuit board 431 to cover the pressure sensor 200.

According to the embodiment, it is possible to provide an acoustic microphone of high sensitivity.

Seventh Embodiment

The embodiment relates to a blood pressure sensor using the pressure sensor of the embodiments described above.

FIGS. 52A and 52B are schematic views illustrating a blood pressure sensor according to the sixth embodiment.

FIG. 52A is a schematic plan view illustrating the skin over the arterial vessel of a human. FIG. 52B is a cross-sectional view taken along line LIIB-LIIB of FIG. 52A.

In the embodiment, the pressure sensor 200 is applied as a blood pressure sensor 440. The pressure sensor 200 includes any of the pressure sensors described in regard to the embodiments described above or a pressure sensor according to a modification of these pressure sensors.

Thus, it is possible to perform highly-sensitive pressure sensing by a small size pressure sensor. The blood pressure sensor 440 can perform a continuous blood pressure measurement by the pressure sensor 200 being pressed onto skin 443 over an arterial vessel 441.

According to the embodiment, it is possible to provide a blood pressure sensor of high sensitivity.

Eighth Embodiment

The embodiment relates to a touch panel using the pressure sensor of the embodiments described above.

FIG. 53 is a schematic plan view illustrating a touch panel according to the seventh embodiment.

In the embodiment, the pressure sensor 200 may be used in a touch panel 450. The pressure sensor 200 includes any of the pressure sensors described in regard to the embodiments described above or a pressure sensor according to a modification of these pressure sensors. In the touch panel 450, the pressure sensor 200 is mounted in at least either of the interior of the display and the outside the display.

For example, the touch panel 450 includes plural first interconnects 451, plural second interconnects 452, the plural pressure sensors 200, and a controller 453.

In the example, the plural first interconnects 451 are arranged along the Y-axis direction. Each of the plural first interconnects 451 extends along the X-axis direction. The plural second interconnects 452 are arranged along the X-axis direction. Each of the plural second interconnects 452 extends along the Y-axis direction.

The plural pressure sensors 200 are provided respectively at intersection portions between the plural first interconnects 451 and the plural second interconnects 452. One pressure sensor 200 is used as one detecting component 200e for detection. Herein, the intersection portions include positions where the first interconnects 451 and the second interconnects 452 intersect with each other and peripheral regions thereof.

One end 251 of each of the plural pressure sensors 200 is connected to each of the plural first interconnects 451. The other end 252 of each of the plural pressure sensors 200 is connected to each of the plural second interconnects 452.

The controller 453 is connected to the plural first interconnects 451 and the plural second interconnects 452.

For example, the controller 453 includes a first interconnect circuit 453a that is connected to the plural first interconnects 451, a second interconnect circuit 453b that is connected to the plural second interconnects 452, and a control circuit 455 that is connected to the first interconnect circuit 453a and the second interconnect circuit 453b.

The pressure sensor 200 having a small size can perform highly-sensitive pressure sensing. Thus, it is possible to realize a high definition touch panel.

Other than the applications described above, the pressure sensors according to the embodiments described above are applicable to various pressure sensor devices such as an atmospheric pressure sensor, an air pressure sensor of a tire.

According to the embodiments, it is possible to provide a strain sensing element of high sensitivity, a pressure sensor, a microphone, a blood pressure sensor, and a touch panel.

Hereinabove, the embodiments of the invention are described with reference to the specific examples. However, the invention is not limited to the specific examples. For example, specific configurations of the respective components such as the substrate, the strain sensing element, the first magnetic layer, the second magnetic layer, the spacer layer and the bias layer included in, for example, the strain sensing element, the pressure sensor, the microphone, the blood pressure sensor and the touch panel are included in the scope of the invention as long as the specific configurations can be appropriately selected by those skilled in the art from known techniques to realize the invention in the same way and to achieve the same results.

Further, combinations of two or more components of the respective specific examples in a technically allowable range are also included in the scope of the invention in a range without departing from the spirit of the invention.

In addition, all strain sensing elements, pressure sensors, microphones, blood pressure sensors and touch panels obtainable by an appropriate design modification by those skilled in the art based on the strain sensing elements, the pressure sensors, the microphones, the blood pressure sensors and the touch panels described above as the embodiments of the invention also are included in the scope of the invention in a range without departing from the spirit of the invention.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A strain sensing element provided on a deformable substrate, comprising:
   a first layer having a first magnetization;
   a second layer having a second magnetization to change according to a deformation of the substrate;
   an intermediate layer provided between the first layer and the second layer; and
   a third layer,
   the second layer being provided between the intermediate layer and the third layer,
   the third layer including at least one of a first material or a second material,
   the first material including at least one selected from the group consisting of Ir—Mn, Pt—Mn, Pd—Pt—Mn, and Ru—Rh—Mn, and
   the second material including at least one selected from the group consisting of CoPt (a ratio of Co being not less than 50 at. % and not more than 85 at. %), $(Co_xPt_{100-x})_{100-y}Cr_y$ (x being not less than 50 at. % and not more than 85 at. %, and y being not less than 0 at. % and not more than 40 at. %), and FePt (a ratio of Pt being not less than 40 at. % and not more than 60 at. %).

2. The element according to claim 1, wherein the first magnetization is pinned.

3. The element according to claim 1, further comprising:
   a fourth layer provided between the third layer and the second layer, the fourth layer being magnetic; and
   a fifth layer provided between the fourth layer and the second layer, the fifth layer being non-magnetic.

4. The element according to claim 3, wherein
   the fourth layer includes at least one selected from the group consisting of Co, Fe, and Ni, and
   the fifth layer includes at least one selected from the group consisting of Cu, Ru, Rh, Ir, V, Cr, Nb, Mo, Ta, W, Rr, Au, Ag, Pt, Pd, Ti, Zr, and Hf.

5. The element according to claim 3, further comprising:
   a sixth layer provided between the third layer and the fourth layer;
   a seventh layer provided between the sixth layer and the fourth layer; and
   a relative angle between a magnetization of the fourth layer and a magnetization of the sixth layer is 180°.

6. The element according to claim 3, wherein the fifth layer includes at least one selected from the group consisting of copper (Cu), gold (Au), silver (Ag), chrome (Cr), ruthenium (Ru), and iridium (Ir).

7. The element according to claim 1, wherein the third layer applies a magnetic bias to the second layer, and a relative angle between a direction of the magnetic bias in the second layer and the first magnetization is 180°.

8. The element according to claim 1, wherein the third layer applies a magnetic bias to the second layer, and a relative angle between a direction of the magnetic bias in the second layer and the first magnetization is not less than 90° and not more than 270°.

9. The element according to claim 1, wherein a coercivity of the second magnetic layer is not more than 10 Oe.

10. The element according to claim 1, wherein at least one of at least a part of the first layer or at least a part of the second layer is amorphous.

11. The element according to claim 1, wherein at least one of the first layer or the second layer includes boron.

12. The element according to claim 1, further comprising:
    an eighth layer,
    the first layer being provided between the eighth layer and the intermediate layer,
    the first magnetization being configured to change according to a deformation,
    the eight layer including at least one of a third material or a fourth material,
    the third material including at least one selected from the group consisting of Ir—Mn, Pt—Mn, Pd—Pt—Mn, and Ru—Rh—Mn, and
    the fourth material including at least one selected from the group consisting CoPt (a ratio of Co being not less than 50 at. % and not more than 85 at. %), $(Co_xPt_{100-x})_{100-y}Cr_y$ (x being not less than 50 at. % and not more than 85 at. %, and y being not less than 0 at. % and not more than 40 at. %), and FePt (a ratio of Pt being not less than 40 at. % and not more than 60 at. %).

13. The element according to claim 12, further comprising:
    a ninth layer provided between the eighth layer and the first layer, the ninth layer being magnetic; and
    a tenth layer provided between the ninth layer and the first layer, the tenth layer being non-magnetic.

14. The element according to claim 13, wherein
the ninth layer includes at least one selected from the group consisting of Co, Fe, and Ni, and
the tenth layer includes at least one selected from the group consisting of Cu, Ru, Rh, Ir, V, Cr, Nb, Mo, Ta, W, Rr, Au, Ag, Pt, Pd, Ti, Zr, and Hf.

15. The element according to claim 13, further comprising:
an eleventh layer provided between the eighth layer and the ninth layer;
a twelfth layer provided between the eleventh layer and the eighth layer; and
a relative angle between a magnetization of the ninth layer and a magnetization of the eleventh layer is 180°.

16. The element according to claim 15, further comprising:
a lower first magnetic coupling layer provided between the lower first bias magnetic layer and the lower second bias magnetic layer and configured to cause antiferromagnetic coupling to occur between the lower first bias magnetic layer and the lower second bias magnetic layer,
wherein the third layer applies a first magnetic bias to the second layer,
the eighth layer applies a second magnetic bias to the first layer, and
a relative angle between a direction of the first magnetic bias in the second layer and a direction of the second magnetic bias in the first layer is 180°.

17. The element according to claim 13, wherein
the tenth layer includes at least one selected from the group consisting of copper (Cu), gold (Au), silver (Ag), chrome (Cr), ruthenium (Ru), and iridium (Ir).

18. The element according to claim 12, wherein
the third layer applies a first magnetic bias to the second layer,
the eight layer applies a second magnetic bias to the first layer, and
a relative angle between a direction of the first magnetic bias in the second layer and a direction of the second magnetic bias in the first layer is 180°.

19. The element according to claim 12, wherein
a coercivity of the first layer is not more than 10 Oe, and
a coercivity of the second layer is not more than 10 Oe.

20. The element according to claim 12, wherein
at least one of at least a part of the first layer or at least a part of the second layer is amorphous.

21. The element according to claim 12, wherein
at least one of the first layer or the second layer includes boron.

22. A pressure sensor comprising:
a support unit;
a substrate supported by the support unit, the substrate being deformable; and
a strain sensing element provided on the substrate, the strain sensing element including
a first layer having a first magnetization,
a second layer having a second magnetization to change according to a deformation of the substrate,
an intermediate layer provided between the first layer and the second layer, and
a third layer,
the second layer being provided between the intermediate layer and the third layer,
the third layer including at least one of a first material or a second material,
the first material including at least one selected from the group consisting of Ir—Mn, Pt—Mn, Pd—Pt—Mn, and Ru—Rh—Mn, and
the second material including at least one selected from the group consisting CoPt (a ratio of Co being not less than 50 at. % and not more than 85 at. %), $(Co_xPt_{100-x})_{100-x}Cr_y$ (x being not less than 50 at. % and not more than 85 at. %, and y being not less than 0 at. % and not more than 40 at. %), and FePt (a ratio of Pt being not less than 40 at. % and not more than 60 at %).

23. The sensor according to claim 22, wherein the strain sensing element further includes:
a fourth layer provided between the third layer and the second layer, the fourth layer being magnetic, and
a fifth layer provided between the fourth layer and the second layer, the fifth layer being non-magnetic, and
a first angle formed by a magnetization of the fourth layer and a first straight line is in a first range or a second range,
the first range is not less than 0° and not more than 15°,
the second range is not less than 75° and not more than 105°, and
the first straight line connects an outer edge of the substrate and a centroid of the strain sensing element in shortest distance.

24. The sensor according to claim 22, wherein the strain sensing element further includes:
a fourth layer provided between the third layer and the second layer, the fourth layer being magnetic, and
a fifth layer provided between the fourth layer and the second layer, the fifth layer being non-magnetic, and
a second angle formed by a magnetization of the fourth layer and a second straight line is in a first range or a second range,
the first range is not less than 0° and not more than 15°,
the second range is not less than 75° and not more than 105°, and
the second straight line connects a centroid of the substrate and a centroid of the strain sensing element in shortest distance.

25. The sensor according to claim 22, wherein a plurality of strain sensing elements are provided on the substrate.

26. The sensor according to claim 25, wherein at least two of the plurality of strain sensing elements are electrically connected in series.

27. The sensor according to claim 26, wherein a voltage applied between terminals of the plurality of strain sensing elements that are electrically connected in series is not less than 1 V and not more than 10 V.

28. The sensor according to claim 26, wherein the number of the plurality of strain sensing elements that are electrically connected in series is not less than 6 and not more than 200.

29. A microphone, comprising:
a cover; and
the pressure sensor according to claim 22, the pressure sensor being provided in the cover.

30. A blood pressure sensor including the pressure sensor according to claim 22.

31. A touch panel, comprising:
a first interconnect;
a second interconnect; and
the pressure sensor according to claim 22,
the pressure sensor being provided at an intersection between the first interconnect and the second interconnect.

* * * * *